(12) United States Patent
Takeshita et al.

(10) Patent No.: US 9,228,215 B2
(45) Date of Patent: Jan. 5, 2016

(54) METHOD FOR PRODUCING A TARGET SUBSTANCE BY FERMENTATION

(71) Applicant: AJINOMOTO CO., INC., Tokyo (JP)

(72) Inventors: Ryo Takeshita, Kawasaki (JP); Naoki Kadotani, Kawasaki (JP); Kenji Abe, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 14/085,171

(22) Filed: Nov. 20, 2013

(65) Prior Publication Data

US 2014/0080185 A1    Mar. 20, 2014

Related U.S. Application Data

(60) Division of application No. 12/833,547, filed on Jul. 9, 2010, now Pat. No. 8,617,852, which is a continuation of application No. PCT/JP2009/050157, filed on Jan. 8, 2009.

(30) Foreign Application Priority Data

Jan. 10, 2008 (JP) ................. 2008-003556

(51) Int. Cl.
| | |
|---|---|
| C12P 13/22 | (2006.01) |
| C12P 13/04 | (2006.01) |
| C12P 13/08 | (2006.01) |
| C12P 19/34 | (2006.01) |
| C12N 1/20 | (2006.01) |
| C12N 9/24 | (2006.01) |
| C07H 21/04 | (2006.01) |
| C07K 1/00 | (2006.01) |
| C12N 9/12 | (2006.01) |

(52) U.S. Cl.
CPC ............. *C12P 13/08* (2013.01); *C12N 9/1205* (2013.01); *C12N 9/2402* (2013.01); *C12P 13/22* (2013.01); *C12Y 302/0101* (2013.01)

(58) Field of Classification Search
CPC .... C12N 9/1205; C12N 9/2402; C12P 13/08; C12P 13/22; C12Y 302/0101
USPC ............... 435/108, 16, 115, 91.1, 252.3, 200; 536/23.1, 23.2; 530/350
See application file for complete search history.

(56) References Cited

U.S. PATENT DOCUMENTS

| | | | |
|---|---|---|---|
| 6,617,148 B2 | 9/2003 | Bedzyk et al. | |
| 7,097,999 B2 | 8/2006 | Tsujimoto et al. | |
| 8,617,852 B2 * | 12/2013 | Takeshita et al. | 435/106 |
| 2003/0077764 A1 | 4/2003 | Tsujimoto et al. | |
| 2004/0171023 A1 | 9/2004 | Caimi et al. | |
| 2007/0243590 A1 | 10/2007 | Takeshita et al. | |
| 2009/0215130 A1 | 8/2009 | Iyo et al. | |
| 2009/0258401 A1 | 10/2009 | Iyo et al. | |
| 2011/0003347 A1 | 1/2011 | Takeshita et al. | |

FOREIGN PATENT DOCUMENTS

| | | |
|---|---|---|
| EP | 0149915 | 7/1985 |
| EP | 1254957 | 11/2002 |
| JP | 2002-330763 | 11/2002 |
| JP | 2006-504412 | 2/2006 |
| WO | WO2004/018645 | 3/2004 |

OTHER PUBLICATIONS

Database DDBJ/EMBL/GenBank [online]. Accession No. CAB12647, Apr. 18, 2005.
Database DDBJ/EMBL/GenBank [online]. Accession No. CAB12649, Apr. 18, 2005.
Database DDBJ/EMBL/GenBank [online]. Accession No. CAB15461, Nov. 15, 2007.
Pikis, A., et al., "Genetic Requirements for Growth of *Escherichia coli* K12 on Methyl-alpha-D-glucopyranoside and the Five-alpha-D-Glucosyl-D-fructose Isomers of Sucrose," J. Biol. Chem. 2006;281(26):17900-17908.
Robrish, S. A., et al., "Phosphoenolpyruvate-Dependent Maltose:Phosphotransferase Activity in Fusobacterium mortiferum ATCC 25557: Specificity, Inducibility, and Product Analysis," J. Bacteriol. 1994;176(11):3250-3256.
Schönert, S., et al., "Identification and Enzymatic Characterization of the Maltose-Inducible alpha-Glucosidase MalL (Sucrase-Isomaltase-Maltase) of *Bacillus subtilis*," J. Bacteriol. 1998;180(9):2574-2578.
Schönert, S., et al., "Maltose and Maltodextrin Utilization by *Bacillus subtilis*," J. Bacteriol. 2006;188(11):3911-3922.
Thompson, J., et al., "Metabolism of Sucrose and Its Five Linkage-isomeric alpha-D-Glucosyl-D-fructoses by Klebsiella pneumoniae," J. Biol. Chem. 2001;276(40):37415-37425.
International Search Report for PCT Patent App. No. PCT/JP2009/050157 (Mar. 24, 2009).
Tateno, T., et al., "Production of L-Lysine from starch by Corynebacterium glutamicum displaying alpha-amylase on its cell surface," Appl. Microbiol. Biotechnol. 2007;74:1213-1220.
International Preliminary Report on Patentability for PCT Patent App. No. PCT/JP2009/050157 (Aug. 19, 2010).
Extended European Search Report for EP Patent App. No. 09700160.6 (Feb. 23, 2012).
Broun, P., et al., "Catalytic plasticity of fatty acid modification enzymes underlying chemical diversity of plant lipids," Science 1998;282:1315-1317.

(Continued)

*Primary Examiner* — Ganapathirama Raghu
(74) *Attorney, Agent, or Firm* — Shelly Guest Cermak; Cermak Nakajima & McGowan LLP

(57) ABSTRACT

A method is described for producing a target substance utilizing a microorganism by culturing the microorganism in a medium to produce and accumulate the target substance in the medium, and then collecting the target substance from culture. The microorganism is imparted with isomaltase activity, or modified to increase isomaltase activity.

17 Claims, 1 Drawing Sheet

(56) References Cited

OTHER PUBLICATIONS

Chica, R. A., et al., "Semi-rational approaches to engineering enzyme activity: combining the benefits of directed evolution and rational design," Curr. Opi. Biotechnol. 2005;16:378-384.

Devos, D., et al., "Practical limits of functional prediction," Proteins: Structure, Function, and Genetics 2000;41:98-107.

Kisselev, L., "Polypeptide release factors in prokaryotes and eukaryotes: same function, different structure," Structure 2002;10:8-9.

Seffernick, J. L., et al., "Melamine deaminase and Atrazine chlorohydrolase: 98 percent identical but functionally different," J. Bacteriol. 2001;183(8):2405-2410.

Sen, S., et al., "Developments in directed evolution for improving enzyme functions," Appl. Biochem. Biotechnol. 2007;143:212-223.

Whisstock, J., et al., "Prediction of protein function from protein sequence," Q. Rev. Biophysics 2003;36(3):307-340.

Wishart, M. J., et al., "A single mutation converts a novel phosphotyrosine binding domain into a dual-specificity phosphatase," J. Biol. Chem. 1995;270(45):26782-26785.

Devos, D., et al., "Practical limits of function prediction," Proteins: Structure, Function, and Genetics 2000;41:98-107. [This reference, which was previously cited in the IDS dated Nov. 20, 2013, is re-cited herein to correct a typographical error. As a copy is already of record, a copy is not included with this filing.].

Witkowski, A., et al., "Conversion of beta-Ketoacyl Synthase to a Malonyl Decarboxylase by Replacement of the Active-Site Cysteine with Glutamine," Biochem. 1999;38:11643-11650.

\* cited by examiner

METHOD FOR PRODUCING A TARGET SUBSTANCE BY FERMENTATION

This application is a Divisional of, and claims priority under 35 U.S.C. §120 to, U.S. patent application Ser. No. 12/833,547, filed Jul. 9, 2010, now U.S. Pat. No. 8,617,852, which was a Continuation under 35 U.S.C. §120 of PCT Patent Application No. PCT/JP2009/050157, filed Jan. 8, 2009, which claimed priority under 35 U.S.C. §119 to Japanese Patent Application No. 2008-003556, filed on Jan. 10, 2008, all of which are incorporated in their entireties by reference. The Sequence Listing in electronic format filed herewith is also hereby incorporated by reference in its entirety (File Name: 2013-11-20T_US-427D_Seq_List; File Size: 76 KB; Date Created: Nov. 20, 2013).

BACKGROUND OF THE INVENTION

1. Technical Field

The present invention relates to a method for producing a target substance by using a microorganism. More precisely, the present invention describes a method to improve production using a microorganism of final target products, such as L-amino acids, nucleic acids, and so forth.

2. Background Art

Methods are well-known for producing substances such as L-amino acids by fermentation using microorganisms. L-amino acids are used not only as seasonings and in foodstuffs, but also as components of various nutritional mixtures for medical purposes. Furthermore, they are used as additives for animal feed, reagents in the drug manufacturing and chemical industries, and as growth factors for production of L-amino acids such as L-lysine and L-homoserine. Microorganisms that can produce L-amino acids by fermentation include coryneform bacteria, *Escherichia* bacteria, *Bacillus* bacteria, *Serratia* bacteria, and so forth.

In the production of target substances by fermentation, most of the raw materials contain saccharides such as blackstrap molasses. Also in amino acid fermentation or nucleic acid fermentation, the culture is performed using a saccharide as the raw material. Although sugarcane and so forth contain abundant amounts of starch, it is rarely used as a raw material, but can be present as a decomposition product of starch, for example, monosaccharides or disaccharides. Starch decomposes in the presence of a solution of a saccharifying enzyme such as amylase, and polysaccharides are decomposed into relatively low molecular weight saccharides, such as glucose, maltose and isomaltose.

When using a starch hydrolysis solution in fermentation, if the fermentation is terminated when all the glucose is consumed, oligosaccharides such as maltose and isomaltose are not assimilated. *Escherichia* bacteria do not have the ability to assimilate these oligosaccharides, especially isomaltose, and they cause the Maillard reaction with the products of the fermentation, especially L-amino acids, which poses a problem when purifying the fermentation product.

Moreover, once all the glucose is consumed, the remaining oligosaccharides such as maltose that were not consumed due to the presence and consumption of glucose must be consumed, thus extending the culture time and needlessly increasing the heating expense.

A technique has been disclosed to utilize the maltose produced by starch decomposition, specifically, to use a microorganism in which an interaction is attenuated or eliminated between the $IIA^{Glc}$ protein of the glucose PTS and the MalK protein involved in the non-PTS uptake of maltose, resulting in the microorganism being able to take up glucose and maltose simultaneously (U.S. Pat. No. 7,097,999, European Patent Laid-open No. 1254957). It is known that the suppression of the uptake of other oligosaccharides by glucose is generally observed in *E. coli* and *Salmonella typhimurium*. That is, when glucose and other carbon sources such as maltose are present during fermentation, glucose is assimilated first, and then the other carbon sources are assimilated. However, the aforementioned technique enables simultaneous assimilation of glucose and maltose.

Furthermore, an α-amylase can be expressed in a cell surface layer to decompose starch into glucose and maltose (which is an α-1,4-glucan), which are then taken up into cells, which can result in an improved ability to produce amino acids (Tateno, T., et al., Appl. Microbiol. Biotech., 74, 1213-1220 (2007)).

Maltose is known to be taken up into cells by the GlvC protein, also known as the PTS maltose enzyme IICB, encoded by the glvC gene of *Bacillus subtilis* (*B. subtilis*). Once in the cell, maltose, present as phosphorylated maltose, is hydrolyzed by GlvA (6-phospho-α-glucosidase) encoded by the glvA gene (Schonert S. et al., J. Bacteriol., 2006, June; 188 (11):3911-22). However, the relationship between the glvAC genes and isomaltose assimilation has not been reported to date.

The enzyme α-glucosidase decomposes maltose, sucrose, and isomaltose into monosaccharides, and is present in *B. subtilis*. α-glucosidase is encoded by the malL gene (Schonert, S., et al., J. Bacteriol., 180, 2574-2578 (1998)).

The presence of such an enzyme as described above has not been reported for coryneform bacteria and Enterobacteriaceae bacteria, including *E. coli*. Therefore, it is considered in the art that these bacteria cannot assimilate isomaltose, and whether they can take isomaltose up into cells is unknown. Furthermore, a microorganism that extracellularly secretes an enzyme that decomposes isomaltose has also not been reported.

SUMMARY OF THE INVENTION

Aspects of the present invention include providing a method for producing a target substance from isomaltose by fermentation utilizing a microorganism, a method for producing a target substance by fermentation utilizing a microorganism in a medium containing isomaltose and/or maltose, and microorganisms used for these methods. The isomaltose and/or maltose can be present as raw materials in the fermentation, or as impurities in the medium.

It has been found that a microorganism with increased isomaltase activity, whether this activity is imparted to the microorganism or is native to the microorganism, can efficiently assimilate isomaltose. It has been further found that if the glvA and glvC genes of *Bacillus subtilis* are introduced into a microorganism to increase the isomaltase and maltase activities, the presence of impurities in the medium, such as isomaltose and maltose, can be reduced.

It is an aspect of the present invention to provide a method for producing a L-amino acid or a nucleic acid utilizing a microorganism, which comprises culturing the microorganism in a medium, and collecting the L-amino acid or a nucleic acid from the medium, wherein: the microorganism has been modified so that: A) it comprises isomaltase activity, and/or B) the isomaltase activity is increased, and wherein said activity causes the decomposition of phosphorylated isomaltose into glucose and glucose phosphate.

It is a further aspect of the present invention to provide the method as described above, wherein the microorganism has been further modified so that: A) it is able to take up isomaltose, and/or B) the activity to take up isomaltose is increased.

It is a further aspect of the present invention to provide the method as described above, wherein the microorganism has been further modified so that: A) it comprises maltase activity, and/or B) the maltase activity is increased.

It is a further aspect of the present invention to provide the method as described above, wherein the microorganism is further modified so that: A) it is able to take up maltose, and/or B) the activity to take up maltose is increased.

It is a further aspect of the present invention to provide the method as described above, wherein the medium contains a component selected from the group consisting of A) isomaltose and B) isomaltose and maltose.

It is a further aspect of the present invention to provide the method as described above, wherein the microorganism comprises a gene coding for isomaltase of a *Bacillus* bacterium.

It is a further aspect of the present invention to provide the method as described above, wherein the isomaltase is selected from the group consisting of:

(A) a protein comprising the amino acid sequence shown in SEQ ID NO: 14, (B) a protein comprising the amino acid sequence shown in SEQ ID NO: 14, but wherein one or several amino acid residues are substituted, deleted, inserted or added, and the protein has isomaltase activity.

It is a further aspect of the present invention to provide the method as described above, wherein the isomaltase is encoded by a DNA selected from the group consisting of:

(A) a DNA comprising the nucleotide sequence shown in SEQ ID NO: 13, (B) a DNA which is able to hybridize with a sequence complementary to the nucleotide sequence of SEQ ID NO: 13 or a probe which can be prepared from the nucleotide sequence under stringent conditions, and codes for a protein having the isomaltase activity.

It is a further aspect of the present invention to provide the method as described above, wherein the isomaltase is selected from the group consisting of:

(A) a protein comprising the amino acid sequence shown in SEQ ID NO: 40, (B) a protein comprising the amino acid sequence shown in SEQ ID NO: 40, but wherein one or several amino acid residues are substituted, deleted, inserted or added, and the protein has isomaltase activity.

It is a further aspect of the present invention to provide the method as described above, wherein the isomaltase is encoded by a DNA selected from the group consisting of:

(A) a DNA comprising the nucleotide sequence shown in SEQ ID NO: 39, (B) a DNA which is able to hybridize with a sequence complementary to the nucleotide sequence of SEQ ID NO: 39 or a probe which can be prepared from the nucleotide sequence under stringent conditions, and codes for a protein having the isomaltase activity.

It is a further aspect of the present invention to provide the method as described above, wherein the microorganism comprises a gene coding for PTS maltose enzyme IICB of a *Bacillus* bacterium.

It is a further aspect of the present invention to provide the method as described above, wherein the PTS maltose enzyme IICB is selected from the group consisting of:

(A) a protein comprising the amino acid sequence shown in SEQ ID NO: 42, (B) a protein comprising the amino acid sequence shown in SEQ ID NO: 42, but wherein one or several amino acid residues are substituted, deleted, inserted or added, and the protein is able to cause the microorganism to take up isomaltose.

It is a further aspect of the present invention to provide the method as described above, wherein the PTS maltose enzyme IICB is encoded by a DNA selected from the group consisting of:

(A) a DNA comprising the nucleotide sequence shown in SEQ ID NO: 41, (B) a DNA which is able to hybridize with a sequence complementary to the nucleotide sequence of SEQ ID NO: 41 or a probe which can be prepared from the nucleotide sequence under stringent conditions, and codes for a protein which is able to cause the microorganism to take up isomaltose.

It is a further aspect of the present invention to provide the method as described above, wherein the microorganism is an Enterobacteriaceae bacterium.

It is a further aspect of the present invention to provide the method as described above, wherein the microorganism is an *Escherichia* bacterium.

It is a further aspect of the present invention to provide the method as described above, wherein the *Escherichia* bacterium is *Escherichia coli*.

It is a further aspect of the present invention to provide the method as described above, wherein the amino acid is selected from the group consisting of L-lysine, L-threonine, and L-phenylalanine.

DETAILED DESCRIPTION OF THE PREFERRED EMBODIMENTS

Figure 1:
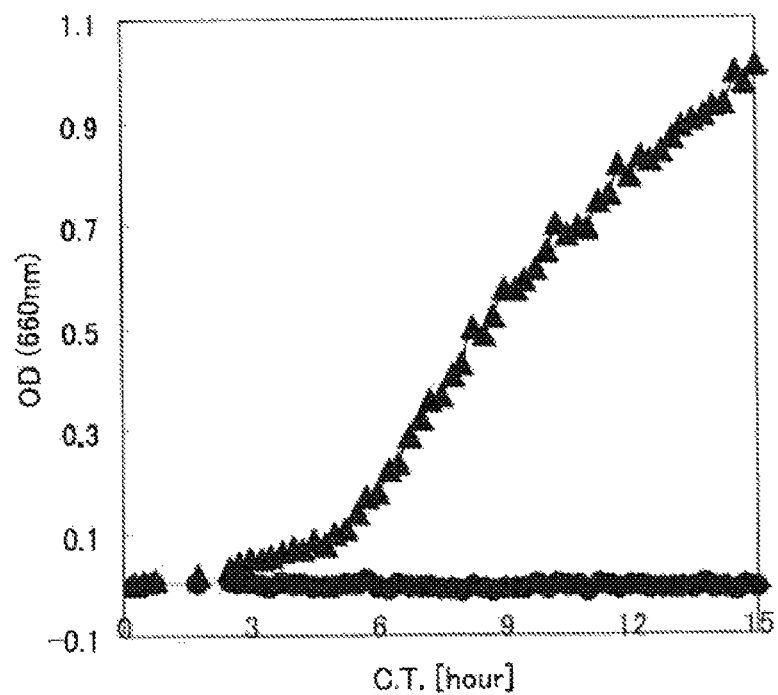
FIG. 1 shows growth curves of the pTWV229+pMW219-ΔPlac/MG1655 strain (●) and the glvA+glvC/MG1655 strain (▲) in the M9-iMal (0.2%) medium.

The target substance produced by a microorganism can be an L-amino acid or a nucleic acid. The "L-amino acid" is not particularly limited, so long as it is an L-amino acid that can accumulate in the medium during fermentation of a microorganism. Although the type of L-amino acid is not particularly limited, examples include basic amino acids such as L-lysine, L-ornithine, L-arginine, L-histidine and L-citrulline; aliphatic amino acids such as L-isoleucine, L-alanine, L-valine, L-leucine and glycine; amino acids which are hydroxy-monoaminocarboxylic acids such as L-threonine and L-serine; cyclic amino acids such as L-proline; aromatic amino acids such as L-phenylalanine, L-tyrosine and L-tryptophan; sulfur-containing amino acids such as L-cysteine, L-cystine and L-methionine; acidic amino acids and acid amides thereof such as L-glutamic acid, L-asparatic acid, L-glutamine and L-asparagine.

The microorganism can have the ability to produce two or more types of amino acids.

The L-amino acid can be a free L-amino acid, or can be a salt of an L-amino acid, such as sulfate, hydrochloride, carbonate, ammonium salt, sodium salt, and potassium salt.

The "nucleic acid" is not particularly limited, so long as it is a nucleic acid that can accumulate in the medium during fermentation of a microorganism. Examples of nucleic acids include purine nucleosides, purine nucleotides, and so forth. The purine nucleosides include inosine, xanthosine, guanosine, adenosine, and so forth; and the purine nucleotides include 5'-phosphate esters of the purine nucleosides, for example, inosinic acid, (inosine-5'-phosphate, also referred to as "IMP"), xanthylic acid (xanthosine-5'-phosphate, also referred to as "XMP"), guanylic acid (guanosine-5'-monophosphate, also referred to as "GMP"), adenylic acid (adenosine-5'-monophosphate, also referred to as "AMP"), and so forth.

The microorganism can have the ability to produce two or more kinds of nucleic acids.

The nucleic acid can include a free nucleic acid, or a nucleic acid salt such as a sodium salt and a potassium salt.

The microorganism can be imparted with isomaltase activity, or it can be modified to increase the native isomaltase activity.

The "isomaltase activity" can mean an activity which causes decomposition of isomaltose into two glucose molecules (EC 3.2.1.10), or an activity which causes decomposition of phosphorylated isomaltose, which is produced when isomaltose is taken up into cells, into glucose and glucose phosphate (EC 3.2.1.122). Furthermore, "isomaltase" can mean an enzyme having isomaltase activity. For example, even an enzyme having an activity to decompose maltose, and generally called maltase, can be an isomaltase, if the enzyme has an activity to decompose isomaltose. Therefore, isomaltase can also be called maltose-inducible α-glucosidase or oligo-1,6-glucosidase.

The "maltase activity" can mean an activity to cause decomposition of maltose into two glucose molecules (EC 3.2.1.20), or an activity to cause decomposition of phosphorylated maltose into glucose and glucose phosphate (EC 3.2.1.122).

The isomaltase activity can be measured by the method described by Thompson J. (1: J. Biol. Chem., 1998 October, 16; 273 (42):27347-56.) using isomaltose as the substrate instead of maltose. The maltase activity can be measured by the method described by Thompson J. mentioned above.

In addition to imparting or increasing the isomaltase and/or the maltase activity, an activity to take up isomaltose and/or maltose can be imparted or enhanced. The "activity to take up isomaltose" can mean an activity to transport isomaltose from the exterior of the cells into the interior of the cells. Isomaltose can be taken up into a cell by an isomaltose transporter or an isomaltose-specific permease. The transporter includes transporters of the phosphotransferase system (PTS) and the major facilitator superfamily (MFS), as well as ABC transporters. For example, transporters of the phosphotransferase system can be enhanced. The activity to take up isomaltose can be confirmed by the methods described in J. Bacteriol., 1991 April; 173(7):2180-2186 and J. Biol. Chem., 2006 June, 30; 281 (26):17900-17908.

Furthermore, the activity to take up isomaltose can also include the activity to take up maltose.

Examples of microorganisms include, specifically, Enterobacteriaceae bacteria belonging to the genus *Escherichia, Enterobacter, Klebsiella, Pantoea, Serratia, Erwinia, Salmonella, Morganella*, or the like; coryneform bacteria, *Bacillus* bacteria, *Streptococcus* bacteria, *Saccharomyces* yeasts, and so forth. A microorganism in which gene substitution is possible is also an example.

Examples of the *Escherichia* bacteria include *Escherichia coli* and so forth. When *Escherichia coli* is bred by using genetic engineering techniques, the *E. coli* K12 strain and derivatives thereof, the *Escherichia coli* 1655 strain (ATCC 47076), and the *Escherichia coli* W3110 strain (ATCC 27325) can be used. The K-12 strain of *Escherichia coli* and the derivative strains can be obtained from, for example, the American Type Culture Collection (ATCC, Address: P.O. Box 1549, Manassas, Va. 20108, United States of America).

The microorganism may or may not inherently have the ability to assimilate isomaltose. The "ability to assimilate isomaltose" can mean the ability of a microorganism to metabolize isomaltose when used as a carbon source in fermentation of the microorganism in a medium.

Examples of microorganisms which do not inherently have the ability to assimilate isomaltose include Enterobacteriaceae bacteria, coryneform bacteria, and so forth. Furthermore, examples of microorganisms which do have a native ability to assimilate isomaltose include microorganisms which either have the native activity to take up isomaltose, or have a native intracellular isomaltase activity. Examples of such microorganisms include *Bacillus* bacteria, *Streptococcus* bacteria, *Saccharomyces* yeasts, and so forth.

The microorganism can be obtained by imparting isomaltase activity to a parent strain of a microorganism which is able to produce a target substance, or by modifying such a parent strain to increase the native isomaltase activity. The microorganism can also be obtained by imparting the ability to produce a target substance to a microorganism which has a native isomaltase activity. The microorganism can also be obtained by imparting or enhancing the ability to produce a target substance to a parent strain, and then modifying this strain so that the isomaltase activity is increased.

As the *Escherichia* bacteria, those described in the work of Neidhardt et al. (Neidhardt, F. C. et al., *Escherichia coli* and *Salmonella Typhimurium*, American Society for Microbiology, Washington D.C., 1208, table 1), such as *Escherichia coli*, can be utilized. Examples of wild-type or parent strains of *Escherichia coli* include, for example, the K12 strain and derivatives thereof, *Escherichia coli* MG1655 strain (ATCC No. 47076), W3110 strain (ATCC No. 27325), and so forth. These strains are available from the American Type Culture Collection (ATCC, Address: P.O. Box 1549, Manassas, Va. 20108, United States of America).

Furthermore, examples of the *Enterobacter* bacteria include *Enterobacter agglomerans, Enterobacter aerogenes*, and so forth, and examples of the *Pantoea* bacteria include *Pantoea ananatis*. Some species of *Enterobacter agglomerans* have been recently re-classified into *Pantoea agglomerans, Pantoea ananatis, Pantoea stewartii* or the like, based on the nucleotide sequence analysis of 16S rRNA, etc. Both of the *Enterobacter* bacteria and *Pantoea* bacteria can be used so long as the chosen bacterium is classified into the family Enterobacteriaceae. When a *Pantoea ananatis* strain is bred by a genetic engineering technique, *Pantoea ananatis* AJ13355 strain (FERM BP-6614), AJ13356 strain (FERM BP-6615), AJ13601 strain (FERM BP-7207) and derivatives thereof can be used. These strains were identified as *Enterobacter agglomerans* when they were isolated, and deposited as *Enterobacter agglomerans*. However, they were recently re-classified as *Pantoea ananatis* on the basis of nucleotide sequencing of 16S rRNA and so forth as described above.

The coryneform bacteria are defined in Bergey's Manual of Determinative Bacteriology, 8th Ed., p. 599 (1974), and include microorganisms which are aerobic, Gram-positive and nonacid-fast bacilli, and are unable to sporulate. The coryneform bacteria include bacteria which have previously been classified into the genus *Brevibacterium* but are presently classified into the genus *Corynebacterium* (Int. J. Syst. Bacteriol. 41:255-260 (1991)), and bacteria belonging to the genus *Brevibacterium* or *Microbacterium*, which are closely related to the genus *Corynebacterium*.

Specific examples of such coryneform bacteria include the following:

Corynebacterium acetoacidophilum
Corynebacterium acetoglutamicum
Corynebacterium alkanolyticum
Corynebacterium callunae
Corynebacterium glutamicum
Corynebacterium lilium
Corynebacterium melassecola
Corynebacterium thermoaminogenes (Corynebacterium efficiens)
Corynebacterium herculis
Brevibacterium divaricatum
Brevibacterium flavum
Brevibacterium immariophilum
Brevibacterium lactofermentum
Brevibacterium roseum
Brevibacterium saccharolyticum
Brevibacterium thiogenitalis
Corynebacterium ammoniagenes
Brevibacterium album
Brevibacterium cerinum
Microbacterium ammoniaphilum Specific examples of these bacteria include the following strains:

Corynebacterium acetoacidophilum ATCC 13870
Corynebacterium acetoglutamicum ATCC 15806
Corynebacterium alkanolyticum ATCC 21511
Corynebacterium callunae ATCC 15991
Corynebacterium glutamicum ATCC 13020, ATCC 13032, ATCC 13060
Corynebacterium lilium ATCC 15990
Corynebacterium melassecola ATCC 17965
Corynebacterium efficiens AJ12340 (FERM BP-1539)
Corynebacterium herculis ATCC 13868
Brevibacterium divaricatum ATCC 14020
Brevibacterium flavum ATCC 13826, ATCC 14067, AJ12418 (FERM BP-2205)
Brevibacterium immariophilum ATCC 14068
Brevibacterium lactofermentum ATCC 13869 (Corynebacterium glutamicum ATCC 13869)
Brevibacterium roseum ATCC 13825
Brevibacterium saccharolyticum ATCC 14066
Brevibacterium thiogenitalis ATCC 19240
Brevibacterium ammoniagenes ATCC 6871, ATCC 6872
Brevibacterium album ATCC 15111
Brevibacterium cerinum ATCC 15112
Microbacterium ammoniaphilum ATCC 15354

These strains are available from, for example, the American Type Culture Collection (ATCC) (Address: P.O. Box 1549, Manassas, Va. 2010812301 Parklawn Drive, Rockville, Md. 20852, United States of America). That is, registration numbers are given to each of the strains, and the strains can be ordered by using these registration numbers. The registration numbers of the strains are listed in the catalogue of the American Type Culture Collection (refer to www.atcc.org/). The AJ12340 strain was deposited on Oct. 27, 1987 at the National Institute of Bioscience and Human Technology, Agency of Industrial Science and Technology, Ministry of Economy, Trade and Industry (currently independent administrative agency, National Institute of Advanced Industrial Science and Technology, International Patent Organism Depositary, Tsukuba Central 6, 1-1, Higashi 1-Chome, Tsukuba-shi, Ibaraki-ken, 305-5466, Japan), with an accession number of FERM BP-1539 under the provisions of Budapest Treaty. The AJ12418 strain was deposited under the provisions of the Budapest Treaty on Jan. 5, 1989 at the National Institute of Bioscience and Human Technology, Agency of Industrial Science and Technology, Ministry of Economy, Trade and Industry with an accession number of FERM BP-2205.

Examples of Bacillus bacteria include Bacillus subtilis, Bacillus amyloliquefaciens, Bacillus pumilus, and so forth. Examples of Bacillus subtilis include Bacillus subtilis 168 Marburg strain (ATCC 6051), Bacillus subtilis PY79 strain (Plasmid, 1984, 12, 1-9), and so forth. Examples of Bacillus amyloliquefaciens include Bacillus amyloliquefaciens T strain (ATCC 23842), Bacillus amyloliquefaciens N strain (ATCC 23845), and so forth. Examples of Bacillus pumilus include Bacillus pumilus Gottheil No. 3218 (ATCC 21005) (U.S. Pat. No. 3,616,206), and so forth.

Hereinafter, methods for imparting the ability to produce L-amino acids or nucleic acids to such parent strains as mentioned above are described.

To impart the ability to produce an L-amino acid or a nucleic acid, methods conventionally employed in the breeding of coryneform bacteria or bacteria of the genus Escherichia (see "Amino Acid Fermentation", Gakkai Shuppan Center (Ltd.), 1st Edition, published May 30, 1986, pp. 77-100) can be used. Such methods include methods of acquiring an auxotrophic mutant, an analogue-resistant strain, or a metabolic regulation mutant, or constructing a recombinant strain so that it overexpresses an L-amino acid or nucleic acid biosynthesis enzyme. One or more of the above-described properties such as auxotrophy, analogue-resistance, or metabolic regulation mutation can be imparted. Expression of one or more L-amino acid biosynthesis enzymes can be enhanced. Furthermore, the methods of imparting properties such as an auxotrophic mutation, analogue resistance, or metabolic regulation mutation can be combined with the methods of enhancing the biosynthesis enzymes.

An auxotrophic mutant strain, L-amino acid or nucleic acid analogue-resistant strain, or metabolic regulation mutant strain with an ability to produce an L-amino acid or nucleic acid can be obtained by subjecting a parent strain or wild-type strain to a conventional mutagenesis, such as exposure to X-rays or UV irradiation, or treatment with a mutagen such as N-methyl-N'-nitro-N-nitrosoguanidine, or ethyl methanesulfonate (EMS), etc., and then selecting from the resulting mutant stains those which exhibit an autotrophy, analogue resistance, or metabolic regulation mutation, and which also have the ability to produce an L-amino acid.

Methods for imparting amino acid-producing ability and amino acid-producing bacteria will be specifically exemplified below.

L-Lysine-Producing Bacteria

L-Lysine-producing bacteria and methods for constructing them are exemplified below.

Examples of strains which are able to produce L-lysine include, for example, L-lysine analogue-resistant strains and metabolic regulation mutant strains. Examples of L-lysine analogues include, but are not limited to, oxalysine, lysine hydroxamate, S-(2-aminoethyl)-L-cysteine (also abbreviated as "AEC"), γ-methyllysine, α-chlorocaprolactam, and so forth. Mutant strains which are resistant to these lysine analogues can be obtained by subjecting an Enterobacteriaceae or a coryneform bacterium to a conventional artificial mutagenesis treatment. Specific examples of L-lysine-producing bacteria include Escherichia coli AJ11442 (FERM BP-1543, NRRL B-12185, see Japanese Patent Laid-open No. 56-18596 and U.S. Pat. No. 4,346,170), Escherichia coli VL611 (Japanese Patent Laid-open No. 2000-189180), and so forth. An example of an Escherichia coli strain which is able to produce L-lysine is the WC196 strain (see International Publication WO96/17930).

Furthermore, the activity of an L-lysine biosynthesis system enzyme can be increased in a parent bacterium to impart or increase the ability of the bacterium to produce L-lysine. The activity of such an enzyme can be increased by increasing the copy number of the gene coding for the enzyme in cells, or by modifying an expression control sequence thereof. The copy number of a gene coding for an enzyme of L-lysine biosynthesis system can be increased and/or an expression control sequence can be modified in the same manner as that for the isomaltase gene described below.

Examples of genes coding for L-lysine biosynthetic enzymes include genes coding for enzymes of the diaminopimelate pathway such as dihydrodipicolinate synthase gene (dapA), aspartokinase gene (lysC), dihydrodipicolinate reductase gene (dapB), diaminopimelate decarboxylase gene (lysA), diaminopimelate dehydrogenase gene (ddh) (WO96/40934 for all the foregoing genes), phosphoenolpyruvate carboxylase gene (ppc) (Japanese Patent Laid-open No. 60-87788), aspartate aminotransferase gene (aspC) (Japanese Patent Publication (Kokoku) No. 6-102028), diaminopimelate epimerase gene (dapF) (Japanese Patent Laid-open No. 2003-135066), and aspartate semialdehyde dehydrogenase gene (asd) (WO00/61723), and genes coding for enzymes of the aminoadipic acid pathway such as homoaconitate hydratase gene (Japanese Patent Laid-open No. 2000-157276). In addition, a parent strain can have an increased level of expression of the gene involved in energy efficiency (cyo) (EP 1170376 A), the gene coding for nicotinamide nucleotide transhydrogenase (pntAB) (U.S. Pat. No. 5,830,716), the ybjE gene coding for a protein having L-lysine excretion activity (WO2005/073390), the gene coding for glutamate dehydrogenase (gdhA) (Gene 23:199-209 (1983)), or an arbitrary combination of these. Abbreviations for the genes are shown in the parentheses.

It is known that the wild-type dihydrodipicolinate synthase derived from *Escherichia coli* is subject to feedback inhibition by L-lysine, and it is also known that the wild-type aspartokinase derived from *Escherichia coli* is subject to suppression and feedback inhibition by L-lysine. Therefore, mutant dapA and lysC genes which encode enzymes which are desensitized to the feedback inhibition by L-lysine can be used. Examples of DNA encoding a mutant dihydrodipicolinate synthetase desensitized to feedback inhibition by L-lysine include a DNA encoding such a protein having an amino acid sequence in which the histidine residue at the position 118 is replaced by tyrosine residue. Examples of DNA encoding a mutant aspartokinase desensitized to feedback inhibition by L-lysine include a DNA encoding an AKIII having an amino acid sequence in which the threonine residue at the position 352, the glycine residue at the position 323, and the methionine residue at the position 318 are replaced by isoleucine, asparagine and isoleucine residues, respectively (see U.S. Pat. Nos. 5,661,012 and 6,040,160). Such mutant DNAs can be obtained by site-specific mutagenesis using PCR or the like.

Wide host-range plasmids RSFD80, pCAB1, and pCABD2 contain a mutant dapA gene encoding a mutant dihydrodipicolinate synthase and a mutant lysC gene encoding a mutant aspartokinase (U.S. Pat. No. 6,040,160). *Escherichia coli* JM109 strain transformed with RSFD80 was named AJ12396 (U.S. Pat. No. 6,040,160), and the strain was deposited at the National Institute of Bioscience and Human-Technology, Agency of Industrial Science and Technology, Ministry of International Trade and Industry (currently National Institute of Advanced Industrial Science and Technology, International Patent Organism Depositary) on Oct. 28, 1993 and assigned an accession number of FERM P-13936, and the deposit was then converted to an international deposit under the provisions of Budapest Treaty on Nov. 1, 1994 and assigned an accession number of FERM BP-4859. RSFD80 can be obtained from the AJ12396 strain by a conventional method.

Furthermore, in bacteria able to produce L-amino acids, the activities of enzymes that catalyze a reaction branching off from an L-amino acid biosynthesis pathway and producing another compound can be decreased or entirely eliminated. Also, enzymes that negatively act on L-amino acid synthesis or accumulation can also be reduced, made deficient, or entirely eliminated.

Examples of such enzymes involved in L-lysine production include homoserine dehydrogenase, lysine decarboxylase (cadA, ldcC), malic enzyme, and so forth, and strains in which activities of these enzymes are decreased or deleted are disclosed in WO95/23864, WO96/17930, WO2005/010175, and so forth.

Expression of both the cadA and ldcC genes encoding lysine decarboxylase can be decreased in order to decrease or delete the lysine decarboxylase activity. Expression of both genes can be decreased by, for example, the method described in WO2006/078039.

In order to reduce or eliminate activities of these enzymes, a mutation can be introduced into the genes encoding the enzymes on the genome by a usual mutagenesis method or gene recombination technique so that intracellular activities of the enzymes are reduced or eliminated. Mutations can be introduced by, for example, using genetic recombination to eliminate the genes coding for the enzymes on the genome, or modifying an expression control sequence such as a promoter or the Shine-Dalgarno (SD) sequence. Also, a mutation causing an amino acid substitution (missense mutation), a stop codon (nonsense mutation), or a frame shift mutation, which results in adding or deleting one or two nucleotides into regions coding for the enzymes on the genome, can be introduced, or the genes can be partially or totally deleted (J. Biol. Chem., 272:8611-8617 (1997)). The enzymatic activities can also be decreased or eliminated by constructing a gene coding for a mutant enzyme in which the coding region is totally or partially deleted, and substituting it for a normal gene on a genome by homologous recombination or the like, or by introducing a transposon or IS factor into the gene.

For example, in order to introduce a mutation that decreases or eliminates the activities of the above-mentioned enzymes by genetic recombination, the following methods can be used. A mutant gene can be prepared by modifying a partial sequence of an objective gene so that it does not encode an enzyme that can function normally, and then a bacterium belonging to the family Enterobacteriaceae can be transformed with a DNA containing the mutant gene to cause recombination of a corresponding gene on the genome with the mutant gene to substitute the mutant gene for the objective gene on the genome. Examples of such gene substitution using homologous recombination include methods of using a linear DNA such as the method called Red-driven integration (Datsenko, K. A, and Wanner, B. L., Proc. Natl. Acad. Sci. USA, 97:6640-6645 (2000)), and the method utilizing the Red-driven integration in combination with an excisive system derived from λ phage (Cho, E. H., Gumport, R. I., Gardner, J. F., J. Bacteriol., 184:5200-5203 (2002)) (refer to WO2005/010175), a method of using a plasmid containing a temperature-sensitive replication origin (U.S. Pat. No. 6,303,383, Japanese Patent Laid-open No. 05-007491), and so forth. Furthermore, such site-specific mutagenesis based on gene substitution using homologous recombination can also be performed by using a plasmid which is not able to replicate in a host.

Examples of bacteria which are able to produce L-lysine include *Escherichia coli* WC196ΔcadAΔldc/pCABD2 (WO2006/078039). This strain was constructed by introducing the plasmid pCABD2 containing the lysine biosynthesis genes (U.S. Pat. No. 6,040,160) into the WC196 strain, in which the cadA and ldcC genes have been disrupted. The WC196 strain was bred from the W3110 strain, which was derived from *Escherichia coli* K-12, by replacing the wild-type lysC gene on the chromosome of the W3110 strain with a mutant lysC gene encoding a mutant aspartokinase III in which the threonine at position 352 was replaced with isoleucine, resulting in desensitization of the feedback inhibition by L-lysine (U.S. Pat. No. 5,661,012), and conferring AEC resistance to the resulting strain (U.S. Pat. No. 5,827,698). The WC196 strain was designated *Escherichia coli* AJ13069, deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994, and assigned an accession number of FERM P-14690. Then, it was converted to an international deposit under the provisions of the Budapest Treaty on Sep. 29, 1995, and assigned an accession number of FERM BP-5252 (U.S. Pat. No. 5,827,698). The WC196ΔcadAΔldc strain itself is an example of an L-lysine-producing bacterium. The WC196ΔcadAΔldc was designated AJ110692, and deposited at the independent administrative agency, National Institute of Advanced Industrial Science and Technology, International Patent Organism Depositary (Tsukuba Central 6, 1-1, Higashi 1-Chome, Tsukuba-shi, Ibaraki-ken, 305-8566, Japan) on Oct. 7, 2008 as an international deposit and assigned an accession number of FERM BP-11027.

The plasmid pCABD2 contains a mutant dapA gene derived from *Escherichia coli* and coding for a dihydrodipicolinate synthase (DDPS) which has a mutation for desensitization to the feedback inhibition by L-lysine, a mutant lysC gene derived from *Escherichia coli* and coding for aspartokinase III having a mutation for desensitization to the feedback inhibition by L-lysine, the dapB gene derived from *Escherichia coli* and coding for dihydrodipicolinate reductase, and the ddh gene derived from *Brevibacterium lactofermentum* and coding for diaminopimelate dehydrogenase (International Publications WO95/16042 and WO01/53459).

The procedures described above for enhancing gene expression of the enzymes involved in the L-lysine biosynthesis, and the methods for reducing the enzymatic activities can similarly be applied to genes coding for other L-amino acid biosynthesis enzymes.

Examples of L-lysine-producing coryneform bacteria include S-(2-aminoethyl)-cysteine (AEC) resistant mutant strains (*Brevibacterium lactofermentum* AJ11082 (NRRL B-11470) strain etc., refer to Japanese Patent Publication Nos. 56-1914, 56-1915, 57-14157, 57-14158, 57-30474, 58-10075, 59-4993, 61-35840, 62-24074, 62-36673, 5-11958, 7-112437 and 7-112438); mutant strains requiring an amino acid such as L-homoserine for their growth (refer to Japanese Patent Publication Nos. 48-28078 and 56-6499); mutant strains showing resistance to AEC and further requiring an amino acid such as L-leucine, L-homoserine, L-proline, L-serine, L-arginine, L-alanine and L-valine (refer to U.S. Pat. Nos. 3,708,395 and 3,825,472); L-lysine-producing mutant strains showing resistance to DL-α-amino-ε-caprolactam, α-amino-lauryllactam, aspartic acid analogue, sulfa drug, quinoid and N-lauroylleucine; L-lysine-producing mutant strains which are resistant to oxaloacetate decarboxylase or a respiratory tract enzyme inhibitor (Japanese Patent Laid-open Nos. 50-53588, 50-31093, 52-102498, 53-9394, 53-86089, 55-9783, 55-9759, 56-32995, 56-39778, Japanese Patent Publication Nos. 53-43591 and 53-1833); L-lysine-producing mutant strains requiring inositol or acetic acid (Japanese Patent Laid-open Nos. 55-9784 and 56-8692); L-lysine-producing mutant strains that are susceptible to fluoropyruvic acid or a temperature of 34° C. or higher (Japanese Patent Laid-open Nos. 55-9783 and 53-86090); L-lysine-producing mutant strains of *Brevibacterium* or *Corynebacterium* bacteria which are resistant to ethylene glycol (U.S. Pat. No. 4,411,997) and so forth.

L-Tryptophan-Producing Bacteria

Examples of bacteria which produce L-tryptophan and parent strains which can be used to derive such bacteria include, but are not limited to, strains belonging to the genus *Escherichia*, such as *E. coli* JP4735/pMU3028 (DSM10122) and JP6015/pMU91 (DSM10123) which are deficient in tryptophanyl-tRNA synthetase encoded by mutant trpS gene (U.S. Pat. No. 5,756,345), *E. coli* SV164 (pGH5) having a serA allele encoding phosphoglycerate dehydrogenase not subject to feedback inhibition by serine and a trpE allele encoding anthranilate synthase not subject to feedback inhibition by tryptophan (U.S. Pat. No. 6,180,373); *E. coli* AGX17 (pGX44) (NRRL B-12263) and AGX6(pGX50)aroP (NRRL B-12264) deficient in the enzyme tryptophanase (U.S. Pat. No. 4,371,614), *E. coli* AGX17/pGX50, pACKG4-pps in which a phosphoenolpyruvate-producing ability is enhanced (WO97/08333, U.S. Pat. No. 6,319,696), and so forth. L-tryptophan-producing bacteria belonging to the genus *Escherichia* which have enhanced activity of the protein encoded by the yedA or yddG gene can also be used (U.S. Patent Published Applications 2003/0148473 A1 and 2003/0157667 A1).

Examples of L-tryptophan-producing bacteria and parent strains which can be used to derive them also include strains in which one or more activities of the following enzymes are enhanced: anthranilate synthase (trpE), phosphoglycerate dehydrogenase (serA), and tryptophan synthase (trpAB). The anthranilate synthase and phosphoglycerate dehydrogenase both are subject to feedback inhibition by L-tryptophan and L-serine, and therefore a mutation desensitizing the feedback inhibition can be introduced into these enzymes. Specific examples of strains having such a mutation include *E. coli* SV164 which harbors desensitized anthranilate synthase and a transformant strain SV164 obtained by introducing into the *E. coli* SV164 the plasmid pGH5, which contains a mutant serA gene encoding a feedback inhibition-desensitized phosphoglycerate dehydrogenase.

Examples of L-tryptophan-producing bacteria and parent strains which can be used to derive them also include a strain which has enhanced activity of 3-phosphoserine phosphatase (serB) (U.S. Pat. No. 4,371,614), a strain which has enhanced activity of phosphoenolpyruvate carboxykinase (pckA) (WO2004/090125), and a strain in which enzymes of the glyoxylic acid pathway are constitutively expressed (WO2005/103275).

L-Tryptophan, L-phenylalanine, and L-tyrosine are all aromatic amino acids and share a common biosynthesis pathway. Examples of the genes encoding the biosynthesis enzymes for these aromatic amino acids include deoxyarabino-heptulosonate phosphate synthase (aroG), 3-dehydroquinate synthase (aroB), shikimic acid dehydratase (aroE), shikimate kinase (aroL), 5-enolpyruvylshikimate-3-phosphate synthase (aroA), and chorismate synthase (aroC) (European Patent Laid-open No. 763127). It is known that these genes are controlled by the tyrosine repressor (tyrR), and so activity of an aromatic amino acid biosynthesis enzyme can also be increased by deleting the tyrR gene (see European Patent Laid-open No. 763127). The abbreviations in parentheses after the enzyme names are the gene names (the same shall apply to the same occasions hereafter).

In order to enhance the productivity of each of the target aromatic amino acids, biosynthesis of an amino acid other than the target amino acid can be attenuated. For example, when the target amino acid is L-tryptophan, biosynthetic pathways of L-phenylalanine and/or L-tyrosine can be attenuated (U.S. Pat. No. 4,371,614).

The phrase "increase of activity of an enzyme" can mean, for example, an increased number of enzyme molecules per cell, increased specific activity per enzyme molecule, and so forth. For example, the activity can be increased by increasing expression of the gene of the enzyme. Intracellular activity of an enzyme can be increased to be higher than that of a non-modified strain, for example, a wild-type strain, of the microorganism.

Furthermore, 3-deoxy-D-arabinoheptulosonate-7-phosphate synthetase (aroF, aroG) is subject to feedback inhibition by aromatic amino acids. Therefore, the enzyme can be modified so that it is not subject to the feedback inhibition. An aromatic L-amino acid-producing bacterium can be obtained, for example, by introducing a mutant aroF in which the L-aspartic acid at position 147 or the L-serine at position 181, as counted from the N-terminus, is replaced by another amino acid, or by introducing a mutant aroG gene in which the L-aspartic acid at position 146, the L-methionine at position 147, the L-proline at position 150 or the L-alanine at position 202, or both the L-methionine at position 157 and the L-alanine at position 219, as counted from the N-terminus, are replaced by other amino acid(s) (European Patent Laid-open No. 0488424).

Examples of L-tryptophan-producing bacteria and parent strains which can be used to derive them also include strains into which the tryptophan operon containing a gene encoding inhibition-desensitized anthranilate synthase has been introduced (Japanese Patent Laid-open Nos. 57-71397, 62-244382, U.S. Pat. No. 4,371,614). Moreover, L-tryptophan-producing ability can be imparted by enhancing expression of a gene which encodes tryptophan synthase in the tryptophan operon (trpBA). Tryptophan synthase consists of α and β subunits which are encoded by the trpA and trpB genes, respectively. In addition, L-tryptophan-producing ability can be improved by enhancing expression of the isocitrate lyase-malate synthase operon (WO2005/103275).

As coryneform bacteria, Corynebacterium glutamicum AJ12118 (FERM BP-478, Japanese Patent No. 01681002), which is resistant to sulfaguanidine, the coryneform bacterium introduced with the tryptophan operon (Japanese Patent Laid-open No. 63-240794), and the coryneform bacterium introduced with a gene coding for shikimate kinase derived from a coryneform bacterium (Japanese Patent Laid-open No. 01-994749) can be used.

L-Phenylalanine-Producing Bacteria

Examples of L-phenylalanine-producing bacteria and parent strains which can be used to derive them include, but are not limited to, strains belonging to the genus Escherichia, such as E. coli AJ12739 (tyrA::Tn10, tyrR) (VKPM B-8197), E. coli HW1089 (ATCC 55371) harboring a mutant pheA34 gene (U.S. Pat. No. 5,354,672), E. coli MWEC101-b (Korean Patent No. 8903681), E. coli NRRL B-12141, NRRL B-12145, NRRL B-12146, and NRRL B-12147 (U.S. Pat. No. 4,407,952). Also, as a parent strain, E. coli K-12 [W3110 (tyrA)/pPHAB (FERM BP-3566), E. coli K-12 [W3110 (tyrA)/pPHAD] (FERM BP-12659), E. coli K-12 [W3110 (tyrA)/pPHATerm] (FERM BP-12662) and E. coli K-12 [W3110 (tyrA)/pBR-aroG4, pACMAB] named as AJ12604 (FERM BP-3579) can be used (European Patent Publication No. 488424 B1). Furthermore, L-phenylalanine-producing bacteria belonging to the genus Escherichia with an enhanced activity of the protein encoded by the yedA gene or the yddG gene can also be used (U.S. Patent Published Applications No. 2003/0148473 A1 and 2003/0157667 A1).

As phenylalanine-producing coryneform bacteria, the Cornebacterium glutamicum BPS-13 (FERM BP-1777), K77 (FERM BP-2062), and K78 (FERM BP-2063) (European Patent Laid-open No. 331145, Japanese Patent Laid-open No. 02-303495), of which phosphoenolpyruvate carboxylase or pyruvate kinase activity is reduced, tyrosine-auxotrophic strain (Japanese Patent Laid-open No. 05-049489), and so forth can be used.

A bacterium which efficiently produces phenylalanine can also be obtained by modifying a bacterium so that it incorporates by-products, for example, by increasing the expression of the L-tryptophan uptake gene, tnaB or mtr, or the L-tyrosine uptake gene, tyrP (European Patent No. 1484410).

L-Tyrosine-Producing Bacteria

Examples of tyrosine-producing bacteria include Escherichia bacteria with a desensitized prephenate dehydratase gene (tyrA) (European Patent Application Laid-open No. 1616940).

L-Valine-Producing Bacteria

Examples of L-valine-producing bacteria and parent strains which can be used to derive L-valine-producing bacteria include, but are not limited to, strains which have been modified to overexpress the ilvGMEDA operon (U.S. Pat. No. 5,998,178). The region in the ilvGMEDA operon which is required for attenuation can be removed so that expression of the operon is not attenuated by the L-valine that is produced. Furthermore, the ilvA gene in the operon can be disrupted so that threonine deaminase activity is decreased.

Examples of L-valine-producing bacteria and parent strains which can be used to derive L-valine-producing bacteria also include mutant strains with amino-acyl t-RNA synthetase having a mutation (U.S. Pat. No. 5,658,766). For example, E. coli VL1970, which has a mutation in the ileS gene encoding isoleucine tRNA synthetase, can be used. E. coli VL1970 was deposited at the Russian National Collection of Industrial Microorganisms (VKPM) (1 Dorozhny proezd., 1 Moscow 117545, Russia) on Jun. 24, 1988 under an accession number VKPM B-4411.

Furthermore, mutants requiring lipoic acid for growth and/or lacking H$^+$-ATPase can also be used as parent strains (WO96/06926).

Examples of L-valine-producing bacteria of coryneform bacteria include, for example, strains modified so that expression of a gene encoding an L-valine biosynthetic enzyme is enhanced. Examples of the L-valine biosynthesis enzyme include enzymes encoded by genes present on the ilvBNC operon, that is, acetohydroxy acid synthetase encoded by ilvBN and isomero-reductase encoded by ilvC (WO00/50624). Since the ilvBNC operon is subject to expression regulation by L-valine and/or L-isoleucine and/or L-leucine, this attenuation can be eliminated to avoid the suppression of expression by the L-valine that is produced.

L-valine-producing ability can be imparted to coryneform bacteria by decreasing or eliminating the activity of at least one kind of enzyme which is involved in a metabolic pathway that decreases L-valine production. For example, decrease of the activity of threonine dehydratase involved in the L-leucine synthesis, or activity of an enzyme that is involved in D-panthothenate synthesis is contemplated (WO00/50624).

Examples of methods for imparting L-valine-producing ability also include imparting resistance to an amino acid analogue or the like.

Examples include mutant strains which are auxotrophic for L-isoleucine and L-methionine, and resistant to D-ribose, purine ribonucleoside or pyrimidine ribonucleoside, and have an ability to produce L-valine (FERM P-1841, FERM P-29, Japanese Patent Publication No. 53-025034), mutant strains resistant to polyketides (FERM P-1763, FERM P-1764, Japanese Patent Publication No. 06-065314), and mutant strains resistant to L-valine in a medium containing acetic acid as the sole carbon source, and sensitive to pyruvic acid analogues (fluoropyruvic acid etc.) in a medium containing glucose as the sole carbon source (FERM BP-3006, BP-3007, Japanese Patent No. 3006929).

An example of a gene involved in the synthesis of branched chain amino acids is the ilvGMEDA operon, and this operon is subject to expression control (attenuation) by L-valine and/or L-isoleucine and/or L-leucine. Therefore, productivity of a microorganism for these L-amino acids can be improved by introducing into the microorganism the ilvGMEDA operon in which the region required for attenuation is removed or mutated.

L-Isoleucine-Producing Bacteria

Examples of L-isoleucine-producing bacteria and parent strains which can be used to derive L-isoleucine-producing bacteria include, but are not limited to, mutants which are resistant to 6-dimethylaminopurine (Japanese Patent Laid-open No. 5-304969), mutants which are resistant to an isoleucine analogue such as thiaisoleucine and isoleucine hydroxamate, and mutants which are additionally resistant to DL-ethionine and/or arginine hydroxamate (Japanese Patent Laid-open No. 5-130882). In addition, recombinant strains transformed with genes encoding proteins involved in L-isoleucine biosynthesis, such as threonine deaminase and acetohydroxy acid synthase, can also be used as parent strains (Japanese Patent Laid-open No. 2-458, French Patent No. 0356739, and U.S. Pat. No. 5,998,178).

Examples of L-isoleucine-producing strains of coryneform bacteria include the coryneform bacterium in which the brnE gene coding for a branched chain amino acid excretion protein is amplified (Japanese Patent Laid-open No. 2001-169788), the coryneform bacterium imparted with L-isoleucine-producing ability by protoplast fusion with an L-lysine-producing bacterium (Japanese Patent Laid-open No. 62-74293), a coryneform bacterium in which homoserine dehydrogenase is enhanced (Japanese Patent Laid-open No. 62-91193), a threonine hydroxamete resistant strain (Japanese Patent Laid-open No 62-195293), an α-ketomalonic acid resistant strain (Japanese Patent Laid-open No. 61-15695), and a methyl lysine resistant strain (Japanese Patent Laid-open No. 61-15696).

L-Leucine-Producing Bacteria

Examples of L-leucine-producing bacteria and parent strains for deriving L-leucine-producing bacteria include, but are not limited to, *Escherichia* bacteria, such as *E. coli* strains resistant to leucine (for example, the strain 57 (VKPM B-7386, U.S. Pat. No. 6,124,121)) or leucine analogues including β-2-thienylalanine, 3-hydroxyleucine, 4-azaleucine and 5,5,5-trifluoroleucine (Japanese Patent Publication No. 62-34397 and Japanese Patent Laid-open No. 8-70879); *E. coli* strains obtained by the genetic engineering method described in WO96/06926; and *E. coli* H-9068 (Japanese Patent Laid-open No. 8-70879).

The bacterium can also be improved by enhancing the expression of one or more genes involved in L-leucine biosynthesis. Examples of such genes include the genes of the leuABCD operon, such as a mutant leuA gene coding for isopropylmalate synthase desensitized to feedback inhibition by L-leucine (U.S. Pat. No. 6,403,342). In addition, the bacterium can be improved by enhancing the expression of one or more genes coding for proteins which excrete L-amino acid from the bacterial cell. Examples of such genes include the b2682 and b2683 genes (ygaZH genes) (European Patent Laid-open No. 1239041 A2).

Examples of L-leucine-producing strains of coryneform bacteria include the 2-thiazolealanine and β-hydroxyleucine-resistant strains (Japanese Patent Laid-open No. 8-266295), the valine analogue-resistant strain (Japanese Patent Laid-open No. 63-248392), the valine auxotrophic strain (Japanese Patent Publication No. 38-4395), the S-(2-aminoethyl)-L-cysteine (AEC) resistant strain (Japanese Patent Publication No. 51-37347), and the phenylalanine, valine and isoleucine auxotrophic strain (Japanese Patent Publication No. 54-36233).

L-Glutamic Acid-Producing Bacteria

Examples of L-glutamic acid-producing bacteria include strains in which expression of a gene encoding an L-glutamic acid biosynthetic enzyme is enhanced. Examples of such genes include, but are not limited to, genes encoding glutamate dehydrogenase (gdhA), glutamine synthetase (glnA), glutamate synthetase (ghAB), isocitrate dehydrogenase (icdA), aconitate hydratase (acnA, acnB), citrate synthase (ghA), phosphoenolpyruvate carboxylase (ppc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), glucose phosphate isomerase (pgi), and so forth.

Examples of strains which have been modified so that expression of the citrate synthetase gene, the phosphoenolpyruvate carboxylase gene, the isocitrate dehydrogenase gene, the pyruvate dehydrogenase gene, and/or the glutamate dehydrogenase gene is enhanced include those disclosed in European Patent Laid-open Nos. 1078989, 955368, 952221 and 1033407.

L-glutamic acid producing ability can be imparted by decreasing or eliminating the activity of an enzyme that catalyzes a reaction branching off from the L-glutamic acid biosynthesis pathway and producing a compound other than L-glutamic acid. Examples of such an enzyme include isocitrate lyase, α-ketoglutarate dehydrogenase, acetohydroxy acid synthase, acetolactate synthase, formate acetyltransferase, lactate dehydrogenase, glutamate decarboxylase, 1-pyrroline-5-carboxilate dehydrogenase, and so forth.

For example, in order to decrease the α-ketoglutarate dehydrogenase activity, a modification can be performed by using the sucA (odhA) gene coding for the E1o subunit of the enzyme. Examples of strains with decreased α-ketoglutarate dehydrogenase activity include, for example, the following strains:

*Brevibacterium lactofermentum* ΔS strain (WO95/34672)
*Brevibacterium lactofermentum* AJ12821 (FERM BP-4172; French Patent No. 9401748)
*Brevibacterium flavum* AJ12822 (FERM BP-4173; French Patent No. 9401748)

*Corynebacterium glutamicum* AJ12823 (FERM BP-4174; French Patent No. 9401748)

*Pantoea ananatis* AJ13601 (FERM BP-7207)
*Klebsiella planticola* AJ13410 (FERM BP-6617)
*Pantoea ananatis* AJ13355 (FERM BP-6614)

*Pantoea ananatis* AJ13356 is deficient in α-ketoglutarate dehydrogenase activity as a result of disruption of the αKGDH-E1 subunit gene (sucA). This strain was identified as *Enterobacter agglomerans* when it was isolated and deposited as the *Enterobacter agglomerans* AJ13356. However, it was recently re-classified as *Pantoea* ananatis on the basis of nucleotide sequencing of 16S rRNA and so forth. Although AJ13356 was deposited at the aforementioned depositary as *Enterobacter agglomerans*, it is described as *Pantoea* ananatis in this specification.

Furthermore, the ability to produce L-glutamic acid in coryneform bacteria can also be achieved by a method of amplifying the yggB gene (NCgl 1221; NP_600492. Reports small-conductance. [gi:19552490], WO2006/070944), and a method of introducing a yggB gene having a mutation in the coding region.

Examples of other methods for imparting or enhancing L-glutamic acid-producing ability include a method of imparting resistance to an organic acid analogue, a respiratory chain inhibitor, etc., and a method of imparting sensitivity to a cell wall synthesis inhibitor. Examples of such methods include imparting resistance to monofluoroacetic acid (Japanese Patent Laid-open No. 50-113209), imparting resistance to adenine or thymine (Japanese Patent Laid-open No. 57-065198), attenuating urease (Japanese Patent Laid-open No. 52-038088), imparting resistance to malonic acid (Japanese Patent Laid-open No. 52-038088), imparting resistance to benzopyrones or naphthoquinones (Japanese Patent Laid-open No. 56-1889), imparting resistance to HOQNO (Japanese Patent Laid-open No. 56-140895), imparting resistance to α-ketomalonic acid (Japanese Patent Laid-open No. 57-2689), imparting resistance to guanidine (Japanese Patent Laid-open No. 56-35981), imparting sensitivity to penicillin (Japanese Patent Laid-open No. 4-88994), and so forth.

Specific examples of such resistant strains include the following strains:

*Brevibacterium flavum* AJ3949 (FERM BP-2632; Japanese Patent Laid-open No. 50-113209)
*Corynebacterium glutamicum* AJ11628 (FERM P-5736; Japanese Patent Laid-open No. 57-065198)
*Brevibacterium flavum* AJ11355 (FERM P-5007; Japanese Patent Laid-open No. 56-1889)
*Corynebacterium glutamicum* AJ11368 (FERM P-5020; Japanese Patent Laid-open No. 56-1889)
*Brevibacterium flavum* AJ11217 (FERM P-4318; Japanese Patent Laid-open No. 57-2689)
*Corynebacterium glutamicum* AJ11218 (FERM P-4319; Japanese Patent Laid-open No. 57-2689)
*Brevibacterium flavum* AJ11564 (FERM BP-5472; Japanese Patent Laid-open No. 56-140895)
*Brevibacterium flavum* AJ11439 (FERM BP-5136; Japanese Patent Laid-open No. 56-35981)
*Corynebacterium glutamicum* H7684 (FERM BP-3004; Japanese Patent Laid-open No. 04-88994)
*Brevibacterium lactofermentum* AJ11426 (FERM P-5123; Japanese Patent Laid-open No. 56-048890)
*Corynebacterium glutamicum* AJ11440 (FERM P-5137; Japanese Patent Laid-open No. 56-048890)
*Brevibacterium lactofermentum* AJ11796 (FERM P-6402; Japanese Patent Laid-open No. 58-158192)

L-Threonine-Producing Bacteria

Examples of L-threonine-producing bacteria include bacteria belonging to the family Enterobacteriaceae in which an activity of L-threonine biosynthesis system enzyme is enhanced. Examples of genes coding for L-threonine biosynthetic enzymes include the aspartokinase III gene (lysC), aspartate semialdehyde dehydrogenase gene (asd), aspartokinase I gene (thrA), homoserine kinase gene (thrB), and threonine synthase gene (thrC) encoded by the thr operon. Two or more kinds of these genes can be introduced. The genes coding for the L-threonine biosynthetic enzymes can be introduced into an Enterobacteriaceae bacterium with decreased threonine decomposition. Examples of the *Escherichia* bacterium with decreased threonine decomposition include, for example, the TDH6 strain which is deficient in threonine dehydrogenase activity (Japanese Patent Laid-open No. 2001-346578), and so forth.

The activities of the L-threonine biosynthetic enzymes are inhibited by the end product L-threonine, and therefore L-threonine biosynthetic enzymes can be modified so as to be desensitized to feedback inhibition by L-threonine when constructing L-threonine producing strains. The above-described thrA, thrB and thrC genes constitute the threonine operon which has an attenuator structure. The expression of the threonine operon is inhibited by isoleucine and threonine in the culture medium and also repressed by attenuation. This attenuation can be eliminated or reduced by removing a leader sequence or attenuator in the attenuation region (Lynn, S. P., Burton, W. S., Donohue, T. J., Gould, R. M., Gumport, R. I., and Gardner, J. F. J., Mol. Biol. 194:59-69 (1987); WO02/26993; WO2005/049808).

The native promoter present in the upstream region of the threonine operon can be replaced by a non-native promoter (WO98/04715), or the threonine operon can be constructed so that expression of the threonine biosynthetic genes is controlled by the repressor and promoter of λ-phage (European Patent No. 0593792). Furthermore, mutant *Escherichia* bacteria that are desensitized to feedback inhibition by L-threonine can be obtained by selecting strains resistant to α-amino-β-hydroxyisovaleric acid (AHV).

The copy number of the feedback-resistant threonine operon can be increased, or the expression of the modified operon can be increased by connecting it to a potent promoter. In addition to amplification using a plasmid, the copy number can be increased by using a transposon, Mu-phage, or the like so that the operon is transferred onto the chromosome.

The gene encoding aspartokinase III (lysC) can be modified so that the enzyme is desensitized to feedback inhibition by L-lysine. Such a modified lysC gene can be obtained by the method described in U.S. Pat. No. 5,932,453.

L-threonine-producing bacteria can also be obtained by enhancing expression of genes involved in the glycolytic pathway, TCA cycle, or respiratory chain, or genes that regulate expression of these genes, or genes involved in sugar uptake, besides the L-threonine biosynthetic enzyme genes. Examples of these genes that are effective for L-threonine production include the transhydrogenase gene (pntAB, European Patent No. 733712), phosphoenolpyruvate carboxylase gene (pepC, WO95/06114), phosphoenolpyruvate synthase gene (pps, European Patent No. 877090), and pyruvate carboxylase gene derived from coryneform bacterium or *Bacillus* bacterium (WO99/18228, European Patent Laid-open No. 1092776).

L-threonine-producing bacteria can also be obtained by enhancing expression of a gene that imparts L-threonine resistance and/or a gene that imparts L-homoserine resistance, or by imparting L-threonine resistance and/or L-homoserine resistance to the host bacterium. Examples of the genes that impart the above-mentioned resistance include the rhtA gene (Res. Microbiol. 154:123-135 (2003)), rhtB gene (European Patent Laid-open No. 0994190), rhtC gene (European Patent Laid-open No. 1013765), yfiK gene, and yeaS gene (European Patent Laid-open No. 1016710). Exemplary methods for imparting L-threonine resistance to a host bacterium include those described in European Patent Laid-open No. 0994190 or WO90/04636.

E. coli VKPM B-3996 (U.S. Pat. No. 5,175,107) is an example of an L-threonine-producing bacterium. The strain VKPM B-3996 was deposited on Nov. 19, 1987 at the Russian National Collection of Industrial Microorganisms (VKPM), GNII Genetika (Russia, 117545 Moscow 1, Dorozhny proezd, 1) under the registration number VKPM B-3996. The VKPM B-3996 strain contains the plasmid pVIC40 (WO90/04636) which was obtained by inserting the threonine biosynthetic genes (threonine operon, thrABC) into a wide host range plasmid vector pAYC32 containing the streptomycin resistance marker (Chistorerdov, A. Y., and Tsygankov, Y. D., Plasmid, 16, 161-167 (1986)). In pVIC40, aspartokinase I-homoserine dehydrogenase I encoded by the thrA gene in the threonine operon is desensitized to feedback inhibition by threonine.

E. coli VKPM B-5318 (refer to European Patent No. 0593792) is another example of an L-threonine-producing bacterium. The VKPM B-5318 strain was deposited in the Russian National Collection of Industrial Microorganisms (VKPM) GNII Genetika on May 3, 1990 under a registration number of VKPM B-5318. The VKPM B-5318 strain is prototrophic with regard to L-isoleucine, and harbors a recombinant plasmid DNA constructed so that the threonine operon, i.e., threonine biosynthesis genes, deficient in the attenuator region, which is an originally contained transcription regulation region, is located downstream from the λ phage-derived temperature-sensitive C1 repressor, PR-promoter, and the gene coding for N-terminal of Cro protein, and the expression of the threonine biosynthesis genes is regulated by the repressor and the promoter derived from λ phage.

L-Arginine-Producing Bacteria

Examples of L-arginine-producing bacteria and parent strains which can be used to derive L-arginine-producing bacteria include, but are not limited to, Escherichia bacterial strains, such as E. coli strain 237 (VKPM B-7925) (U.S. Patent Published Application No. 2002/058315 A1) and its derivative strains harboring mutant N-acetylglutamate synthase (Russian Patent Application No. 2001112869), E. coli strain 382 (VKPM B-7926) (EP 1170358 A1), and an arginine-producing strain transformed with the argA gene encoding N-acetylglutamate synthetase (EP 1170361 A1).

Examples of L-arginine-producing bacteria and parent strains which can be used to derive L-arginine-producing bacteria also include strains in which the expression of one or more genes encoding an L-arginine biosynthetic enzyme is enhanced. Examples of such genes include the N-acetylglutamyl phosphate reductase gene (argC), ornithine acetyl transferase gene (argJ), N-acetylglutamate kinase gene (argB), acetylornithine transaminase gene (argD), ornithine carbamoyl transferase gene (argF), argininosuccinic acid synthetase gene (argG), argininosuccinic acid lyase gene (argH), and carbamoyl phosphate synthetase gene (carAB).

L-Histidine-Producing Bacteria

Examples of L-histidine-producing bacteria and parent strains which can be used to derive L-histidine-producing bacteria include, but are not limited to, Escherichia bacterial strains, such as E. coli strain 24 (VKPM B-5945, RU2003677), E. coli strain 80 (VKPM B-7270, RU2119536), E. coli NRRL B-12116-B 12121 (U.S. Pat. No. 4,388,405), E. coli H-9342 (FERM BP-6675), E. coli H-9343 (FERM BP-6676) (U.S. Pat. No. 6,344,347), E. coli H-9341 (FERM BP-6674) (EP 1085087 A), E. coli AI80/pFM201 (U.S. Pat. No. 6,258,554), and so forth.

Examples of L-histidine-producing bacteria and parent strains which can be used to derive L-histidine-producing bacteria also include strains in which the expression of one or more genes encoding L-histidine biosynthetic enzymes are enhanced. Examples of such genes include the genes encoding ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the L-histidine biosynthetic enzymes encoded by hisG and hisBHAFI are inhibited by L-histidine, and therefore the ability to produce L-histidine can also be efficiently enhanced by introducing a mutation which confers resistance to feedback inhibition into the gene coding for ATP phosphoribosyltransferase (hisG) (Russian Patent Nos. 2003677 and 2119536).

Specific examples of strains which are able to produce L-histidine include E. coli FERM-P 5038 and 5048 which have been transformed with a vector carrying a DNA encoding an L-histidine biosynthetic enzyme (Japanese Patent Laid-open No. 56-005099), E. coli strains transformed with a gene encoding a protein involved in amino acid export (EP 1016710 A), E. coli 80 strain which is resistant to sulfaguanidine, DL-1,2,4-triazole-3-alanine, and streptomycin (VKPM B-7270, Russian Patent No. 2119536), and so forth.

L-Cysteine-Producing Bacteria

Examples of L-cysteine-producing bacteria include, but are not limited to, strains belonging to the genus Escherichia, such as E. coli JM15 which is transformed with different cysE alleles encoding feedback-resistant serine acetyltransferases (U.S. Pat. No. 6,218,168, Russian Patent Application No. 2003121601), E. coli W3110 with overexpressed genes which encode proteins which promote excretion of substances toxic to cells (U.S. Pat. No. 5,972,663), E. coli strains with reduced cysteine desulfohydrase activity (Japanese Patent Laid-open No. 11-155571), E. coli W3110 with increased activity of a positive transcriptional regulator for cysteine regulon encoded by the cysB gene (WO01/27307A1), and so forth.

L-Serine-Producing Bacteria

Examples of parent strains which can be used to derive L-serine-producing bacteria include coryneform bacteria in which the phosphoserine phosphatase gene is amplified (Japanese Patent Laid-open Nos. 2001-275689 and 11-253187), coryneform bacteria having D-3-phosphoglycerate dehydrogenase desensitized to inhibition, which is derived from coryneform bacteria having L-serine-producing ability and resistant to azaserine or β-(2-thienyl)-DL-alanine (Japanese Patent Laid-open No. 11-266881), and serine-producing coryneform bacteria resistant to azaserine or thienylalanine, and deficient in serine decomposition ability (Japanese Patent Laid-open No. 10-248588).

Asparagine-Producing Bacteria

L-Asparagine is produced by transferring an amino group to aspartic acid (Boehlein, S. K., Richards, N. G. J., & Schuster, S. M. (1994a), J. Biol. Chem., 269, 7450-7457). Therefore, examples of L-asparagine-producing bacteria belonging to the genus *Escherichia* include L-asparatic acid-producing *Escherichia coli* strains in which asparagine synthetase is enhanced.

Methods for imparting the ability to produce nucleic acids to a microorganism and nucleic acid-producing bacteria will be exemplified below.

A bacterium having an ability to produce a nucleic acid can be obtained by imparting, for example, purine nucleoside auxotrophy or resistance to a drug such as purine analogue to such bacteria as described above (Japanese Patent Publication Nos. 38-23099, 54-17033, 55-45199, 57-14160, 57-41915 and 59-42895). For example, a *Bacillus* bacterium having auxotrophy or drug resistance can be obtained by treating the bacterium with a mutatgen which is used in typical mutagenesis treatments such as N-methyl-N'-nitro-N-nitrosoguanidine (NTG) or EMS (ethyl methanesulfonate).

Examples of *Bacillus* bacteria which produce a purine nucleoside include the following.

As a specific example of inosine-producing strain belonging to the genus *Bacillus*, the *Bacillus subtilis* KMBS16 strain can be used. This strain is derived from the known *Bacillus subtilis* trpC2 strain (168 Marburg), wherein the purR gene encoding the purine operon repressor (purR::spc), the purA gene encoding succinyl-AMP synthase (purA::erm), and the deoD gene encoding purine nucleoside phosphorylase (deoD::kan) are disrupted (Japanese Patent Laid-open No. 2004-242610, U.S. Patent Published Application No. 2004166575 A1). The *Bacillus subtilis* AJ3772 strain (FERM P-2555, Japanese Patent Laid-open No. 62-014794) and so forth can also be used.

Examples of *Bacillus* bacteria having an ability to produce guanosine include the *Bacillus* bacterium which has increased IMP dehydrogenase activity (Japanese Patent Laid-open No. 3-58787), *Bacillus* bacterium which is obtained by introducing a vector which includes a gene which confers resistance to purine analogues or decoyinine into an adenine auxotrophic mutant (Japanese Patent Publication No. 4-28357), and so forth.

Examples of *Bacillus* bacteria which produce a purine nucleotide include the following.

As inosinic acid-producing *Bacillus* bacteria, inosine-producing strains of *Bacillus subtilis* which have attenuated phosphatase activity have been reported (Uchida, K. et al., Agr. Biol. Chem., 1961, 25, 804-805; Fujimoto, M., Uchida, K., Agr. Biol. Chem., 1965, 29, 249-259). Examples of guanylic acid-producing bacteria include mutants of *Bacillus* bacteria which have adenine auxotrophy, resistance to decoyinine or methionine sulfoxide and an ability to produce 5'-guanylic acid (guanosine-5'-monophosphate, henceforth also referred to as "GMP") (Japanese Patent Publication No. 56-12438).

Furthermore, a xanthylic acid-producing bacterium can be constructed by the method used to breed coryneform bacteria, a typical example of which is *Corynebacterium ammoniagenes*. For example, by obtaining a PRPP amidotransferase-enhanced strain (Japanese Patent Laid-open No. 8-168383), an aliphatic amino acid-resistant strain (Japanese Patent Laid-open No. 4-262790), or a dehydroproline-resistant strain (South Korean Patent Unexamined Publication No. 2003-56490), a xanthylic acid-producing bacterium can be constructed.

Moreover, exemplary methods for breeding *Bacillus* bacteria which have an ability to produce a purine-derived substance also include enhancing the activity of an enzyme which is involved in purine biosynthesis which is common to the biosynthesis of purine nucleosides and purine nucleotides, i.e., purine biosynthesis enzyme, in bacterial cells.

Examples of an enzyme involved in purine biosynthesis include, for example, phosphoribosyl pyrophosphate amidotransferase, phosphoribosyl pyrophosphate synthetase (PRPP synthetase [EC: 2.7.6.1]), and so forth.

Some of the catabolites produced by metabolism of sugar sources such as glucose that flow into the pentose phosphate pathway are converted into ribose-5-phosphate via ribulose-5-phosphate. From the biosynthesized ribose-5-phosphate, phosphoribosyl pyrophosphate (PRPP) is produced, which is an indispensable precursor for purine nucleoside, histidine and tryptophan biosyntheses. Specifically, ribose-5-phosphate is converted into PRPP by phosphoribosyl pyrophosphate synthetase. Therefore, an ability to produce purine-derived substance can be imparted to a *Bacillus* bacterium or the ability of the bacterium can be enhanced by modifying the bacterium so that the activity of phosphoribosyl pyrophosphate synthetase is increased.

The activity of the phosphoribosyl pyrophosphate synthetase can be measured by, for example, the method of Switzer et al. (Methods Enzymol., 1978, 51, 3-11) or Roth et al. (Methods Enzymol., 1978, 51, 12-17). A *Bacillus* bacterium in which the activity of phosphoribosyl pyrophosphate synthetase is increased can be produced by, for example, increasing expression of a gene encoding the phosphoribosyl pyrophosphate synthetase in a *Bacillus* bacterium according to a method of using a plasmid or integrating the gene into a chromosome, which can be performed in the same manner as that of the method described in Japanese Patent Laid-open No. 2004-242610.

On the other hand, when PRPP, which is an indispensable precursor for purine nucleoside, histidine and tryptophan biosyntheses, is produced, some of it is converted into purine nucleotides and purine nucleosides by the enzymes involved in the purine biosynthesis. Examples of genes encoding for such enzymes include the genes of the purine operon from *Bacillus subtilis*, specifically, genes of the purEKB-purC(orf)QLF-purMNH(J)-purD operon (Ebbole D. J. and Zalkin H., J. Biol. Chem., 1987, 262, 17, 8274-87) (also called purEKBC-SQLFMNHD, *Bacillus subtilis* and Its Closest Relatives, Editor in Chief: A. L. Sonenshein, ASM Press, Washington D.C., 2002, Genbank Accession No. NC_000964), and the genes of the pur regulon from *Escherichia coli* (*Escherichia* and *Salmonella*, Second Edition, Editor in Chief: F. C. Neidhardt, ASM Press, Washington D.C., 1996).

Accordingly, by enhancing expression of these genes, an ability to produce a purine-derived substance can be imparted or enhanced. In addition, genes of the purine operon are not limited to these, and genes derived from other microorganisms, animals and plants can also be used.

Examples of the method for increasing expression of the purine operon include increasing expression of genes of the purine operon in a *Bacillus* bacterium by a method of using a plasmid, integrating the genes into a chromosome, or the like.

The second method for increasing expression of the purine operon includes replacing a native promoter of the purine operon with a stronger promoter, and replacing the −35 or −10 region of the native promoter with a consensus sequence.

For example, in *Bacillus subtilis* (*B. subtilis* 168 Marburg strain, ATCC 6051), the −35 sequence of the purine operon is a consensus sequence (TTGACA), but the −10 sequence is TAAGAT, which differs from the consensus sequence TATAAT (Ebbole, D. J. and H. Zalikn, J. Biol. Chem., 1987, 262, 8274-8287). Therefore, by replacing the −10 sequence (TAAGAT) with the consensus sequence, by approximating the −10 sequence (TAAGAT) close to the consensus sequence, or changing it to TATAAT, TATGAT or TAAAAT, the transcriptional activity of the purine operon can be increased. A promoter sequence can be replaced by the same method as that of the gene substitution, which is described below.

The third method for increasing expression of the purine operon includes decreasing expression of the purine operon repressor (U.S. Pat. No. 6,284,495). Expression of the purine operon repressor (purine repressor) can be decreased by, for example, a method of treating a *Bacillus* bacterium with ultraviolet ray irradiation or mutagen used in a usual mutagenesis treatment such as NTG or EMS, and selecting a mutant showing decreased expression of the purine repressor.

Furthermore, a *Bacillus* bacterium with decreased expression of the purine repressor can also be obtained by, for example, besides a mutagenesis treatment, replacing a gene encoding the purine repressor on a chromosome (purR, GenBank Accession NC_000964) with a corresponding gene that does not normally function (hereafter, also referred to as "disrupted-type gene") by homologous recombination utilizing a gene recombination technique (Experiments in Molecular Genetics, Cold Spring Harbor Laboratory Press (1972); Matsuyama, S, and Mizushima, S., J. Bacteriol., 1985, 162, 1196-1202).

Furthermore, an ability to produce a purine-derived substance can also be enhanced by attenuating the uptake of purine-derived substances into cells. For example, the uptake of purine nucleosides by the cells can be attenuated by blocking a reaction involved in the uptake of purine nucleosides by the cells. Examples of the reaction involved in the uptake of purine nucleosides by the cells include reactions catalyzed by nucleoside permeases.

Furthermore, when a purine nucleoside is produced, activity of an enzyme which decomposes purine-derived substances can be decreased in order to enhance the ability to produce purine nucleoside. Examples of such an enzyme include purine nucleoside phosphorylase.

Purine nucleotides biosynthesized from PRPP by enzymes involved in purine biosynthesis are dephosphorylated and thereby converted into a purine nucleoside. To efficiently produce a purine nucleoside, an activity of purine nucleoside phosphorylases, which further degrade purine nucleosides into hypoxanthine or the like, can be decreased. That is, an activity of a purine nucleoside phosphorylase that employs purine nucleosides such as inosine, as a substrate, can be attenuated or eliminated.

Specifically, the purine nucleoside phosphorylase activity can be decreased by disrupting the deoD and pupG genes encoding purine nucleoside phosphorylase in *Bacillus* bacteria. The *Bacillus* bacterium can be modified by disrupting one or both of the deoD and pupG genes. As the deoD and pupG genes, for example, those genes derived from *Bacillus* bacteria (deoD; Genbank Accession No. NC_000964, pupG; Genbank Accession No. NC_000964) can be used.

The ability to produce a purine-derived substance can also be enhanced by decreasing the activity of succinyl-AMP synthase. Examples of the gene encoding succinyl-AMP synthase include the purA gene. Examples of the purA gene include, for example, those having the nucleotide sequence registered as GenBank Accession No. NC_000964 (coding region corresponds to the nucleotide numbers 4153460 to 4155749 of the complementary strand).

The ability to produce a purine-derived substance can also be enhanced by decreasing the activity of inosine monophosphate (IMP) dehydrogenase. Examples of the gene encoding IMP dehydrogenase include the guaB gene. Examples of the guaB gene include, for example, the gene having the nucleotide sequence registered as GenBank Accession No. NC_000964 (coding region corresponds to the nucleotide numbers 15913 to 17376).

Moreover, as a method for enhancing an ability to produce purine-derived substance, amplification of a gene encoding a protein having an activity of excreting a purine-derived substance can be used. An example of a bacterium in which such a gene is amplified is a *Bacillus* bacterium in which the rhtA gene is amplified (Japanese Patent Laid-open No. 2003-219876).

Furthermore, L-amino acid-producing bacteria, nucleic acid-producing bacteria, and microorganisms used for the breeding thereof, and methods for imparting or enhancing an L-amino acid-producing ability or nucleic acid-producing ability are described in detail in WO2007/125954, WO2005/095627, U.S. Patent Published Application No. 2004/0166575, and so forth.

Furthermore, the above-described methods can be employed in the production of any substance which can be produced by fermentation using a microorganism, and are not limited to production of the aforementioned L-amino acids and nucleic acids.

Furthermore, in the microorganism, according to the target substance, activity of a protein involved in the production of the target substance can be enhanced, and activity of a protein involved in the decomposition of the target substance can be reduced.

Methods for imparting the isomaltase activity to a microorganism or for increasing the isomaltase activity of a microorganism will be explained below. Since some kinds of isomaltase also have maltase activity, maltase activity can be imparted or increased when the isomaltase activity is imparted or increased.

When the microorganism does not contain a native isomaltase activity, the isomaltase activity can be imparted to the microorganism by introducing an isomaltase gene into the microorganism. Furthermore, when the microorganism has isomaltase activity, by introducing a foreign isomaltase gene, increasing copy number of the endogenous isomaltase gene, or modifying an expression control sequence such as a promoter of the isomaltase gene to increase expression of the gene, the isomaltase activity can be increased. The phrase "introduce an isomaltase gene" can mean not only to introduce an isomaltase gene into a microorganism which does not have native or endogenous isomaltase activity, but can also mean to introduce an exogenous isomaltase gene into a microorganism which has native or endogenous isomaltase activity, and to introduce an endogenous isomaltase gene into a microorganism which has the native or endogenous isomaltase activity, thereby increasing the expression amount of the endogenous isomaltase gene.

In order to introduce an isomaltase gene, for example, an isomaltase gene can be cloned into an appropriate vector, and a host microorganism is transformed with the obtained vector.

Examples of the vector used for transformation include a plasmid which can autonomously replicate in a chosen microorganism. Examples of plasmids autonomously replicable in a microorganism belonging to the family Enterobacteriaceae include pUC19, pUC18, pBR322, RSF1010, pHSG299, pHSG298, pHSG399, pHSG398, pSTV28, pSTV29, pTWV228, pTWV229 (pHSG, pSTV and pTWV series vectors are available from Takara Bio), pMW119, pMW118, pMW219, pMW218 (pMW series vectors are available from Nippon Gene), and so forth. Furthermore, plasmids for coryneform bacteria include pAM330 (Japanese Patent Laid-open No. 58-67699), pHM1519 (Japanese Patent Laid-open No. 58-77895), pSFK6 (Japanese Patent Laid-open No.

2000-262288), pVK7 (U.S. Patent Published Application No. 2003/0175912), pAJ655, pAJ611, pAJ1844 (Japanese Patent Laid-open No. 58-192900), pCG1 (Japanese Patent Laid-open No. 57-134500), pCG2 (Japanese Patent Laid-open No. 58-35197), pCG4, pCG11 (Japanese Patent Laid-open No. 57-183799), pHK4 (Japanese Patent Laid-open No. 5-7491), and so forth.

Examples of transformation methods include treating recipient cells with calcium chloride to increase permeability for DNA, which has been reported for *Escherichia coli* K-12 (Mandel, M. and Higa, A., J. Mol. Biol., 1970, 53:159-162), preparing competent cells from cells which are at the growth phase, followed by transformation with DNA, which has been reported for *Bacillus subtilis* (Duncan, C. H., Wilson, G. A. and Young, F. E., 1977, Gene, 1:153-167), and so forth. Alternatively, a method of making DNA-recipient cells into protoplasts or spheroplasts, which can easily take up recombinant DNA, followed by introducing a recombinant DNA into the cells, which is known to be applicable to *Bacillus subtilis*, actinomycetes and yeasts (Chang, S, and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Sci., USA, 75:1929-1933) can also be employed. In addition, transformation of microorganisms can also be performed by the electric pulse method (Japanese Patent Laid-open No. 2-207791).

The isomaltase gene can also be introduced into the chromosome of the host microorganism by randomly introducing it into a chromosome using a transposon or Mini-Mu (Japanese Patent Laid-open No. 2-109985, U.S. Pat. No. 5,882,888, EP 805867 B1), or by homologous recombination using a sequence present on a chromosomal DNA in a multiple copy numbers as a target. As a sequence present on a chromosomal DNA in a multiple copy numbers, repetitive DNA, and inverted repeats located at the end of a transposable element can be used. Alternatively, by using the Red-driven integration method (WO2005/010175), it is also possible to introduce an objective gene into a chromosome. Moreover, an objective gene can also be introduced into a chromosome by transduction using phages such as P1 phage, or by using a conjugative transfer vector. Furthermore, it is also possible to introduce the isomaltase gene using a gene which is unnecessary for production of an objective substance as a target, as described in WO03/040373. One or more copies of the isomaltase gene can be introduced into a target sequence by such methods.

Transfer of an objective gene onto a chromosome can be confirmed by Southern hybridization using a probe having a sequence complementary to the objective gene or a part thereof.

Although it is sufficient that the gene coding for isomaltase is amplified to more than one copy, it can be amplified to 2 or more copies, 3 or more copies, or even 5 or more copies. When an exogenous gene is introduced into the host microorganism, although it is sufficient that 1 or more copies are introduced, 2 or more copies, 3 or more copies, or even 5 or more copies can be introduced.

Furthermore, the activity of isomaltase can be optimized by substituting or mutating an expression control sequence such as a promoter of the isomaltase gene.

Examples of methods for increasing expression of the isomaltase gene include replacing an expression control sequence such as a promoter of the isomaltase gene with one having an appropriate strength on a chromosomal DNA or a plasmid to enhance expression of the gene. For example, the thr promoter, lac promoter, trp promoter, trc promoter, pL promoter, tac promoter, and so forth are known as strong promoters. Furthermore, variants of the tac promoter used in the examples described below (PtacA promoter, PtacB promoter) can also be used. Methods for evaluating the strength of promoters and strong promoters are described in the paper of Goldstein and Doi (Goldstein, M. A. and Doi R. H., 1995, Prokaryotic promoters in biotechnology, Biotechnol. Annu. Rev., 1, 105-128), and so forth.

Furthermore, it is also possible to introduce a nucleotide substitution for several nucleotides into a promoter region of a gene to modify it into a promoter having an appropriate strength, as disclosed in International Publication WO00/18935. Substitution of the expression control sequence can be performed in the same manner as, for example, that of the gene substitution using a temperature-sensitive plasmid. Examples of vectors having a temperature-sensitive replication origin and usable for *Escherichia coli* and *Pantoea ananatis* include, for example, the temperature-sensitive plasmid pMAN997 described in International Publication WO99/03988, derivatives thereof, and so forth. Furthermore, substitution of an expression control sequence can also be performed by a method utilizing a linear DNA such as the method called "Red-driven integration" using Red recombinase of λ phage (Datsenko, K. A. and Wanner, B. L., 2000, Proc. Natl. Acad. Sci. USA. 97:6640-6645), and the method combining the Red-driven integration method and the λ phage excision system (Cho, E. H., et al., J. Bacteriol., 184: 5200-5203 (2002)) (refer to WO2005/010175). Modification of an expression control sequence can be combined with increasing the copy number of gene.

Furthermore, it is known that substitution of several nucleotides in the spacer between the ribosome binding site (RBS) and translation initiation codon, especially a sequence immediately upstream from the initiation codon, greatly affects mRNA translation efficiency, and therefore this sequence can be modified to improve translation.

When an objective gene is introduced into the aforementioned amplification plasmid or chromosome, any promoter can be used to express the gene so long as the chosen promoter functions in the chosen microorganism. The promoter can be the native promoter for the gene, or a modified promoter. Expression of a gene can also be controlled by suitably choosing a promoter that is strong in the chosen microorganism, or by making the −35 and −10 regions of the promoter closer to the consensus sequence.

Isomaltase can be present in the cytoplasm of the cell, or in the cell wall or cell surface layer such as the periplasm or it can be extracellular. Isomaltase that is present in the cells can be referred to as "intracellular isomaltase," and the activity of the intracellular isomaltase can be referred to as "intracellular activity". Furthermore, the isomaltase which is present in the cytoplasm, and isomaltase which is present in a cell wall or a cell surface layer such as periplasm, or present extracellulary, is generically referred to as "extracellular isomaltase," and the activity of the extracellular isomaltase is referred to as "extracellular activity". The extracellular isomaltase typically exists in a cell surface layer. Furthermore, the phrase "to express extracellular isomaltase" can mean to allow an extracellular isomaltase prepared on the basis of the information of an extracellular isomaltase gene to exist in a cell surface layer or outside of the cell.

Whether the isomaltase activity is enhanced can be confirmed by comparing the isomaltase activities of the modified strain with a parent or non-modified strain. If the isomaltase activity of the modified strain is increased as compared with the parent or non-modified strain, the isomaltase activity is enhanced. Furthermore, when the parent strain does not have isomaltase activity, and if the isomaltase activity can be detected in the modified strain, the isomaltase activity is enhanced. Furthermore, the isomaltase activity can be increased to such an extent that growth is not inhibited. The phrase "not inhibit growth" can mean that the modified strain has a growth rate corresponding to 80% or more, 90% or more, or even 95% or more, of the growth rate of the parent or non-modified strain. Examples of the parent strain include the *Escherichia coli* MG 1655 strain (ATCC No. 47076) and W3110 strain (ATCC No. 27325), *Corynebacterium glutamicum* ATCC 13869 and ATCC 13032, and so forth.

By imparting or enhancing the extracellular isomaltase activity, the ability to assimilate isomaltose can be imparted to a microorganism, or the ability to assimilate isomaltose can be increased. When the microorganism does not have isomaltase activity, by imparting the extracellular isomaltase activity, or imparting the intracellular isomaltase activity and activity to take up isomaltose, the ability to assimilate isomaltose can be increased. When the microorganism has isomaltase activity, by improving the extracellular isomaltase activity, and/or improving the intracellular isomaltase activity and enhancing activity to take up isomaltose, the ability to assimilate isomaltose can be improved. Furthermore, when the microorganism has the activity to take up isomaltose into cells, activity of the intracellular isomaltase or the extracellular isomaltase can be imparted or enhanced. Furthermore, when the microorganism has intracellular isomaltase activity, by enhancing the activity to take up isomaltose into cells, the ability to assimilate isomaltose can also be increased. When the microorganism does not have the activity to take up isomaltose into cells, both the intracellular isomaltase activity and the activity to take up isomaltose into cells can be imparted. When the microorganism has both the intracellular isomaltase activity and the activity to take up isomaltose into cells, the ability to assimilate isomaltose can be improved by enhancing either one or both of the isomaltase activity and the activity to take up isomaltase.

Examples of the isomaltase gene include the isomaltase gene of *Bacillus* bacteria, more specifically, for example, the malL gene (yvdL gene) of *Bacillus subtilis* (BG12421: Genbank Accession No. NP_391336.1), and the glvA gene (malA gene) of *Bacillus subtilis* (BG11839: Genbank Accession No. NP_388699.1). The nucleotide sequence of the malL gene, and the amino acid sequence of isomaltase encoded by the gene are shown in SEQ ID NOS: 13 and 14, respectively. The nucleotide sequence of the glvA gene, and the amino acid sequence of isomaltase encoded by the gene are shown in SEQ ID NOS: 39 and 40, respectively. If these genes are expressed in a microorganism, intracellular isomaltase is produced. The isomaltase encoded by the glvA gene of *Bacillus subtilis* also has the maltase activity in addition to the isomaltase activity. Therefore, if this gene or a homologue thereof is expressed in a microorganism, a protein having both the isomaltase activity and the maltase activity is expressed. When isomaltose and maltose are present as the carbon source in the medium, such a gene coding for an isomaltase having both the isomaltase activity and the maltase activity can be used. In addition, when the maltase activity is imparted or increased in addition to the isomaltase activity, the glvA gene or a homologue thereof can be used as described above, and both the isomaltase gene and a gene coding for a maltase not having the isomaltase activity can be used. Such a gene coding for an isomaltase having both the isomaltase activity and the maltase activity can be used.

The isomaltase gene can also be obtained by PCR using oligonucleotides prepared on the basis of the aforementioned sequence information or sequence information of gene or protein known for the microorganism as primers, or hybridization using an oligonucleotide prepared on the basis of the aforementioned sequence information as a probe, from a chromosomal DNA or chromosomal DNA library of a *Bacillus* bacterium. When a gene of a *Bacillus* bacterium is used, examples of the *Bacillus* bacterium include *Bacillus subtilis, Bacillus amyloliquefaciens, Bacillus pumilus*, and so forth. Examples of *Bacillus subtilis* include the *Bacillus subtilis* 168 Marburg (ATCC 6051), *Bacillus subtilis* PY79 (Plasmid, 1984, 12, 1-9), and so forth, and examples of *Bacillus amyloliquefaciens* include the *Bacillus amyloliquefaciens* T (ATCC 23842), the *Bacillus amyloliquefaciens* N (ATCC 23845), and so forth. Furthermore, examples of *Bacillus pumilus* include *Bacillus pumilus* Gottheil No. 3218 (ATCC No. 21005, U.S. Pat. No. 3,616,206), and so forth.

Genes coding for isomaltase derived from other microorganisms, for example, homologues of the malL gene, are shown in the following Table.

TABLE 1

| No. | Gene | Bacterium | Function |
|---|---|---|---|
| 1 | ACE77085 | *Bacillus* sp. ZW2531-1 | oligosaccharide-producing multifunctional G-amylase |
| 2 | YP_077891 | *Bacillus licheniformis* ATCC 14580 | glycoside hydrolase family protein |
| 3 | AAG23399 | *Bacillus subtilis* | oligo-1,6-glucosidase |
| 4 | P29093 | *Bacillus* sp. F5 | oligo-1,6-glucosidase |
| 5 | ZP_01695723 | *Bacillus coagulans* 36D1 | alpha amylase, catalytic region |
| 6 | Q45101 | *Bacillus coagulans* | oligo-1,6-glucosidase |
| 7 | P29094 | *Geobacillus thermoglucosidasius* | oligo-1,6-glucosidase |
| 8 | ZP_02914561 | *Geobacillus* sp. WCH70 | alpha amylase catalytic region |
| 9 | YP_001375945 | *Bacillus cereus* subsp. *Cytotoxis* NVH 391-98 | alpha amylase catalytic region |
| 10 | YP_896374 | *Bacillus thuringiensis* str. A1 Hakam | oligo-1,6-glucosidase |
| 11 | P21332 | *Bacillus cereus* | oligo-1,6-glucosidase |
| 12 | ZP_02583217 | *Bacillus cereus* G9842 | oligo-1,6-glucosidase |
| 13 | ZP_03102374 | *Bacillus cereus* W | oligo-1,6-glucosidase |
| 14 | YP_001884389 | *Clostridium botulinum* B str. Eklund 17B | oligo-1,6-glucosidase |
| 15 | YP_001919572 | *Clostridium botulinum* E3 str. Alaska E43 | oligo-1,6-glucosidase |
| 16 | BAE45038. | *Geobacillus stearothermophilus* | trehalose-6-phosphate hydrolase |
| 17 | NP_463715 | *Listeria monocytogenes* EGD-e | hypothetical protein lmo0184 |
| 18 | YP_001307875. | *Clostridium beijerinckii* NCIMB 8052 | alpha amylase, catalytic region |
| 19 | YP_147599 | *Geobacillus kaustophilus* HTA426 | alpha,alpha-phosphotrehalase |

TABLE 1-continued

| No. | Gene | Bacterium | Function |
|---|---|---|---|
| 20 | NP_693477 | Oceanobacillus iheyensis HTE831 | oligo-1,6-glucosidase |
| 21 | YP_796261 | Lactobacillus brevis ATCC 367 | trehalose-6-phosphate hydrolase |
| 22 | YP_001843555 | Lactobacillus fermentum IFO 3956 | alpha-glucosidase |
| 23 | ZP_01114415 | Reinekea sp. MED297 | oligo-1,6-glucosidase |

Genes coding for isomaltase derived from other microorganisms, for example, homologues of the glvA gene, are shown in the following Table.

TABLE 2

| No. | Gene | Bacterium | Function |
|---|---|---|---|
| 1 | RBAM_008360 | Bacillus amyloliquefaciens FZB42 | maltose-6'-phosphate glucosidase |
| 2 | BLi00855 | Bacillus licheniformis ATCC 14580 | maltose-6'-phosphate glucosidase |
| 3 | CLD_0473 | Clostridium botulinum B1 str. Okra | maltose-6'-phosphate glucosidase |
| 4 | CLK_3465 | Clostridium botulinum A3 str. Loch Maree (strain: Loch Maree) | maltose-6'-phosphate glucosidase |
| 5 | CLI_0351 | Clostridium botulinum F str. Langeland (strain: Langeland) | maltose-6'-phosphate glucosidase |
| 6 | CLC_0337 | Clostridium botulinum A str. Hall (strain: Hall) | maltose-6'-phosphate glucosidase |
| 7 | CBO0278 | Clostridium botulinum A str. ATCC 3502 | maltose-6'-phosphate glucosidase |
| 8 | CAC0533 | Clostridium acetobutylicum ATCC 824 | maltose-6'-phosphate glucosidase |
| 9 | ECA1847 | Pectobacterium atrosepticum SCRI1043 | 6-phospho-alpha-glucosidase |
| 10 | ESA_03956 eta | Enterobacter sakazakii ATCC BAA-894 | maltose-6'-phosphate glucosidase |
| 11 | EcHS_A3893 ecmecfece: | Escherichia coli HS | 6-phospho-alpha-glucosidase |
| 12 | SDY_4168 | Shigella dysenteriae Sd197 | maltose-6'-phosphate glucosidase |

The gene coding for isomaltase can also be obtained by PCR using oligonucleotides prepared on the basis of the aforementioned sequence information or sequence information of gene or protein known for the microorganism as primers, or hybridization using an oligonucleotide prepared on the basis of the aforementioned sequence information as a probe from a chromosomal DNA or chromosomal DNA library of a microorganism. A chromosomal DNA can be prepared from a microorganism that serves as a DNA source by the method of Saito and Miura (refer to Saito H. and Miura K. I., 1963, Biochem. Biophys. Acta, 72, 619; Experimental Manual for Biotechnology, edited by The Society for Biotechnology, Japan, pp. 97-98, Baifukan Co., Ltd., 1992) or the like.

The malL and glvA gene homologues can mean natural mutant genes derived from other Bacillus bacteria or other microorganisms, or artificial mutant genes, which show high structural similarity to the malL or glvA gene described above, and code for a protein having the isomaltase activity. Homologues of the malL gene mean those coding for a protein having a homology of 80% or more, 90% or more, 95% or more, 98% or more, or even 99% or more, to the total amino acid sequence of SEQ ID NO: 14 or 40, and having the isomaltase activity. Whether a protein has isomaltase activity or not can be confirmed by expressing the gene in a host cell, and examining the isomaltase activity by, for example, the aforementioned method. In this specification, the term "homology" can also be used to refer to "identity". The above descriptions concerning homology of the aforementioned homologues are similarly applied to the other genes.

Furthermore, the malL and glvA genes are not limited to the wild-type genes, but can be variants of the genes, i.e., mutant or artificially modified genes coding for the amino acid sequence of SEQ ID NO: 14 or 40, but which include substitutions, deletions, insertions, additions or the like of one or several amino acid residues at one or several positions, so long as the isomaltase activity of the encoded protein is not impaired.

Although the number of the "one or several" amino acid residues referred to herein can differ depending on the position in the three-dimensional structure of the protein or the types of amino acid residues, specifically, it can be 1 to 20, 1 to 10, 1 to 5, or even 1 to 3. The aforementioned mutation is preferably a conservative mutation, which is a neutral mutation not causing functional change, and the conservative mutation is typically a conservative substitution. Examples of conservative substitution include: substitutions of Phe, Trp, and Tyr for each other in the case of aromatic amino acids, substitutions of Leu, Ile, and Val for each other in the case of hydrophobic amino acids, substitutions of Gln and Asn for each other in the case of polar amino acids, substitutions of Lys, Arg, and His for each other in the case of basic amino acids, substitutions of Asp and Glu for each other in the case of acidic amino acids, and substitutions of Ser and Thr for each other in the case of hydroxyl group-containing amino acids. More specifically, examples of the conservative mutations include: substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Be, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Be, or Leu for Val. The aforementioned amino acid substitutions, deletions, insertions, additions, inversions or the like can be a result of a naturally-occurring mutation or a variation due to an individual difference or difference of species of a microorganism having the isomaltase gene (mutant or variant).

Furthermore, the malL or glvA gene can be a DNA which is able to hybridize with a complementary sequence of the nucleotide sequence of SEQ ID NO: 13 or 39 or a probe which can be prepared from the sequence under stringent conditions and encodes a protein having the isomaltase activity. The "stringent conditions" referred to here are conditions under which a so-called specific hybrid is formed, and a non-specific hybrid is not formed. Specific examples of the stringent conditions include conditions of washing once, 2 or 3 times in another example, at a salt concentration and temperature corresponding to washing of typical Southern hybridization, i.e., 1×SSC, 0.1% SDS at 60° C., 0.1×SSC, 0.1% SDS at 60° C. in another example, 0.1×SSC, 0.1% SDS at 68° C. in another example. In particular, the "stringent conditions" can be conditions under which DNAs not less than 80% homologous, not less than 90% homologous, not less than 95% homologous, not less than 98% homologous, or even not less than 99% homologous, hybridize to each other.

Furthermore, the extracellular isomaltase gene can be obtained by ligating the aforementioned coding region of the isomaltase gene with a sequence coding for a signal peptide for secreting the protein into a cell surface layer or out of cell to modify the gene so that it expresses a fusion protein of isomaltase and the signal peptide. For example, by using a so-called secretion vector, which has a promoter sequence and a sequence coding for a signal peptide, and expresses a protein encoded by a DNA sequence inserted downstream from the foregoing sequences in a secretable form, an extracellular isomaltase gene can be constructed. Examples of such a secretion vector include pEZZ18 described in the example section. Furthermore, examples of a signal peptide include the protein A derived from *Staphylococcus aureus* described in the examples, and so forth (refer to EMBO J., 4 (4), 1075-1080 (1985)).

In order to impart to a microorganism the activity to take up isomaltose into the cells or increase the activity of the microorganism to take up isomaltose into the cells, for example, a gene coding for an isomaltose transporter can be introduced into the microorganism. Furthermore, when the microorganism inherently has an isomaltose transporter gene, by increasing copy number of the endogenous isomaltase gene, modifying an expression control sequence such as promoter of the isomaltose transporter gene, increasing copy number of the isomaltose transporter gene, or the like, expression of the gene can be increased to increase the activity to take up isomaltose into cells. Furthermore, when the microorganism inherently has an isomaltose transporter gene, the activity to take up isomaltose into cells can be increased by introducing an exogenous or endogenous isomaltose transporter gene. Furthermore, the isomaltose transporter gene can also have a function to take up maltose in addition to isomaltose.

Acquisition of the isomaltose transporter gene, introduction of the gene into a microorganism, and enhancement of isomaltose transporter gene expression can be performed in the same manners as those for the aforementioned isomaltase gene. Impartation or increase of the activity to take up isomaltose and/or maltose into cells can be confirmed by, for example, the method described in J. Bacteriol., 1991 April; 173(7):2180-6 or J. Biol. Chem., 2006 June, 30; 281 (26): 17900-8.

As the isomaltose transporter gene, the glvC (malP) gene of *Bacillus subtilis* can be used. The glvC gene of *Bacillus subtilis* is a gene coding for maltose enzyme IICB (PTS maltose enzyme IICB) of the phosphotransferase system (PTS), and this enzyme has an activity to transfer the phosphate group of phosphoenolpyruvate to isomaltose and/or maltose, and to take up phosphorylated isomaltose and/or maltose into the cytoplasm.

Furthermore, other isomaltose transporter genes include the genes coding for the sugar transporters MsmE, MsmF and MsmG, which belong to the multiple sugar metabolism system of *Streptococcus mutans*, and the AGT1 gene of *Saccharomyces cervisiae*. These genes are explained in detail in the examples.

The amino acid sequence of a protein encoded by the glvC gene, and the gene coding it are shown in SEQ ID NOS: 42 and 41, respectively (corresponding to Genbank Accession No. BG11848).

Furthermore, the amino acid sequences of MsmE, MsmF and MsmG are shown in SEQ ID NOS: 16, 18 and 20, respectively, and the nucleotide sequences of the genes coding for them are shown in SEQ ID NOS: 15, 17 and 19, respectively (corresponding to Genbank Accession No. NP_721287.1, NP_721288.1 and NP_721289.1, respectively). The nucleotide sequence of the AGT1 gene, and the amino acid sequence encoded thereby are shown in SEQ ID NOS: 21 and 22, respectively (corresponding to Genbank Accession No. AAY99642).

Furthermore, genes coding for an isomaltose transporter are shown in Table 3.

TABLE 3

| No. | Gene | Bacterium | Function |
|---|---|---|---|
| 1 | YP_001420453 | *Bacillus amyloliquefaciens* FZB42 | phosphotransferase system IIC components glucose/maltose/N-acetylglucosamine-specific carbohydrate transport and metabolism |
| 2 | YP_078080 | *Bacillus licheniformis* ATCC 14580 | phosphotransferase system (PTS) maltose-specific enzyme IICB component |
| 3 | AAK69555 | *Clostridium acetobutylicum* | PTS_IIB, PTS system, glucose/sucrose Specific IIB subunit |
| 4 | ZP_02631647 | *Clostridium perfringens* E str. JGS1987 | PTS system maltose-specific eiicb Component |
| 5 | ZP_02638912 | *Clostridium perfringens* CPE str. F4969 | PTS system maltose-specific eiicb Component |

TABLE 3-continued

| No. | Gene | Bacterium | Function |
| --- | --- | --- | --- |
| 6 | ZP_02642923 | *Clostridium perfringens* NCTC 8239 | PTS system maltose-specific eiicb Component |
| 7 | NP_561112 | *Clostridium perfringens* str. 13 | PTS arbutin-like enzyme IIBC component |
| 8 | NP_290321 | *Escherichia coli* O157:H7 EDL933 | putative PTS component |
| 9 | YP_001746010 | *Escherichia coli* SMS-3-5 | PTS system, alpha-glucoside-specific IIBC component |
| 10 | ZP_03050141 | *Escherichia coli* E110019 | PTS system, alpha-glucoside-specific IIBC component |
| 11 | NP_561112 | *Clostridium perfringens* str. 13 | PTS arbutin-like enzyme IIBC component |
| 12 | YP_854647 | *Aeromonas hydrophila* subsp. *hydrophila* ATCC 7966 | PTS system maltose-specific eiicb component |
| 13 | O06900 | *Fusobacterium mortiferum* | PTS system alpha-glucoside-specific EIICB component |
| 14 | YP_001143948 | *Aeromonas salmonicida* subsp. *salmonicida* A449 | PTS system alpha-glucoside-specific EIICB component |
| 15 | ZP_03124405 | *Clostridium difficile* QCD-23m63 | PTS system, IIBC component |
| 16 | YP_187123 | *Staphylococcus aureus* subsp. *aureus* COL | PTS system, IIBC components |
| 17 | YP_001785613 | *Clostridium botulinum* A3 str. Loch Maree | PTS system, glucose/glucoside family, IIBC component |

The isomaltose transporter gene derived from a *Bacillus* bacterium or another microorganism, for example, glvC, genes coding for MsmE, MsmF and MsmG, and homologues of the AGT1 gene can also be obtained by PCR using oligonucleotides prepared on the basis of the aforementioned sequence information or sequence information of gene or protein known for the microorganism as primers, or hybridization using an oligonucleotide prepared on the basis of the aforementioned sequence information as a probe from a chromosomal DNA or chromosomal DNA library of a microorganism. As for the aforementioned gene homologues, the above descriptions for the malL gene homologues are applied. Furthermore, the descriptions concerning variants of the malL and glvA genes are also applied to the isomaltose transporter genes.

It is estimated that even if the activity to take up isomaltose into cells is imparted or enhanced, uptake of glucose by a microorganism is not substantially influenced.

By culturing the microorganism in a medium, a target substance can be produced in culture, i.e., the microbial cells or the medium. By collecting the target substance from the cells or the medium, the target substance can be produced.

The chosen medium can be a medium which is conventionally used in the production of target substances by fermentation using a microorganism can be used. That is, typical media containing a carbon source, nitrogen source, inorganic ions, and other organic components as required can be used. The carbon source can contain isomaltose, isomaltose and glucose, or isomaltose, maltose and glucose. In one embodiment, the microorganism does not necessarily show two-stage proliferation, so-called diauxy, in a medium containing glucose and isomaltose, or glucose, isomaltose, and maltose as the carbon source. Examples of such a carbon source containing isomaltose and glucose, or isomaltose, maltose and glucose include, for example, hydrolysates or enzymatic decomposition products of starches.

As carbon sources other than glucose, isomaltose and maltose, saccharides such as lactose and galactose, alcohols such as glycerol and sorbitol, organic acids such as fumaric acid, citric acid and succinic acid, and so forth can be used.

When maltose or isomaltose is present in a hydrolyzed solution of starch as contaminants other than glucose, isomaltose and maltose can be present in an amount of 0.1 to 10% by weight based on the weight of the total carbon source.

Furthermore, when isomaltose is used as the carbon source, isomaltose can be present in an amount of 1 to 50% by weight, 1 to 20% by weight, or 1 to 10% by weight in another example, based on the weight of the total carbon source. Furthermore, glucose can be present in an amount of 50 to 99% by weight, 80 to 99% by weight, 90 to 99% by weight in another example, based on the weight of the total carbon source. The weight ratio of isomaltose and glucose can be 1:1 to 1:100, 1:5 to 1:100, 1:10 to 1:100 in another example.

Furthermore, when maltose is used as the carbon source in addition to isomaltose, maltose can be present in an amount of 1 to 50% by weight, 1 to 20% by weight, 1 to 10% by weight in another example, based on the weight of the total carbon source. Furthermore, glucose can be present in an amount of 50 to 99% by weight, 80 to 99% by weight, 90 to 99% by weight in another example, based on the weight of the total carbon source. The weight ratio of maltose and glucose can be 1:1 to 1:100, 1:5 to 1:100, or 1:10 to 1:100 in another example.

Concentrations of isomaltose and maltose in the medium can be quantified by HPLC.

As the nitrogen source, inorganic ammonium salts such as ammonium sulfate, ammonium chloride, and ammonium phosphate, organic nitrogen such as soybean hydrolysate, ammonia gas, aqueous ammonia, and so forth can be used.

As organic trace nutrient sources, the medium can contain required substances such as vitamin $B_1$, L-homoserine, and L-tyrosine, yeast extract, and so forth in appropriate amounts. Other than the above, potassium phosphate, magnesium sulfate, iron ions, manganese ions and so forth are added in small amounts, as required.

The culture can be performed under conventionally used well-known conditions selected according to the chosen microorganism. For example, the culture can be performed under aerobic conditions for 16 to 120 hours. The culture temperature can be controlled to be 25° C. to 45° C., and pH can be controlled to be 5 to 8 during the culture. Inorganic or organic, acidic or alkaline substances as well as ammonia gas or the like can be used to adjust the pH.

When a basic amino acid such as L-lysine is produced, the production can be performed by a method in which fermentation is performed by controlling pH of the medium during the culture to be 6.5 to 9.0, and the pH of the medium at the end of the culture to be 7.2 to 9.0, and controlling the pressure in the fermentation tank to be positive during the fermentation, or by supplying carbon dioxide gas or a mixed gas containing carbon dioxide gas to the medium to provide a culture period where the medium contains 20 mM or more of bicarbonate ions and/or carbonate ions, so that these bicarbonate ions and/or carbonate ions serve as counter ions of cations mainly consisting of a basic amino acid, and the objective basic amino acid is then collected (Japanese Patent Laid-open No. 2002-65287, U.S. Patent Published Application No. 2002/0025564, EP 1813677 A).

When a microorganism having a basic amino acid-producing ability is cultured in a medium under aerobic conditions, carbonate ions, bicarbonate ions, or both can be used as major counter ions of the basic amino acid. To provide carbonate ions and/or bicarbonate ions in an amount required to serve as counter ions of the basic amino acid, it is known that the pH of the medium can be controlled to be 6.5 to 9.0, 6.5 to 8.0 in another example, during the culture, and can be 7.2 to 9.0 at the end of the culture. The pressure in the fermentation tank can be controlled so that it is positive during fermentation, or carbon dioxide or a mixed gas containing carbon dioxide can be supplied into the medium (Japanese Patent Laid-open No. 2002-65287, U.S. Patent Published Application No. 2002/0025564, EP 1813677 A).

Pressure in the fermentation tank can be controlled to be positive during the fermentation, and at the same time, carbon dioxide gas or a mixed gas containing carbon dioxide gas can be supplied to the medium. Both the above operations can be performed so that there is a culture period when 20 mM or more in an example, 30 mM or more in another example, 40 mM or more in another example, of bicarbonate ions and/or carbonate ions are present in the medium. The internal pressure of the fermentation tank, supply amount of carbon dioxide or mixed gas containing carbon dioxide, or the limited gas supply volume can be determined by, for example, measuring bicarbonate ions or carbonate ions in the medium, or the pH or ammonia concentration of the medium.

In the above embodiment, the pH of the medium is controlled to be 6.0 to 9.0, 6.5 to 8.0 in another example, during the culture, and 7.2 to 9.0 at the end of the culture. According to the above embodiment, it is possible to suppress the pH of the medium so that the amount of bicarbonate ions and/or carbonate ions present in the medium to serve as counter ions is lower as compared to the conventional methods. When the pH is controlled with ammonia, ammonia is supplied in order to increase the pH, and it can serve as a nitrogen source for the basic amino acid. Examples of cations other than the basic amino acid in the medium include K, Na, Mg, Ca etc. originating in medium components. These can be present in an amount of 50% or less of the total cations.

Furthermore, the internal pressure of the fermentation tank during fermentation can be made positive by, for example, making the gas supply pressure higher than the exhaust pressure. By making the internal pressure of the fermentation tank positive, the carbon dioxide generated by fermentation dissolves in the culture medium to generate bicarbonate ions or carbonate ions, and these can serve as counter ions of the basic amino acid. The internal pressure of the fermentation tank is, specifically, 0.03 to 0.2 MPa, 0.05 to 0.15 MPa, 0.1 to 0.3 Mpa in another example, in terms of the gage pressure (pressure difference with respect to the atmospheric pressure). Moreover, by supplying carbon dioxide or a mixed gas containing carbon dioxide to the culture medium, carbon dioxide can be dissolved in the medium. Furthermore, when supplying carbon dioxide or a mixed gas containing carbon dioxide to the medium, the internal pressure of the fermentation tank can be adjusted to be positive.

The internal pressure of the fermentation tank can be adjusted to be positive by, for example, making the gas supply pressure higher than the exhaust pressure. Furthermore, when carbon dioxide is supplied to the medium, for example, pure carbon dioxide or a mixed gas containing 5 volume % or more of carbon dioxide can be bubbled in the medium.

The aforementioned methods for dissolving bicarbonate ions and/or carbonate ions in the medium can be used independently, or two or more of them can be used in combination.

In the conventional methods, a sufficient amount of ammonium sulfate or ammonium chloride is usually added to the medium to serve as counter anions of the basic amino acid to be produced. Sulfuric acid or hydrochloric acid decomposition products of proteins etc. are also added to the medium as a nutrient component, and thus the generated sulfate ions and chloride ions are present in the medium. Therefore, the concentration of the weakly acidic carbonate ions is extremely low during the culture, such as on the order of ppm. The above embodiment is characterized in that these sulfate ions and chloride ions are reduced, and the carbon dioxide released by the microorganism during fermentation is dissolved in the medium in the aforementioned fermentation environment and can be used as counter ions. Therefore, it is not required to add sulfate ions or chloride ions to the medium in an amount more than that required for the growth. An appropriate amount of ammonium sulfate or the like can be added to the medium at an early stage of the culture, and the addition is terminated in the middle of the culture. Alternatively, ammonium sulfate or the like can be added while maintaining the balance with the dissolved carbonate ions or bicarbonate ions in the medium. Moreover, as a nitrogen source of the basic amino acid, ammonia can be added to the medium. Ammonia can be supplied to the medium independently, or together with other gases.

Lower concentrations of anions other than bicarbonate ions and/or carbonate ions in the medium can be used so long as they are present in amounts that are required for the growth of the microorganism. Examples of such anions include chloride ions, sulfate ions, phosphate ions, ionized organic acids, hydroxide ions, and so forth. The total molar concentration of these other ions can be usually 900 mM or lower, 700 mM or lower, 500 mM or lower, 300 mM or lower, 200 mM or lower in another example.

To reduce the necessary amounts of sulfate ions and/or chloride ions is one of the aspects of the present invention, and the total amount of sulfate ions or chloride ions, or both present in the medium is usually 700 mM or lower, 500 mM or lower, 300 mM or lower, 200 mM or lower, 100 mM or lower in another example.

If ammonium sulfate is added to a medium as a counter ion source of a basic amino acid, carbon dioxide in the culture medium is usually eliminated by sulfate ions. However, it is not always necessary to add an excess amount of ammonium sulfate to the medium, and therefore carbon dioxide can be easily dissolved in the fermentation medium.

Furthermore, the total ammonia concentration in the medium can be controlled to such an extent that "production of the basic amino acid is not inhibited". Examples of such conditions include, for example, when the yield and/or productivity can be 50% or more, 70% or more, 90% or more in another example, of the yield and/or productivity which is obtained under optimal conditions. Specifically, the total ammonia concentration in the medium can be 300 mM or lower, 250 mM or lower, 200 mM or lower in another example. The dissociation degree of the ammonia decreases as the pH becomes higher. Non-dissociating ammonia is more toxic to bacteria as compared to ammonium ions. Therefore, the upper limit of the total ammonia concentration should be determined depending on the pH of the culture medium. That is, as the pH of the culture medium increases, the acceptable total ammonia concentration decreases. Therefore, the aforementioned total ammonia concentration "which does not inhibit the basic amino acid production" can be determined for each specific pH value. However, the total ammonia concentration range that is acceptable at the highest pH level during the culture can be used as the upper limit of the total ammonia concentration throughout the entire culture period.

On the other hand, the total ammonia concentration which functions as a source of nitrogen required for growth of the microorganism and production of the basic substance is not particularly limited, and can be appropriately determined, so long as the reduced level of the nitrogen source which can result in continuous depletion of ammonia during the culture does not reduce production of the objective substance by the microorganism. For example, the ammonia concentration can be measured over time during the culture, and if the ammonia in the medium is depleted, a small amount of ammonia can be added to the medium. Although the total ammonia concentration after the addition of ammonia is not particularly limited, the total ammonia concentration can be, for example, 1 mM or higher, 10 mM or higher, 20 mM or higher in another example.

Furthermore, in L-glutamic acid fermentation, the culture can be performed so that L-glutamic acid precipitates in the medium by using a liquid medium adjusted to have a condition under which L-glutamic acid is precipitated. The condition under which L-glutamic acid is precipitated is, for example, pH 5.0 to 4.0, pH 4.5 to 4.0, pH 4.3 to 4.0, pH 4.0 in another example (European Patent Laid-open No. 1078989).

Furthermore, for the production of a nucleic acid, by allowing purine nucleoside phosphorylase and phosphoribosyltransferase to act on inosine or guanosine, 5'-inosinic acid or 5'-guanylic acid can be obtained.

Moreover, it is also possible to phosphorylate the purine nucleoside produced using a microorganism by allowing phosphotransferase to act on the purine nucleoside to produce a purine nucleotide (nucleoside 5'-phosphoric acid ester) (Japanese Patent Laid-open No. 2000-295996). For example, the method for producing a purine nucleotide using an *Escherichia* bacterium into which a gene encoding inosine guanosine kinase of *Escherichia coli* is introduced (WO91/08286), and the method for producing a purine nucleotide using *Corynebacterium* ammoniagenes into which a gene encoding inosine guanosine kinase of *Exiguobacterium acetylicum* is introduced (WO96/30501) can be used.

Moreover, it is also possible to produce a purine nucleotide (nucleoside 5'-phosphoric acid ester) by allowing a microorganism which is able to produce a nucleoside 5'-phosphoric acid ester or acid phosphatase (EC 3.1.3.2) to act on the purine nucleoside produced by using the microorganism and a phosphate donor such as polyphosphoric acid, phenyl phosphate and carbamyl phosphate. Although the microorganism able to produce a nucleoside 5'-phosphoric acid ester is not particularly limited so long as a microorganism which is able to convert a purine nucleoside into a purine nucleotide is chosen, examples include, for example, the microorganism disclosed in International Publication WO96/37603.

Moreover, *Escherichia blattae* JCM 1650, *Serratia ficaria* ATCC 33105, *Klebsiella planticola* IFO 14939 (ATCC 33531), *Klebsiella pneumoniae* IFO 3318 (ATCC 8724), *Klebsiella terrigena* IFO 14941 (ATCC 33257), *Morganella morganii* IFO 3168, *Enterobacter aerogenes* IFO 12010, *Enterobacter aerogenes* IFO 13534 (ATCC 13048), *Chromobacterium fluviatile* JAM 13652, *Chromobacterium violaceum* IFO 12614, *Cedecea lapagei* JCM 1684, *Cedecea davisiae* JCM 1685, *Cedecea neteri* JCM 5909, and so forth disclosed in Japanese Patent Laid-open No. 07-231793 can also be used.

As the acid phosphatase, for example, those disclosed in Japanese Patent Laid-open No. 2002-000289 can be used, and an acid phosphatase with increased affinity to a nucleoside (Japanese Patent Laid-open No. 10-201481), a mutant acid phosphatase with decreased nucleotidase activity (WO96/37603), a mutant acid phosphatase with decreased phosphoric acid ester hydrolysis activity (Japanese Patent Laid-open No. 2001-245676) and so forth can be used.

A purine nucleotide can be obtained by chemically phosphorylating a purine nucleoside produced using the microorganism (Bulletin of the Chemical Society of Japan, 42, 3505). Moreover, a method of obtaining GMP by coupling the microorganism with an XMP-producing ability and XMP aminase activity using the ATP-regenerating system of a microorganism, and a method of obtaining IMP by coupling inosine kinase (Biosci. Biotech. Biochem., 51, 840 (1997); Japanese Patent Laid-open No. 63-230094) can also be used.

Inosine, guanosine or purine nucleosides used for the aforementioned preparation of a purine nucleotide can be purified, or can be present in a purine nucleoside fermentation broth, or can be a crude product containing a purine nucleoside.

To collect L-amino acids or nucleic acids from the medium after completion of the culture, a special method is not required. The L-amino acid or nucleic acid can contain bacterial cells, medium components, moisture, and by-product metabolites of the microorganism in addition to the L-amino acid or nucleic acid. Purity of the collected L-amino acid or nucleic acid is, for example, 50% or higher, 85% or higher, 95% or higher in another example (U.S. Pat. No. 5,431,933, Japanese Patent Publication No. 1-214636, U.S. Pat. Nos. 4,956,471, 4,777,051, 4,946,654, 5,840,358, 6,238,714, U.S. Patent Published Application No. 2005/0025878).

The L-amino acid can be collected by a combination of the following conventionally known methods: use of an ion-exchange resin (Nagai, H. et al., Separation Science and Technology, 39(16), 3691-3710), membrane separation (Japanese Patent Laid-open Nos. 9-164323 and 9-173792), crystallization (WO2008/078448, WO2008/078646), and other methods.

Furthermore, when the target substance is L-phenylalanine, L-phenylalanine produced by the method can be used for, for example, producing a lower alkyl ester of α-L-aspartyl-L-phenylalanine (also referred to as "aspartame"). From L-phenylalanine obtained by dissolving L-phenylalanine crystals, and aspartic acid or a derivative thereof, a lower alkyl ester of α-L-aspartyl-L-phenylalanine can be produced. Examples of the lower alkyl ester include methyl ester, ethyl ester, propyl ester, and so forth.

The method for synthesizing a lower alkyl ester of α-L-aspartyl-L-phenylalanine from L-phenylalanine and aspartic acid or its derivative is not particularly limited, so long as L-phenylalanine or its derivative is used for the synthesis of the lower alkyl ester of α-L-aspartyl-L-phenylalanine. Specifically, for example, a lower alkyl ester of α-L-aspartyl-L-phenylalanine can be produced by the following method (U.S. Pat. No. 3,786,039). L-Phenylalanine is esterified to obtain a lower alkyl ester of L-phenylalanine. The L-phenylalanine alkyl ester is reacted with an L-aspartic acid derivative of which a β-carboxyl group is protected and an α-carboxyl group is esterified to activate. Examples of such a derivative include N-acyl-L-aspartic anhydride such as N-formyl-, N-carbobenzoxy-, or N-p-methoxycarbobenzoxy-L-aspartic anhydride. By this condensation reaction, a mixture of N-acyl-α-L-aspartyl-L-phenylalanine and N-acyl-β-L-aspartyl-L-phenylalanine is obtained. If the condensation reaction is performed in the presence of an organic acid of which acid dissociation constant at 37° C. is $10^{-4}$ or less, the ratio of the α-isomer to the β-isomer in the mixture is increased (Japanese Patent Laid-Open No. 51-113841). Then, the N-acyl-α-L-aspartyl-L-phenylalanine is separated from the mixture, and hydrogenated to obtain α-L-aspartyl-L-phenylalanine.

Furthermore, α-L-aspartyl-L-phenylalanine-α-ester can be conveniently produced at high yield by producing α-L-aspartyl-L-phenylalanine-β-ester from L-phenylalanine and L-asparatic acid-α,β-diester using an enzyme having an ability to catalyze a reaction in which L-phenylalanine does not nucleophilically attack the β-ester moiety of L-asparatic acid-α,β-diester, but nucleophilically attacks the α-ester moiety or a substance containing such an enzyme, to produce α-L-aspartyl-L-phenylalanine-β-ester, and producing α-L-aspartyl-L-phenylalanine-α-ester from the obtained α-L-aspartyl-L-phenylalanine-β-ester (WO2004/065610).

Furthermore, a technique of synthesizing a dipeptide using a mutant peptide synthetase derived from *Sphingobacterium* bacteria is disclosed, and α-L-aspartyl-L-phenylalanine can be produced using this technique (WO2006/075486).

EXAMPLES

Hereinafter, the present invention will be explained more specifically with reference to the following examples. In the following examples, the reagents were from Wako Pure Chemical Industries or Nakalai Tesque, unless specified otherwise. The compositions of the media used in the examples are as shown below.

L Medium:
10 g/L of Bacto trypton (Difco), 5 g/L of yeast extract (Difco), 5 g/L of NaCl
The medium was steam-sterilized at 120° C. for 20 minutes.

L Agar Medium
L medium, 15 g/L of Bacto agar (Difco)
The medium was steam-sterilized at 120° C. for 20 minutes.

Amino Acid Production Medium
20 g/L of $(NH_4)_2SO_4$, 1 g/L of $KH_2PO_4$, 1 g/L of $MgSO_4 \cdot 7H_2O$, 10 mg/L of $FeSO_4 \cdot 7H_2O$, 10 mg/L of $MnSO_4 \cdot 5H_2O$, 2 g/L of yeast extract (Becton, Dickinson and Company), 40 g/L of saccharide (glucose or maltose or mixture of these at a suitable ratio), 100 mg/L of L-tyrosine, 30 g/L of $CaCO_3$ (Japanese Pharmacopoeia), 50 mg/L of streptomycin or ampicillin The saccharide, $MgSO_4 \cdot 7H_2O$, and the antibiotic were separately sterilized. The other components were mixed, adjusted to pH 7.0 with KOH, and autoclaved at 115° C. for 10 minutes. $CaCO_3$ was subjected to dry sterilization at 180° C. for 2 days. Streptomycin was sterilized by filtration. Ampicillin was used as a 70% solution in ethanol.

PCR
Pyrobest DNA Polymerase produced by Takara Shuzo or KOD DNA Polymerase produced by Toyobo was used in PCR, which was performed according to the protocol which came with the polymerase enzyme. After completion the reaction, gel filtration was performed in order to remove the residual primers. A Microspin™ S-400HR Column produced by Amersham Pharmacia Biotech was used according to the protocol that came with the column.

Ligation Reaction/Blunting-Kination Reaction
Ligation Kit ver. 2 or BKL Kit of Takara Bio was used, and the reactions were performed according to the protocol that came with the kit.

Transformation of *E. coli*
*E. coli* was transformed with the ligation reaction mixture or plasmid DNA according to the method of Hanahan et al. (Hanahan, D., 1983, Studies on transformation of *Escherichia coli* with plasmids, J. Mol. Biol., 166, 557-580).

Example 1

Amino Acid Production by a Strain which Extracellularly Expresses Isomaltose

<1> Cloning of the malL Gene
A colony of the *Bacillus subtilis* Marburg 168 strain (BGSC1A1 strain, obtained from *Bacillus* Genetic Stock Center) was inoculated into 5 ml of the L medium, and culture was performed overnight with shaking. Chromosomal DNA was prepared from the culture medium by using Wizard Genomic DNA Purification Kit (Promega). PCR was performed using this chromosomal DNA as a template. The two primers which were used are shown below:

```
Primer 1
                              (SEQ ID NO: 1)
5'-GAGAATTCAATGAGTGAATGGTGGAAAGAAGCTGTCG-3'

Primer 2
                              (SEQ ID NO: 2)
5'-CGAGAAAATGATATTCTGCAGTATCTGTTATCACTCCGTC-3'
```

Nucleotides 3 to 8 in SEQ ID NO: 1 correspond to the EcoRI site, and nucleotides 16 to 21 in SEQ ID NO: 2 correspond to the PstI site.

The PCR product was treated with the restriction enzymes EcoRI and PstI, and ligated with the secretion vector pEZZ18 (Amersham Pharmacia Biotech), which had been previously treated with the same restriction enzymes. The pEZZ18 vector described above includes pBR322 and the replication origin of f1 phage, into which a multi-cloning site was inserted upstream of lacZα, the signal sequence of the protein A of *Staphylococcus aureus* required for secretion, and two IgG binding regions (ZZ region), which are present further upstream of the multi-cloning site. If a gene is inserted downstream of the ZZ region, the protein encoded by the gene is expressed as a fusion protein with the signal sequence and the ZZ region. The fusion protein is then secreted out of the *E. coli* cells, and can be easily purified by affinity chromatography using the ZZ region. The aforementioned PCR product was ligated to pEZZ18 so that the isomaltose decomposition enzyme encoded by the malL gene forms a fusion protein with the signal sequence of the protein A and the IgG binding region (Z region), which is located further downstream.

The ligation reaction mixture was used to transform *E. coli* JM109. Transformants were selected on L agar medium containing 50 µg/ml of ampicillin, 0.2 mM IPTG (isopropyl-β-D-thiogalactopyranoside), and 40 µg/ml of X-gal (5-bromo-4-chloro-3-indolyl-β-D-galactoside). A plasmid was extracted from the transformants, and insertion of the target fragment was confirmed. This plasmid was designated pEZ-ZmalL.

<2> Construction of Vector Plasmid pRS

PCR was performed by using the plasmid pVIC40 (WO90/04636) as the template DNA, and the two oligonucleotides shown below as primers.

pVIC40 was obtained by inserting the thrA*BC operon, which contains a mutant thrA gene, into a vector derived from RSF1010 which also contains a streptomycin resistance gene. The plasmid can be prepared from the *Escherichia coli* VKPM B-3996 strain harboring this plasmid. The B-3996 strain was deposited at the Russian National Collection of Industrial Microorganisms (VKPM, 1 Dorozhny proezd., 1 Moscow 117545, Russia) on Apr. 7, 1987 under the accession number B-3996.

```
Primer 3
                                       (SEQ ID NO: 3)
5'-GCGCGAATTCCAACGGGCAATATGTCTCTG-3'

Primer 4
                                       (SEQ ID NO: 4)
5'-GCGCCAATTGGATGTACCGCCGAACTTCAA-3'
```

The PCR product was treated with the restriction enzymes EcoRI and MunI. Separately, pVIC40 was digested with the restriction enzyme EcoRI, and the longest fragment was chosen from the digested DNA fragments, and ligated with the aforementioned PCR fragment. The ligation reaction mixture was used to transform *E. coli* JM109. Transformants were obtained on the L agar medium containing 50 μg/ml of streptomycin. PCR was performed using plasmids prepared from the transformants as the template, Primer 3 described above, and Primer 5 described below, and a plasmid for which a band of about 270 bp was detected was chosen, and designated pRS. pRS has the structure of pVIC40, but without the thrABC operon.

```
Primer 5
5'-CAGTTTTCTGATGAAGCGCG-3'          (SEQ ID NO: 5)
```

<3> Construction of the Plasmid pRSL Containing the lacZα Gene

PCR was performed using pSTV29 (Takara Shuzo) as the template and the two oligonucleotides shown below as primers. pSTV29 is a low copy number plasmid containing the lacZ gene.

```
Primer 6
5'-CCAATACGCAAACCGCCTCTCC-3'        (SEQ ID NO: 6)

Primer 7
5'-CAAATGTAGCACCTGAAG-3'            (SEQ ID NO: 7)
```

The lacZα fragment was ligated with a fragment obtained by digesting pRS with the restriction enzyme PstI and blunt-ended. The ligation reaction mixture was used to transform *E. coli* JM109. Transformants were selected on L agar medium containing 50 μg/ml of streptomycin, 0.2 mM IPTG (isopropyl-β-D-thiogalactopyranoside) and 40 μg/ml of X-gal (5-bromo-4-chloro-3-indolyl-β-D-galactoside). A plasmid was extracted from the transformants, and insertion of the target fragment was confirmed. This plasmid was designated pRSL.

<4> Insertion of the malL Gene into pRSL

A malL gene fragment having a sequence for the signal sequence of the protein A was amplified by PCR using pEZ-ZmalL as the template DNA and the following primers.

```
Primer 8
                                       (SEQ ID NO: 8)
5'-CATTAGGCACCCCAAGCTTTACACTTTATGCTTCC-3'

Primer 9
                                       (SEQ ID NO: 9)
5'-GACGGCCAGTGCCAAGCTTGCATGCCTGCAGG-3'
```

The nucleotide numbers 14 to 19 in SEQ ID NOS: 8 and 9 correspond to HindIII sites.

The obtained PCR product was treated with the restriction enzyme HindIII, and ligated with the vector pRSL which had been similarly treated with HindIII. The ligation reaction mixture was used to transform *E. coli* JM109. Transformants were selected on L agar medium containing 50 μg/ml of streptomycin (Sm), 0.2 mM IPTG (isopropyl-β-D-thiogalactopyranoside) and 40 μg/ml of X-gal (5-bromo-4-chloro-3-indolyl-β-D-galactoside). A plasmid was extracted from the transformants, and insertion of the target fragment was confirmed. This plasmid was designated pRSLmalL.

<5> Evaluation of Amino Acid Production Culture pRSLmalL was introduced into an amino acid-producing bacterium, and the ability of the bacterium to assimilate isomaltose and produce amino acids was investigated.

The bacterial strain used to produce L-phenylalanine was obtained by introducing either the pMW118 plasmid or pMGAL1 plasmid (Japanese Patent Laid-open No. 5-344881) into *E. coli* W3110(tyrA) (refer to European Patent Laid-open No. 488424). Furthermore, the bacterial strain used to produce L-lysine was *E. coli* WC196ΔcadAΔldcC (also referred to as "WC196LC", WO2006/078039). These strains were transformed with pRSLmalL.

The W3110(tyrA) strain can be obtained by removing the plasmid pHATerm from *Escherichia coli* W3110(tyrA)/pHATerm. The *E. coli* W3110(tyrA)/pHATerm strain was designated as AJ12662, and deposited at the National Institute of Bioscience and Human-Technology, Agency of Industrial Science and Technology, Ministry of International Trade and Industry (currently the independent administrative agency, National Institute of Advanced Industrial Science and Technology, International Patent Organism Depositary, Tsukuba Central 6, 1-1, Higashi 1-Chome, Tsukuba-shi, Ibaraki-ken, 305-8566, Japan) as an international deposit on Nov. 16, 1991, and assigned an accession number of FERM BP-3653 (WO01/053459).

pMGAL1 contains a gene coding for 3-deoxy-D-arabino-heptunorate-7-phosphate synthase derived from *Escherichia* bacterium and desensitized to feedback inhibition, and a gene coding for chorismate mutase-prephenate dehydratase derived from *Escherichia* bacterium and desensitized to feedback inhibition (Japanese Patent Laid-open Publication No. 5-344881).

Each of the obtained transformants was inoculated into 5 ml of the L medium containing an antibiotic (50 μg/ml of streptomycin for the strains harboring pRSL or pRSLmalL, 50 μg/ml of ampicillin for the strains harboring pMW118 or pMGAL1) and cultured at 37° C. overnight with shaking. Then, 50 μl of the culture medium was added to the same L agar medium as described above and cultured overnight at 37° C. Colonies of cells on an ⅛ portion of the plate were scraped and inoculated into 20 ml of an amino acid production medium containing a mixture of glucose and maltose as the carbon source in a 500-ml volume Sakaguchi flask. Initial concentrations of glucose and isomaltose were 36 g/L and 6.6 g/L, respectively. After 24 hours, the amino acid concentrations and the amount of remaining glucose and maltose were quantified. As controls, transformants obtained by introducing pRSL into *E. coli* W3110(tyrA)/pMW118, W3110(tyrA)/pMGAL1, and WC196LC were used. The results are shown in Table 4.

TABLE 4

| | | Amino acid production culture | | | |
|---|---|---|---|---|---|
| Host | | Plasmid | Phenylalanine (g/L) | Lysine (g/L) | Residual glucose (g/L) | Residual isomaltose (g/L) |
| W3110(tyrA) | pMW118 | pRSL | 0.96 | — | 0.00 | 6.22 |
| W3110(tyrA) | pMW118 | pRSLmalL | 1.33 | — | 0.00 | 0.00 |
| W3110(tyrA) | pMGAL1 | pRSL | 5.38 | — | 0.00 | 6.18 |
| W3110(tyrA) | pMGAL1 | pRSLmalL | 6.48 | — | 0.00 | 0.00 |
| WC196LC | — | pRSL | — | 1.25 | 0.00 | 6.27 |
| WC196LC | — | pRSLmalL | — | 1.70 | 0.00 | 1.85 |

—: Not tested

When the vector pRSL was introduced into *E. coli* W3110(tyrA)/pMW118 or W3110(tyrA)/pMGAL1, isomaltose was not assimilated, but when pRSLmalL was introduced, isomaltose was assimilated in the same culture time. Similarly, when pRSL was introduced into *E. coli* WC196LC, isomaltose was not assimilated, but when pRSLmalL was introduced, most of isomaltose was assimilated in the same culture time. It was found that when the culture time was extended to 42 hours for the strain introduced with pRSLmalL, isomaltose was completely consumed. From the above results, it was found that introduction of the malL gene induced isomaltose assimilation.

Furthermore, the amounts of L-phenylalanine or L-lysine produced increased after introduction of the malL gene in all the strains.

Example 2

Construction of Strain Expressing Intracellular Isomaltase and Isomaltose Transporter <1> Construction of Plasmid for Intracellular Expression of the malL Gene In order to express isomaltose hydrolase (isomaltase) in the *Escherichia coli* MG1655 strain, an expression plasmid for the malL gene derived from *Bacillus subtilis* is constructed.

<1-1> Construction of Plasmid pRSL12 Containing the lacZ Gene

PCR is performed by using pHSG399 (Takara Shuzo) as the template and two oligonucleotides shown below as primers.

```
Primer 6
5'-CCAATACGCAAACCGCCTCTCC-3'      (SEQ ID NO: 6)

Primer 10
5'-AGTCAGTGAGCGAGGAAG-3'           (SEQ ID NO: 10)
```

The resulting fragment is ligated to a pRS fragment obtained by digesting pRS with the restriction enzyme PstI and blunt-ending. The ligation reaction mixture is used to transform *E. coli* JM109. Selection of the transformants is performed on the L agar medium containing 50 µg/ml of streptomycin, 0.2 mM IPTG (isopropyl-β-D-thiogalactopy-ranoside) and 40 µg/ml of X-gal (5-bromo-4-chloro-3-indolyl-β-D-galactoside). A plasmid is extracted from the transformants, and insertion of the target fragment is confirmed. This plasmid is designated pRSL12.

<1-2> Construction of Plasmid pRSL12malL(Self) Intracellularly Expressing malL Gene A colony of the *Bacillus subtilis* Marburg 168 strain (BGSC1A1 strain, obtainable from *Bacillus* Genetic Stock Center) is inoculated into 5 ml of the L medium, and culture is performed overnight with shaking. Chromosomal DNA is prepared from the culture medium by using Wizard Genomic DNA Purification Kit (Promega). By using this chromosomal DNA as the template and two oligonucleotides shown below as primers, PCR is performed to amplify a malL gene fragment containing the native promoter region of the malL gene.

```
Primer 11
                                    (SEQ ID NO: 11)
5'-GGCTGGCAATCGTTCAAAGCTTTGCAGGCATGCGC-3'

Primer 12
                                    (SEQ ID NO: 12)
5'-CGAGAAAATGATATTCTGCAGTATCTGTTATCACTCCGTC-3'
```

The PCR product is treated with the restriction enzymes HindIII and PstI, and ligated with the vector pRSL12 which had been previously treated with the same restriction enzymes. The ligation reaction mixture is used to transform *E. coli* JM109. Selection of the transformants is performed on the L agar medium containing 50 µg/ml of streptomycin (Sm), 0.2 mM IPTG (isopropyl-β-D-thiogalactopyranoside), and 40 µg/ml of X-gal (5-bromo-4-chloro-3-indolyl-β-D-galactoside). A plasmid is extracted from the transformants, and insertion of the target fragment is confirmed. This plasmid is designated pRSL12malL(self).

<2> Construction of Plasmid Expressing Isomaltose Transporter Derived from *Streptococcus mutans*

*Streptococcus mutans* has genes coding for a group of proteins involved in the assimilation of various saccharides such as melibiose, isomaltose and raffinose, and is called the multiple sugar metabolism system (Tao, L., et al., INFECTION AND IMMUNITY, 1993, 61, 1121). The multiple sugar metabolism system is encoded by an operon which includes a series of genes including msmR (activator), aga (α-galactosidase), msmE (saccharide-binding protein), msmF (membrane protein), msmG (membrane protein), gtfA (sucrose phosphorylase), msmK (ATP-binding protein), and dexB (dextran glucosidase).

In order to induce the uptake of isomaltose into *Escherichia coli* cells, a plasmid expressing the sugar transporters MsmE, MsmF, and MsmG of the multiple sugar metabolism system is prepared. On the basis of the sequence information on the multiple sugar metabolism system of *Streptococcus*

*mutans* previously described (Russell and R. R. B. et al., The Journal of Biological Chemistry, 1992, 7, 4631), primers for amplifying the region coding for MsmE, MsmF and MsmG from a chromosomal DNA are designed. PCR is performed by using the designed primers and chromosomal DNA extracted from *Streptococcus mutans* as the template.

The chromosomal DNA can be obtained by using the Bacterial Genomic DNA Purification Kit (Edge Bio System). For PCR, a cycle of 96° C. for 20 seconds, 65° C. for 20 seconds and 72° C. for 3 minutes is repeated 25 times using Pyrobest DNA Polymerase (Takara Bio). The ends of the PCR product are blunt-ended, and then phosphorylated. The obtained DNA fragment is digested with the restriction enzyme SmaI, and the resultant fragment is ligated to the plasmid vector pMW119 (NIPPON GENE) or pTWV229 (Takara Bio) which had been treated with an alkaline phosphatase to construct plasmids pMW119-Smsm and pTWV229-Smsm expressing an isomaltose transporter.

<3> Construction of Plasmid Expressing Isomaltose Transporter Derived from *Saccharomyces cervisiae*

The AGT1 gene of *Saccharomyces cervisiae* codes for the Agt1p protein which transports various α-glucosides such as maltose, isomaltose and maltotriose into cells (Han, E. K., et al., Molecular Microbiology, 1995, 17, 1093). In order to induce uptake of isomaltose into *Escherichia coli* cells, a plasmid expressing the AGT1 gene is constructed. On the basis of the sequence information on the AGT1 gene of *Saccharomyces cervisiae* (GenBank/L47346), primers for amplifying the AGT1 gene from the chromosomal DNA are designed. PCR is performed by using these primers and the chromosomal DNA of *Saccharomyces cervisiae* as the template. The chromosomal DNA can be obtained by using the Bacterial Genomic DNA Purification Kit (Edge Bio System). For PCR, a cycle of 96° C. for 20 seconds, 65° C. for 20 seconds and 72° C. for 2 minutes is repeated 25 times using Pyrobest DNA Polymerase (Takara Bio). The ends of the PCR product are blunted, and then phosphorylated. The resulting DNA fragment is digested with the restriction enzyme SmaI, and ligated to the plasmid vector pMW119 (NIPPON GENE) or pTWV229 (Takara Bio) which had been treated with an alkaline phosphatase to construct plasmids pMW119-AGT1 and pTWV229-AGT1 which express Agt1p.

<4> Impartation of the Ability to Assimilate Isomaltose to *Escherichia coli* K 12-Strain MG1655

When isomaltase is intracellularly expressed, an isomaltose transporter is required for assimilation of isomaltose, in addition to isomaltase. Therefore, by incorporating both the aforementioned pRSL12malL(self), and pMW119-Smsm or pTWV229-Smsm into the *Escherichia coli* K12 strain MG1655, a strain which assimilates isomaltose can be produced. Similarly, by incorporating both the aforementioned pRSL12malL(self), and pMW119-AGT1 or pTWV229-AGT1, a strain which assimilates isomaltose can also be produced.

Competent cells of *Escherichia coli* K 12 strain MG1655 are prepared, and transformed with pRSL12malL(self) and pMW119-Smsm or pTWV229-Smsm. Similarly, the K12 strain MG1655 is transformed with pRSL12malL(self) and pMW119-AGT1 or pTWV229-AGT1. The transformants are cultured on the L agar medium containing antibiotics, 50 µg/ml of streptomycin and 100 µg/ml of ampicillin, to select the transformants. The transformant expresses isomaltase and the isomaltose transporter, and has ability to assimilate isomaltose.

By imparting the ability to produce a target substance such as an amino acid to a strain having the ability to assimilate isomaltose obtained as described above, a strain that produces the target substance from a raw material containing isomaltose can be obtained. Furthermore, by imparting the ability to assimilate isomaltose to a strain having the ability to produce a target substance in the same manner as described above, a strain that produces the target substance from a raw material containing isomaltose can also be obtained.

Example 3

Introduction of Isomaltose/Maltose Uptake System and Isomaltase/Maltase Genes by Gene Transfer of glvA and glvC For gene transfer of the glvA and glvC genes, the following variant of the tac promoter was used for expression.

```
Sequence of Tac promoter:
                                          (SEQ ID NO: 32)
5'-ccctgTTGACAattaatcatcggctcgTATAATgtgtggaatcg-3'

Sequence of PTacA promoter:
                                          (SEQ ID NO: 33)
5'-ccctgTTGACAattaatcatcggctcgAATAATgtgtggaatcg-3'

Sequence of PtacB promoter:
                                          (SEQ ID NO: 43)
5'-ccctgTTGGAAttaatcatcggctcgTATAATgtgtggaatcg-3'
```

<1> Cloning of the glvA Gene

A colony of the *Bacillus subtilis* Marburg 168 strain (ATCC 6051) was inoculated into 5 ml of the L medium, and culture was performed overnight with shaking. Chromosomal DNA was prepared from the culture medium by using the Wizard Genomic DNA Purification Kit (Promega). PCR was performed using this chromosomal DNA as the template. The sequences of the two primers used are shown below.

```
Primer 23
5'-AGAAATTTCCCGCTCTATGG-3'          (SEQ ID NO: 23)

Primer 24
5'-TGTAGTGCTGATTGATCAGTTC-3'        (SEQ ID NO: 24)
```

The obtained PCR product was subjected to blunting-kination treatments by using the BKL Kit (Takara Bio), and ligated with the pTWV229 vector (Takara Bio) treated with the restriction enzyme SmaI.

The ligation reaction mixture was used to transform *E. coli* JM109. Transformants were selected on the L agar medium containing 100 µg/ml of ampicillin. A plasmid was extracted from the transformants, and insertion of the target fragment was confirmed. This plasmid was designated pTWV229-self-glvA-Fw. In this plasmid, the glvA gene was inserted in the forward direction with respect to the lac promoter present on pTWV229.

<2> Construction of Vector Plasmid pMW219-ΔPlac

In order to express the glvC gene with minimal influence of the lac promoter present on the vector plasmid pMW219 on the transcription of the glvC gene, it was decided to delete the lac promoter site of the vector plasmid pMW219. The vector plasmid pMW219 was treated with the restriction enzyme HindIII, and purified by ethanol precipitation. This fragment was further treated with the restriction enzyme PstI, and used for PCR using Primers 25 and 26.

```
Primer 25
                                         (SEQ ID NO: 25)
5'-GCCaagcttGCATGCCTGCAGGTCGACTCTAGAGG-3'

Primer 26
                                         (SEQ ID NO: 26)
5'-CCCaagcttGCTAACTCACATTAATTGCGTTG-3'
```

The small letters indicate HindIII recognition sites.

The PCR product was treated with HindIII, and the ends of DNA were ligated (self-ligation).

The ligation reaction mixture was used to transform *E. coli* JM109. Transformants were selected on L agar medium containing 50 µg/ml of kanamycin. A plasmid was extracted from the transformants, and it was confirmed that the plasmid had the intended structure. This plasmid was designated pMW219-ΔPlac. This vector plasmid had a structure in which the lac promoter region present on pMW219 was deleted.

<3> Cloning of the glvC Gene

A colony of the *Bacillus subtilis* Marburg 168 strain (ATCC 6051) was inoculated into 5 ml of the L medium, and culture was performed overnight with shaking. Chromosomal DNA was prepared from the culture medium by using Wizard Genomic DNA Purification Kit (Promega). PCR was performed using this chromosomal DNA as the template. The sequences of the two primers used are shown below.

```
Primer 27
                                         (SEQ ID NO: 27)
5'-CAATTTCACACAAGGAGACTGCCATGATGCAAAAAATTCAGCG-3'

Primer 28
                                         (SEQ ID NO: 28)
5'-CCCAAGCTTCCCCTTTTTACTCGATTGTCTC-3'
```

The obtained PCR product was purified by phenol/chloroform extraction and ethanol precipitation. This DNA fragment was used as the template together with Primer 29 (SEQ ID NO: 29) and Primer 30 (SEQ ID NO: 30) in PCR. PCR was performed in the presence of a small amount of Primer 31.

```
Primer 29
                                         (SEQ ID NO: 29)
5'-CCCAAGCTTCCTGTTGACAATTAATCATCGGCTCGAATAATGTGTGG
AATCGTGAGCGGATAACAATTTCACACAAGGAG-3'

Primer 30
                                         (SEQ ID NO: 30)
5'-CCCAAGCTTCCCCTTTTTACTCGATTGTCTC-3'

Primer 31
                                         (SEQ ID NO: 31)
5'-CGAATAATGTGTGGAATCGTGAGCGGATAACAATTTCACACAAGGAG
ACTGCCATGATGCAAAAAATTCAGCGCTTTGGA-3'
```

The PCR product was subjected to electrophoresis using agarose gel, and the target D NA fragment was purified by using QIAquick Gel Extraction Kit (QIAGEN). The purified DNA fragment was subjected to blunting-kination treatments, and ligated with the pMW219-ΔPlac vector which had been treated with the restriction enzyme SmaI.

The ligation reaction mixture was used to transform *E. coli* JM109. Transformants we re selected on L agar medium containing 50 µg/ml of kanamycin. A plasmid was extracted from the transformants, and insertion of the target fragment was confirmed. This plasmid was designated pMW219-ΔPlac-PtacA-glvC. In this plasmid, the glvC gene was inserted in the reverse direction with respect to the deleted Plac (lac promoter) of pMW219-ΔPlac.

<4> Evaluation of the Ability to Assimilate Isomaltose of Strains Expressing glvA and glvC An *E. coli* K12 MG1655 strain transformed with pTWV229-self-glvA-Fw and pMW219-ΔPlac-PtacA-glvC was prepared. This strain was designated glvA+glvC/MG1655. As a control strain for this experiment, an *E. coli* K12 MG1655 strain transformed with pTWV229 and pMW219-ΔPlac was prepared. This strain was designated pTWV229+pMW219-ΔPlac/MG1655.

Growth of the control strain (pTWV229+pMW219-ΔPlac/MG1655 strain) and the glvA+glvC/MG1655 strain was traced by OD measurement in a medium obtained by adding 0.2% isomaltose to M9 minimal medium (M9-iMal medium) (FIG. 1). As seen from FIG. 1, the glvA+glvC/MG1655 strain showed favorable growth, which was not seen for the control strain. That is, it was found that the ability to assimilate isomaltose could be imparted by expressing the glvA an d glvC genes in the *E. coli* K12 MG1655 strain.

| M9 medium | |
|---|---|
| MgSO$_4$•7H$_2$O | 0.247 g/L |
| CaCl$_2$•2H$_2$O | 0.0147 g/L |
| Na$_2$HPO$_4$•12H$_2$O | 15.1 g/L |
| KH$_2$PO$_4$ | 3 g/L |
| NaCl | 0.5 g/L |
| NH$_4$Cl | 1.0 g/L |

The medium was adjusted to pH 6.8 with NaOH, and as a carbon source, 2.0 g/L of iso maltose was added to the M9-iMal medium, or 0.2 g/L of glucose and 1.8 g/L of isomaltose were added to the M9-Glc+iMal medium, and the media were subjected to filter sterilization. Isomaltose was added as a 75% isomaltose solution of Nakalai so that the isomaltose amount became the aforementioned amount. Furthermore, before culture, ampicillin and kanamycin were added at concentrations of 100 µg/ml and 50 µg/ml, respectively.

Figure 2:
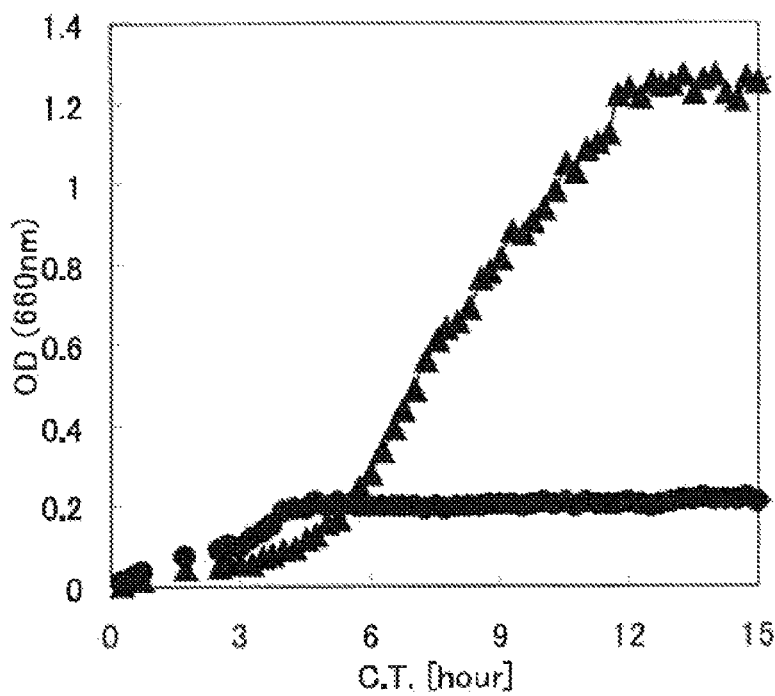
FIG. 2 shows growth curves of the pTWV229+pMW219-ΔPlac/MG1655 strain (●) and the glvA+glvC/MG1655 strain (▲) in the M9-Glc (0.02%)-iMal (0.18%).

Growth of the control strain (pTWV229+pMW219-ΔPlac/MG1655 strain) and the glvA+glvC/MG1655 strain was traced by OD measurement in a medium obtained by adding 0.02% of glucose and 0.18% of isomaltose to the M9 minimal medium (M9-Glc+iMal medium) (FIG. 2). As seen from FIG. 2, whereas growth of the control strain was arrested at OD of about 0.2, the glvA+glvC/MG1655 strain did not show two-stage proliferation, but showed favorable growth. Since two-stage proliferation was not confirmed, it was found that the glvA+glvC/MG1655 strain simultaneously assimilated glucose and isomaltose.

Example 4

Production of Amino Acid by the Ability to Assimilate Isomaltose-Imparted Strain <1> Cloning of the glvC Gene A colony of the *Bacillus subtilis* Marburg 168 strain (ATCC 6051) was inoculated into 5 ml of the L medium, and culture was performed overnight with shaking. Chromosomal DNA was prepared from the culture medium by using the Wizard Genomic DNA Purification Kit (Promega). By using this chromosomal DNA as the template, PCR was performed. The sequences of two primers used are shown below.

Primer 34
(SEQ ID NO: 34)
5'-GAATCGTGAGCGGATAACAATTTCACACAAGGAGACTGCCATGATGC
AAAAAATTCAGCGCTTTGGAAGCGCGATGTTTG-3'

Primer 35
(SEQ ID NO: 35)
5'-TGACGGCAAACGAAAACCCTCC-3'

The PCR product was subjected to electrophoresis using agarose gel, and the target DNA fragment is purified by using the QIAquick Gel Extraction Kit (QIAGEN). The purified DNA fragment was used as the template together with Primer 36 and Primer 37 to perform PCR. PCR was performed in the presence of a small amount of Primer 38.

Primer 36
(SEQ ID NO: 36)
5'-GCtctagaGCCCCTGTTGGAATTAATCATCGGCTCGTATAATGTGT
G-3'

Primer 37
(SEQ ID NO: 37)
5'-GCtctagaGCTGACGGCAAACGAAAACCCTCCCGAAAAGG-3'

The small letters indicate XbaI recognition sites.

Primer 38
(SEQ ID NO: 38)
5'-CCCTGTTGGAATTAATCATCGGCTCGTATAATGTGTGGAATCGTGAG
CGGATAACAATTTCACACAAGGAGACTGCC-3'

The PCR product was purified by using Wizard PCR Preps DNA Purification System (Promega), and treated with the restriction enzyme XbaI. Then, this fragment was ligated with p MW219-ΔPlac which had been similarly treated with the restriction enzyme XbaI.

The ligation reaction mixture was used to transform *E. coli* JM109. Selection of the transformants was performed on the L agar medium containing 50 µg/ml of kanamycin. A plasmid was extracted from the transformants, and insertion of the target fragment was confirmed. This plasmid was designated pMW219-ΔPlac-PtacB-glvC-Rv. In this plasmid, the glvC gene was inserted in the reverse direction with respect to the deleted Plac (lac promoter) of pMW219-ΔPlac.

<3> Evaluation of Amino Acid Production Culture

*E. coli* WC196ΔcadAΔldcC (also referred to as WC196LC) was used (refer to WO2006/078039) to evaluate the production of L-lysine. This strain was transformed with pCABD2 (WO95/16042), pTWV229-self-glvA-Fw, and pMW219-ΔPlac-PtacB-glvC-Rv. The transformant was designated pCABD2+glvA+glvC/WC196LC. A WC196LC strain transformed with pCABD2 (WO95/16042), pTWV229, and pMW219-ΔPlac was prepared as a control strain for this experiment. The obtained transformant was designated pCABD2+pTWV229+pMW219-ΔPlac/WC196LC.

The strains prepared above were each cultured at 37° C. in the L medium containing 20 mg/L of streptomycin, 100 mg/L of ampicillin, and 50 mg/L of kanamycin until OD600 became about 0.6, then an equal volume of 40% glycerol solution was added to the medium, and the mixture was stirred. Then, the mixture was divided into appropriate volumes, stored at −80° C., and used as glycerol stocks.

The glycerol stocks of the control strain and pCABD2+glvA+glvC/WC196LC were thawed, 500 µL of each stock was uniformly applied to an L plate containing 20 mg/L of streptomycin, 100 mg/L of ampicillin, and 50 mg/L of kanamycin, and culture was performed at 37° C. for 24 hours. The cells were scraped from the plate, and suspended in the L-lysine production medium shown below (MS-Glc+iMal medium), and proliferated to OD=15. This cell suspension was inoculated in a volume of 1 mL to 19 mL of the L-lysine production medium shown below (MS-Glc+iMal medium) containing 20 mg/L of streptomycin, 100 mg/L of ampicillin and 50 mg/L of kanamycin, which was contained in a 500 mL-volume Sakaguchi flask, and culture was performed at 37° C. on a reciprocally shaking culture apparatus. As the L-lysine production medium, the MS-Glc+iMal medium containing glucose and isomaltose as sugar sources was used. The amount of L-lysine which accumulated in the medium, as well as the remaining glucose and isomaltose, were quantified during the culture and after completion of the culture. The L-lysine yields based on glucose, and the amounts of remaining glucose and isomaltose, are shown in Table 5.

| | |
|---|---|
| Isomaltose | 3.3 g/L |
| $(NH_4)_2SO_4$ | 24 g/L |
| $KH_2PO_4$ | 1.0 g/L |
| $MgSO_4 \cdot 7H_2O$ | 1.0 g/L |
| $FeSO_4 \cdot 7H_2O$ | 0.01 g/L |
| $MnSO_4 \cdot 7H_2O$ | 0.08 g/L |
| Yeast Extract | 2.0 g/L |
| L-Isoleucine | 0.1 g/L |
| $CaCO_3$ | 50 g/L |

(Japanese Pharmacopoeia)

The medium was adjusted to pH 7.0 with KOH, and autoclaved at 115° C. for 10 minutes, except that glucose, isomaltose, and $MgSO_4 \cdot 7H_2O$ were mixed, and autoclaved separately from the other components. $CaCO_3$ was added after hot air sterilization.

TABLE 5

Results of amino acid production culture

| | pCABD2 + pTWV229 + pMW219-ΔPlac/WC196LC | | pCABD2 + glvA + glvC/WC196LC | | |
|---|---|---|---|---|---|
| Culture time (hour) | 14 | 25 | 22 | 25 | 38.5 |
| Yield for Glc (%) | 31.1 | 34.1 | 44.6 | 43.0 | 43.3 |
| Lys (g/L) | 3.5 | 6.1 | 5.8 | 7.4 | 7.8 |
| Initial Glc concentration (g/L) | 17.9 | 17.9 | 17.9 | 17.9 | 17.9 |
| Residual Glc concentration (g/L) | 6.7 | 0.0 | 4.9 | 0.8 | 0.0 |
| Initial iMal concentration (g/L) | 3.3 | 3.3 | 3.3 | 3.3 | 3.3 |
| Residual iMal concentration (g/L) | 3.3 | 3.2 | 0.0 | 0.0 | 0.0 |

When pCABD2 and the vectors pTWV229 and pMW219-ΔPlac were introduced into WC196LC, isomaltose was not assimilated. On the other hand, when the glvA and glvC expression plasmids were introduced, isomaltose was assimilated simultaneously with glucose. Furthermore, by introducing the glvA and glvC expression plasmids, L-lysine accumulation was increased, and the yield based on glucose was improved.

Then, the pCABD2+glvA+glvC/WC196LC strain was cultured in a medium using glucose, maltose, and isomaltose as sugar sources. The glycerol stock of pCABD2+glvA+glvC/WC196LC was thawed, 500 µL of the stock was uniformly applied to an L plate containing 20 mg/L of streptomycin, 100 mg/L of ampicillin, and 50 mg/L of kanamycin, and culture was performed at 37° C. for 24 hours. The cells were scraped from the plate, and suspended in the L-lysine production medium shown below (MS-Glc+Mal+iMal medium), and proliferated to OD=15. This cell suspension was inoculated into a volume of 1 mL to 19 mL of the L-lysine production medium shown below (MS-Glc+Mal+iMal medium) containing 20 mg/L of streptomycin, 100 mg/L of ampicillin, and 50 mg/L of kanamycin, which was contained in a 500 mL-volume Sakaguchi flask, and culture was performed at 37° C. on a reciprocally shaking culture apparatus. As the L-lysine production medium, the MS-Glc+Mal+iMal medium containing glucose, maltose and isomaltose as sugar sources was used. The amount of L-lysine which had accumulated in the medium, as well as the remaining glucose, maltose, and isomaltose, were quantified during the culture and after completion of the culture. The L-lysine yields based on glucose, and amounts of remained glucose, maltose and isomaltose are shown in Table 6.

| | |
|---|---|
| Glucose | 17.8 g/L |
| Isomaltose | 3.3 g/L |
| Maltose | 3.3 g/L |
| $(NH_4)_2SO_4$ | 24 g/L |
| $KH_2PO_4$ | 1.0 g/L |
| $MgSO_4 \cdot 7H_2O$ | 1.0 g/L |
| $FeSO_4 \cdot 7H_2O$ | 0.01 g/L |
| $MnSO_4 \cdot 7H_2O$ | 0.08 g/L |
| Yeast extract | 2.0 g/L |
| L-Isoleucine | 0.1 g/L |
| $CaCO_3$ | 50 g/L |

(Japanese Pharmacopoeia)

The medium was adjusted to pH 7.0 with KOH, and autoclaved at 115° C. for 10 minutes, except that glucose, maltose, isomaltose and $MgSO_4 \cdot 7H_2O$ were mixed, and autoclaved separately from the other components. $CaCO_3$ was added after hot air sterilization.

TABLE 6

Result of amino acid production culture in MS-Glc + Mal + iMal medium

| | Culture time (hour) | | |
|---|---|---|---|
| | 22 | 25 | 38.5 |
| Yield for Glc (%) | 56.6 | 46.5 | 45.3 |
| Lys (g/L) | 5.6 | 6.9 | 8.1 |
| Initial Glc concentration (g/L) | 17.9 | 17.9 | 17.9 |
| Residual Glc concentration (g/L) | 8.0 | 3.1 | 0.0 |
| Initial Mal concentration (g/L) | 2.8 | 2.8 | 2.8 |
| Residual Mal concentration (g/L) | 0.0 | 0.0 | 0.0 |
| Initial iMal concentration (g/L) | 3.2 | 3.2 | 3.2 |
| Residual iMal concentration (g/L) | 0.0 | 0.0 | 0.0 |

When pCABD2, and the glvA and glvC expression plasmids were introduced into WC196LC, maltose and isomaltose were assimilated simultaneously with glucose. Furthermore, by introducing the glvA and glvC expression plasmids, L-lysine accumulation was increased, and the yield based on glucose was improved.

INDUSTRIAL APPLICABILITY

According to the present invention, substances can be produced from isomaltose and/or maltose as raw materials by fermentation using a microorganism. The ability of a microorganism to assimilate isomaltose and/or maltose can even be imparted to a microorganism which does not have a native ability to assimilate isomaltose and/or maltose.

While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method for producing an L-amino acid utilizing a microorganism, which comprises:
    A) culturing the microorganism in a medium, and
    B) collecting the L-amino acid from the medium,
    wherein the microorganism has been modified so that:
    A) it comprises isomaltase activity,
    B) the isomaltase activity is increased, or
    C) both
    wherein said activity causes the decomposition of phosphorylated isomaltose into glucose and glucose phosphate;
    wherein the isomaltase is encoded by a DNA selected from the group consisting of:
    (A) a DNA comprising the nucleotide sequence shown in SEQ ID NO: 39,
    (B) a DNA which is able to hybridize with a sequence complementary to the nucleotide sequence of SEQ ID NO: 39 under stringent conditions comprising washing at a salt concentration and temperature of 0.1×SSC, 0.1% SDS at 60° C., and codes for a protein having isomaltase activity, and
    wherein the microorganism comprises a gene coding for PTS maltose enzyme IICB,
    wherein the PTS maltose enzyme IICB is encoded by a DNA selected from the group consisting of:
    (A) a DNA comprising the nucleotide sequence shown in SEQ ID NO: 41,
    (B) a DNA which is able to hybridize with a sequence complementary to the nucleotide sequence of SEQ ID NO: 41 under stringent conditions comprising washing at a salt concentration and temperature of 0.1×SSC, 0.1% SDS at 60° C., and codes for a protein which is able to cause the microorganism to take up isomaltose, wherein the medium contains a component selected from the group consisting of:
    A) isomaltose, and
    B) isomaltose and maltose.

2. The method according to claim 1, wherein the microorganism has been further modified so that:
    A) it comprises maltase activity,
    B) the maltase activity is increased, or
    C) both.

3. The method according to claim 2, wherein the microorganism has been further modified so that:
    A) it is able to take up maltose,
    B) the activity to take up maltose is increased, or
    C) both.

4. The method according to claim 1, wherein the microorganism comprises a gene coding for isomaltase of a *Bacillus* bacterium.

5. The method according to claim 1, wherein the isomaltase is selected from the group consisting of:
   (A) a protein comprising the amino acid sequence shown in SEQ ID NO: 40,
   (B) a protein comprising the amino acid sequence shown in SEQ ID NO: 40, but wherein one to 10 amino acid residues are substituted, deleted, inserted or added, and the protein has the isomaltase activity.

6. The method according to claim 1, wherein the PTS maltose enzyme IICB is selected from the group consisting of:
   (A) a protein comprising the amino acid sequence shown in SEQ ID NO: 42,
   (B) a protein comprising the amino acid sequence shown in SEQ ID NO: 42, but wherein one to 10 amino acid residues are substituted, deleted, inserted or added, and the protein is able to cause the microorganism to take up isomaltose.

7. The method according to claim 1, wherein the microorganism is an Enterobacteriaceae bacterium.

8. The method according to claim 7, wherein the Enterobacteriaceae bacterium is an *Escherichia* bacterium.

9. The method according to claim 8, wherein the *Escherichia* bacterium is *Escherichia coli*.

10. The method according to claim 9, wherein the amino acid is selected from the group consisting of L-lysine, L-threonine, L-glutamic acid, and L-phenylalanine.

11. The method according to claim 1, wherein the microorganism is a coryneform bacterium.

12. The method according to claim 11, wherein the coryneform bacterium is *Corynebacterium gluitamicum*.

13. The method according to claim 7, wherein the Enterobacteriaceae bacterium is a *Pantoea* bacterium.

14. The method according to claim 13, wherein the *Pantoea* bacterium is *Pantoea ananatis*.

15. The method according to claim 1, wherein said isomaltase has an amino acid sequence having an homology of 80% or more to the total amino acid sequence of SEQ ID NO: 40.

16. The method according to claim 1, wherein said PTS maltose enzyme IICB has an amino acid sequence having a homology of 80% or more to the total amino acid sequence of SEQ ID NO: 42.

17. The method according to claim 1, wherein the microorganism has been modified by introducing, increasing the copy number of, or modifying an expression control sequence of the isomaltase gene and the gene coding for PTS maltose enzyme IICB.

* * * * *

SEQUENCE LISTING

<160> NUMBER OF SEQ ID NOS: 43

<210> SEQ ID NO 1
<211> LENGTH: 37
<212> TYPE: DNA
<213> ORGANISM: Artificial Sequence
<220> FEATURE:
<223> OTHER INFORMATION: primer

<400> SEQUENCE: 1
gagaattcaa tgagtgaatg gtggaaagaa gctgtcg                37

<210> SEQ ID NO 2
<211> LENGTH: 40
<212> TYPE: DNA
<213> ORGANISM: Artificial Sequence
<220> FEATURE:
<223> OTHER INFORMATION: primer

<400> SEQUENCE: 2
cgagaaaatg atattctgca gtatctgtta tcactccgtc             40

<210> SEQ ID NO 3
<211> LENGTH: 30

```
<212> TYPE: DNA
<213> ORGANISM: Artificial Sequence
<220> FEATURE:
<223> OTHER INFORMATION: primer

<400> SEQUENCE: 3
gcgcgaattc caacgggcaa tatgtctctg                                      30

<210> SEQ ID NO 4
<211> LENGTH: 30
<212> TYPE: DNA
<213> ORGANISM: Artificial Sequence
<220> FEATURE:
<223> OTHER INFORMATION: primer

<400> SEQUENCE: 4
gcgccaattg gatgtaccgc cgaacttcaa                                      30

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
cagttttctg atgaagcgcg                                                 20

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
ccaatacgca aaccgcctct cc                                              22

<210> SEQ ID NO 7
<211> LENGTH: 18
<212> TYPE: DNA
<213> ORGANISM: Artificial Sequence
<220> FEATURE:
<223> OTHER INFORMATION: primer

<400> SEQUENCE: 7
caaatgtagc acctgaag                                                   18

<210> SEQ ID NO 8
<211> LENGTH: 35
<212> TYPE: DNA
<213> ORGANISM: Artificial Sequence
<220> FEATURE:
<223> OTHER INFORMATION: primer

<400> SEQUENCE: 8
cattaggcac cccaagcttt acactttatg cttcc                                35

<210> SEQ ID NO 9
<211> LENGTH: 32
<212> TYPE: DNA
<213> ORGANISM: Artificial Sequence
<220> FEATURE:
<223> OTHER INFORMATION: primer

<400> SEQUENCE: 9
```

```
gacggccagt gccaagcttg catgcctgca gg                                  32

<210> SEQ ID NO 10
<211> LENGTH: 18
<212> TYPE: DNA
<213> ORGANISM: Artificial Sequence
<220> FEATURE:
<223> OTHER INFORMATION: primer

<400> SEQUENCE: 10
agtcagtgag cgaggaag                                                  18

<210> SEQ ID NO 11
<211> LENGTH: 35
<212> TYPE: DNA
<213> ORGANISM: Artificial Sequence
<220> FEATURE:
<223> OTHER INFORMATION: primer

<400> SEQUENCE: 11
ggctggcaat cgttcaaagc tttgcaggca tgcgc                               35

<210> SEQ ID NO 12
<211> LENGTH: 40
<212> TYPE: DNA
<213> ORGANISM: Artificial Sequence
<220> FEATURE:
<223> OTHER INFORMATION: primer

<400> SEQUENCE: 12
cgagaaaatg atattctgca gtatctgtta tcactccgtc                          40

<210> SEQ ID NO 13
<211> LENGTH: 1686
<212> TYPE: DNA
<213> ORGANISM: Bacillus subtilis
<220> FEATURE:
<221> NAME/KEY: CDS
<222> LOCATION: (1)..(1686)

<400> SEQUENCE: 13 atg agt gaa tgg tgg aaa gaa gct gtc gtt tat caa att tac ccg cgc     48
Met Ser Glu Trp Trp Lys Glu Ala Val Val Tyr Gln Ile Tyr Pro Arg
1               5                   10                  15 agt ttt tat gat gcc aat gga gat gga ttc gga gat ttg caa ggt gtg     96
Ser Phe Tyr Asp Ala Asn Gly Asp Gly Phe Gly Asp Leu Gln Gly Val
            20                  25                  30 att caa aag ctg gat tac atc aaa aac ctc ggg gcg gat gtc atc tgg    144
Ile Gln Lys Leu Asp Tyr Ile Lys Asn Leu Gly Ala Asp Val Ile Trp
        35                  40                  45 ctc tcc ccg gta ttt gat tcc ccg cag gat gac aac gga tat gat atc    192
Leu Ser Pro Val Phe Asp Ser Pro Gln Asp Asp Asn Gly Tyr Asp Ile
    50                  55                  60 agc gat tac aaa aac atg tac gaa aag ttt ggg aca aat gaa gat atg    240
Ser Asp Tyr Lys Asn Met Tyr Glu Lys Phe Gly Thr Asn Glu Asp Met
65                  70                  75                  80 ttt cag ctg att gat gaa gtc cat aaa cgc gga atg aaa atc gtc atg    288
Phe Gln Leu Ile Asp Glu Val His Lys Arg Gly Met Lys Ile Val Met
                85                  90                  95 gat ttg gtc gtg aac cac aca tca gat gag cat gct tgg ttt gct gaa    336
Asp Leu Val Val Asn His Thr Ser Asp Glu His Ala Trp Phe Ala Glu
            100                 105                 110 agc cgc aag tcg aag gac aat cct tac cgg gat tat tat ctt tgg aaa    384
Ser Arg Lys Ser Lys Asp Asn Pro Tyr Arg Asp Tyr Tyr Leu Trp Lys
```

115                 120                 125
gat cct aaa ccg gac ggc tca gag ccg aat aat tgg gga tcg atc ttt        432
Asp Pro Lys Pro Asp Gly Ser Glu Pro Asn Asn Trp Gly Ser Ile Phe
    130                 135                 140 tca ggc tca gcg tgg aca tac gat gaa gga aca ggg cag tat tat ttg        480
Ser Gly Ser Ala Trp Thr Tyr Asp Glu Gly Thr Gly Gln Tyr Tyr Leu
145                 150                 155                 160 cac tac ttt tcg aaa aaa cag cct gat tta aat tgg gaa aac gaa gcc        528
His Tyr Phe Ser Lys Lys Gln Pro Asp Leu Asn Trp Glu Asn Glu Ala
                165                 170                 175 gtt cgc cgg gaa gtt tat gat gta atg aga ttc tgg atg gat aga ggc        576
Val Arg Arg Glu Val Tyr Asp Val Met Arg Phe Trp Met Asp Arg Gly
        180                 185                 190 gtt gac ggc tgg cgg atg gat gtg att ggc tct att tct aaa tac acc        624
Val Asp Gly Trp Arg Met Asp Val Ile Gly Ser Ile Ser Lys Tyr Thr
    195                 200                 205 gat ttt ccg gac tac gaa acg gat cac agc cgc agc tat att gtc ggc        672
Asp Phe Pro Asp Tyr Glu Thr Asp His Ser Arg Ser Tyr Ile Val Gly
210                 215                 220 cgt tat cac tct aac ggc cca cgt ctt cat gag ttt att caa gag atg        720
Arg Tyr His Ser Asn Gly Pro Arg Leu His Glu Phe Ile Gln Glu Met
225                 230                 235                 240 aac agg gaa gtg ctt tct cat tac gac tgc atg aca gtc gga gag gca        768
Asn Arg Glu Val Leu Ser His Tyr Asp Cys Met Thr Val Gly Glu Ala
                245                 250                 255 aac ggc tct gat att gaa gag gcg aaa aag tac aca gat gca agc agg        816
Asn Gly Ser Asp Ile Glu Glu Ala Lys Lys Tyr Thr Asp Ala Ser Arg
        260                 265                 270 caa gag ctg aat atg atc ttt aca ttt gaa cat atg gat att gat aaa        864
Gln Glu Leu Asn Met Ile Phe Thr Phe Glu His Met Asp Ile Asp Lys
    275                 280                 285 gaa caa aac tcg cca aat ggg aaa tgg cag atc aag ccg ttt gat ttg        912
Glu Gln Asn Ser Pro Asn Gly Lys Trp Gln Ile Lys Pro Phe Asp Leu
290                 295                 300 att gct tta aaa aag acg atg aca agg tgg cag acc ggg tta atg aat        960
Ile Ala Leu Lys Lys Thr Met Thr Arg Trp Gln Thr Gly Leu Met Asn
305                 310                 315                 320 gtc ggc tgg aat acc ctt tat ttt gag aac cat gac cag ccg agg gtt       1008
Val Gly Trp Asn Thr Leu Tyr Phe Glu Asn His Asp Gln Pro Arg Val
                325                 330                 335 att tcc cgc tgg ggc aat gac agg aaa ctg cgt aag gaa tgt gcg aag       1056
Ile Ser Arg Trp Gly Asn Asp Arg Lys Leu Arg Lys Glu Cys Ala Lys
        340                 345                 350 gca ttt gca acg gtt ctg cac ggc atg aaa gga acg ccg ttt att tac       1104
Ala Phe Ala Thr Val Leu His Gly Met Lys Gly Thr Pro Phe Ile Tyr
    355                 360                 365 cag gga gaa gaa atc ggc atg gtc aac agc gat atg ccg ctg gag atg       1152
Gln Gly Glu Glu Ile Gly Met Val Asn Ser Asp Met Pro Leu Glu Met
370                 375                 380 tat gat gat ctt gaa ata aag aat gca tat cgt gaa cta gtc gtc gaa       1200
Tyr Asp Asp Leu Glu Ile Lys Asn Ala Tyr Arg Glu Leu Val Val Glu
385                 390                 395                 400 aac aaa acg atg tca gaa aaa gag ttt gtc aaa gcc gtg atg ata aaa       1248
Asn Lys Thr Met Ser Glu Lys Glu Phe Val Lys Ala Val Met Ile Lys
                405                 410                 415 gga agg gat cat gcg aga aca ccg atg cag tgg gat gcc gga aaa cat       1296
Gly Arg Asp His Ala Arg Thr Pro Met Gln Trp Asp Ala Gly Lys His
        420                 425                 430 gcg gga ttc aca gcc gga gac ccg tgg ata ccg gta aat tcc cgc tat       1344

```
                 Ala Gly Phe Thr Ala Gly Asp Pro Trp Ile Pro Val Asn Ser Arg Tyr
                             435                 440                 445 caa gat atc aat gtg aaa gag tct ttg gaa gat caa gat tcg att ttc            1392
Gln Asp Ile Asn Val Lys Glu Ser Leu Glu Asp Gln Asp Ser Ile Phe
    450                 455                 460 ttt tac tat cag aag ctc att caa tta cga aag caa tat aag att atg            1440
Phe Tyr Tyr Gln Lys Leu Ile Gln Leu Arg Lys Gln Tyr Lys Ile Met
465                 470                 475                 480 ata tat ggc gat tat cag ctg ttg cag gag aat gat ccg cag gtc ttt            1488
Ile Tyr Gly Asp Tyr Gln Leu Leu Gln Glu Asn Asp Pro Gln Val Phe
                485                 490                 495 tct tac ctt cga gaa tat cga ggg gaa aag ctt ctt gtc gtt gtg aat            1536
Ser Tyr Leu Arg Glu Tyr Arg Gly Glu Lys Leu Leu Val Val Val Asn
            500                 505                 510 tta tcg gaa gaa aag gct ctg ttc gaa gcg cct cca gaa ctg att cat            1584
Leu Ser Glu Glu Lys Ala Leu Phe Glu Ala Pro Pro Glu Leu Ile His
        515                 520                 525 gag cgt tgg aaa gtg cta att tca aac tat ccg cag gag cgg gct gac            1632
Glu Arg Trp Lys Val Leu Ile Ser Asn Tyr Pro Gln Glu Arg Ala Asp
    530                 535                 540 tta aag agt att agc ctc aaa cct tat gaa gct gtg atg ggc att agt            1680
Leu Lys Ser Ile Ser Leu Lys Pro Tyr Glu Ala Val Met Gly Ile Ser
545                 550                 555                 560 ata tga                                                                    1686
Ile <210> SEQ ID NO 14
<211> LENGTH: 561
<212> TYPE: PRT
<213> ORGANISM: Bacillus subtilis

<400> SEQUENCE: 14

Met Ser Glu Trp Trp Lys Glu Ala Val Val Tyr Gln Ile Tyr Pro Arg
1               5                   10                  15

Ser Phe Tyr Asp Ala Asn Gly Asp Gly Phe Gly Asp Leu Gln Gly Val
                20                  25                  30

Ile Gln Lys Leu Asp Tyr Ile Lys Asn Leu Gly Ala Asp Val Ile Trp
            35                  40                  45

Leu Ser Pro Val Phe Asp Ser Pro Gln Asp Asn Gly Tyr Asp Ile
        50                  55                  60

Ser Asp Tyr Lys Asn Met Tyr Glu Lys Phe Gly Thr Asn Glu Asp Met
65                  70                  75                  80

Phe Gln Leu Ile Asp Glu Val His Lys Arg Gly Met Lys Ile Val Met
                85                  90                  95

Asp Leu Val Val Asn His Thr Ser Asp Glu His Ala Trp Phe Ala Glu
            100                 105                 110

Ser Arg Lys Ser Lys Asp Asn Pro Tyr Arg Asp Tyr Leu Trp Lys
        115                 120                 125

Asp Pro Lys Pro Asp Gly Ser Glu Pro Asn Asn Trp Gly Ser Ile Phe
    130                 135                 140

Ser Gly Ser Ala Trp Thr Tyr Asp Glu Gly Thr Gly Gln Tyr Tyr Leu
145                 150                 155                 160

His Tyr Phe Ser Lys Lys Gln Pro Asp Leu Asn Trp Glu Asn Glu Ala
                165                 170                 175

Val Arg Arg Glu Val Tyr Asp Val Met Arg Phe Trp Met Asp Arg Gly
            180                 185                 190

Val Asp Gly Trp Arg Met Asp Val Ile Gly Ser Ile Ser Lys Tyr Thr
```

195                 200                 205
Asp Phe Pro Asp Tyr Glu Thr Asp His Ser Arg Ser Tyr Ile Val Gly
210                 215                 220

Arg Tyr His Ser Asn Gly Pro Arg Leu His Glu Phe Ile Gln Glu Met
225                 230                 235                 240

Asn Arg Glu Val Leu Ser His Tyr Asp Cys Met Thr Val Gly Glu Ala
                245                 250                 255

Asn Gly Ser Asp Ile Glu Glu Ala Lys Lys Tyr Thr Asp Ala Ser Arg
            260                 265                 270

Gln Glu Leu Asn Met Ile Phe Thr Phe Glu His Met Asp Ile Asp Lys
        275                 280                 285

Glu Gln Asn Ser Pro Asn Gly Lys Trp Gln Ile Lys Pro Phe Asp Leu
290                 295                 300

Ile Ala Leu Lys Lys Thr Met Thr Arg Trp Gln Thr Gly Leu Met Asn
305                 310                 315                 320

Val Gly Trp Asn Thr Leu Tyr Phe Glu Asn His Asp Gln Pro Arg Val
                325                 330                 335

Ile Ser Arg Trp Gly Asn Asp Arg Lys Leu Arg Lys Glu Cys Ala Lys
            340                 345                 350

Ala Phe Ala Thr Val Leu His Gly Met Lys Gly Thr Pro Phe Ile Tyr
        355                 360                 365

Gln Gly Glu Glu Ile Gly Met Val Asn Ser Asp Met Pro Leu Glu Met
370                 375                 380

Tyr Asp Asp Leu Glu Ile Lys Asn Ala Tyr Arg Glu Leu Val Val Glu
385                 390                 395                 400

Asn Lys Thr Met Ser Glu Lys Glu Phe Val Lys Ala Val Met Ile Lys
                405                 410                 415

Gly Arg Asp His Ala Arg Thr Pro Met Gln Trp Asp Ala Gly Lys His
            420                 425                 430

Ala Gly Phe Thr Ala Gly Asp Pro Trp Ile Pro Val Asn Ser Arg Tyr
        435                 440                 445

Gln Asp Ile Asn Val Lys Glu Ser Leu Glu Asp Gln Asp Ser Ile Phe
450                 455                 460

Phe Tyr Tyr Gln Lys Leu Ile Gln Leu Arg Lys Gln Tyr Lys Ile Met
465                 470                 475                 480

Ile Tyr Gly Asp Tyr Gln Leu Leu Gln Glu Asn Asp Pro Gln Val Phe
                485                 490                 495

Ser Tyr Leu Arg Glu Tyr Arg Gly Glu Lys Leu Leu Val Val Val Asn
            500                 505                 510

Leu Ser Glu Glu Lys Ala Leu Phe Glu Ala Pro Pro Glu Leu Ile His
        515                 520                 525

Glu Arg Trp Lys Val Leu Ile Ser Asn Tyr Pro Gln Glu Arg Ala Asp
530                 535                 540

Leu Lys Ser Ile Ser Leu Lys Pro Tyr Glu Ala Val Met Gly Ile Ser
545                 550                 555                 560

Ile

<210> SEQ ID NO 15
<211> LENGTH: 1263
<212> TYPE: DNA
<213> ORGANISM: Streptococcus mutans
<220> FEATURE:
<221> NAME/KEY: CDS
<222> LOCATION: (1)..(1263)

```
<400> SEQUENCE: 15 atg aaa tgg tat aaa aaa att gga tta cta ggt att gtc ggt ctg acg      48
Met Lys Trp Tyr Lys Lys Ile Gly Leu Leu Gly Ile Val Gly Leu Thr
1               5                   10                  15 agc gtc tta cta gct gca tgc aac aaa agt aag gct tcg cag tca aag      96
Ser Val Leu Leu Ala Ala Cys Asn Lys Ser Lys Ala Ser Gln Ser Lys
            20                  25                  30 gag gat aaa gta aca att gag tat ttt aac caa aaa aaa gaa atg gac     144
Glu Asp Lys Val Thr Ile Glu Tyr Phe Asn Gln Lys Lys Glu Met Asp
        35                  40                  45 gct acc ttg aaa aag ata att aag gac ttt gaa agg gaa aat cct aaa     192
Ala Thr Leu Lys Lys Ile Ile Lys Asp Phe Glu Arg Glu Asn Pro Lys
    50                  55                  60 att cat gtc aag atg act agt gtt cca gat gct ggt aca gtc ctc aaa     240
Ile His Val Lys Met Thr Ser Val Pro Asp Ala Gly Thr Val Leu Lys
65                  70                  75                  80 acg cgt gtc tta tca gga gat gtg ccc gat gtt atc aat att tat cct     288
Thr Arg Val Leu Ser Gly Asp Val Pro Asp Val Ile Asn Ile Tyr Pro
                85                  90                  95 caa aat atg gac ttc caa gaa tgg tcc aaa gca ggt tat ttt tat aat     336
Gln Asn Met Asp Phe Gln Glu Trp Ser Lys Ala Gly Tyr Phe Tyr Asn
            100                 105                 110 atg acg ggt aaa gcc tat ctt aac cat tta aag aat cat tat gct aac     384
Met Thr Gly Lys Ala Tyr Leu Asn His Leu Lys Asn His Tyr Ala Asn
        115                 120                 125 gaa tat aaa gtt aat caa aag gtt tac agc gtc ccg tta aca gct aat     432
Glu Tyr Lys Val Asn Gln Lys Val Tyr Ser Val Pro Leu Thr Ala Asn
    130                 135                 140 gtt tca gga att tat tat aac aag acc aaa ttt aaa gaa tta ggt ttg     480
Val Ser Gly Ile Tyr Tyr Asn Lys Thr Lys Phe Lys Glu Leu Gly Leu
145                 150                 155                 160 aag gtt cct gaa act tgg gat gag ttt gtt aaa ttg gtt gaa gaa atc     528
Lys Val Pro Glu Thr Trp Asp Glu Phe Val Lys Leu Val Glu Glu Ile
                165                 170                 175 aaa gca aaa aag gaa aca ccg ttt gct tta gcg gga aca gaa ggt tgg     576
Lys Ala Lys Lys Glu Thr Pro Phe Ala Leu Ala Gly Thr Glu Gly Trp
            180                 185                 190 acc ttg aat ggt tat cat cag tta tcc ttg att tca gtc act ggc agt     624
Thr Leu Asn Gly Tyr His Gln Leu Ser Leu Ile Ser Val Thr Gly Ser
        195                 200                 205 gct aat gcc gct aat aaa tac ctt cgc ttt tcc caa cca aat tcg att     672
Ala Asn Ala Ala Asn Lys Tyr Leu Arg Phe Ser Gln Pro Asn Ser Ile
    210                 215                 220 aaa acc agt gat aaa att tta aaa gaa gat atg gtt cgg ctc aat ctt     720
Lys Thr Ser Asp Lys Ile Leu Lys Glu Asp Met Val Arg Leu Asn Leu
225                 230                 235                 240 tta gca gat gat ggc aat cag cag aaa aat tgg aag gga gct tct tat     768
Leu Ala Asp Asp Gly Asn Gln Gln Lys Asn Trp Lys Gly Ala Ser Tyr
                245                 250                 255 aat gat gct ctt gtg gca ttt gct aat gaa aaa gct ctt atg aca cct     816
Asn Asp Ala Leu Val Ala Phe Ala Asn Glu Lys Ala Leu Met Thr Pro
            260                 265                 270 aat ggt tcg tgg gcc ttg cca gct att aaa caa caa gat ccc aaa ttt     864
Asn Gly Ser Trp Ala Leu Pro Ala Ile Lys Gln Gln Asp Pro Lys Phe
        275                 280                 285 gaa att gga acc ttt gct ttt ccg ggc aaa aaa act gga aat ggc ata     912
Glu Ile Gly Thr Phe Ala Phe Pro Gly Lys Lys Thr Gly Asn Gly Ile
    290                 295                 300 aca gtt gga gcc gga gat tta gct cta tca att tca gct aaa aca aaa     960
Thr Val Gly Ala Gly Asp Leu Ala Leu Ser Ile Ser Ala Lys Thr Lys
```

```
Thr Val Gly Ala Gly Asp Leu Ala Leu Ser Ile Ser Ala Lys Thr Lys
305                 310                 315                 320 cat ctt aaa gaa gct gaa aaa ttt gtt aaa tac atg acg act gct agg      1008
His Leu Lys Glu Ala Glu Lys Phe Val Lys Tyr Met Thr Thr Ala Arg
                325                 330                 335 gcg atg cag aaa tat tat gat gtt gat ggt tca cca gta gca gta aaa      1056
Ala Met Gln Lys Tyr Tyr Asp Val Asp Gly Ser Pro Val Ala Val Lys
            340                 345                 350 gga gtc aga gaa gat aag aat tca cct ttg caa cct tta act aaa tta      1104
Gly Val Arg Glu Asp Lys Asn Ser Pro Leu Gln Pro Leu Thr Lys Leu
        355                 360                 365 gct ttt act gat aaa cac tat gtg tgg tta ggt cag cat tgg aat agt      1152
Ala Phe Thr Asp Lys His Tyr Val Trp Leu Gly Gln His Trp Asn Ser
    370                 375                 380 gaa gat gat ttc ttt aca gcc aca acc aat tat cta atg aca aaa aat      1200
Glu Asp Asp Phe Phe Thr Ala Thr Thr Asn Tyr Leu Met Thr Lys Asn
385                 390                 395                 400 gct aaa ggt tta gct gat ggg ctt aac gct ttc ttt aat cca atg aaa      1248
Ala Lys Gly Leu Ala Asp Gly Leu Asn Ala Phe Phe Asn Pro Met Lys
                405                 410                 415 gca gac gtt gat tag                                                  1263
Ala Asp Val Asp
            420

<210> SEQ ID NO 16
<211> LENGTH: 420
<212> TYPE: PRT
<213> ORGANISM: Streptococcus mutans

<400> SEQUENCE: 16

Met Lys Trp Tyr Lys Lys Ile Gly Leu Leu Gly Ile Val Gly Leu Thr
1               5                   10                  15

Ser Val Leu Leu Ala Ala Cys Asn Lys Ser Lys Ala Ser Gln Ser Lys
                20                  25                  30

Glu Asp Lys Val Thr Ile Glu Tyr Phe Asn Gln Lys Lys Glu Met Asp
            35                  40                  45

Ala Thr Leu Lys Lys Ile Ile Lys Asp Phe Glu Arg Glu Asn Pro Lys
        50                  55                  60

Ile His Val Lys Met Thr Ser Val Pro Asp Ala Gly Thr Val Leu Lys
65                  70                  75                  80

Thr Arg Val Leu Ser Gly Asp Val Pro Asp Val Ile Asn Ile Tyr Pro
                85                  90                  95

Gln Asn Met Asp Phe Gln Glu Trp Ser Lys Ala Gly Tyr Phe Tyr Asn
            100                 105                 110

Met Thr Gly Lys Ala Tyr Leu Asn His Leu Lys Asn His Tyr Ala Asn
        115                 120                 125

Glu Tyr Lys Val Asn Gln Lys Val Tyr Ser Val Pro Leu Thr Ala Asn
    130                 135                 140

Val Ser Gly Ile Tyr Tyr Asn Lys Thr Lys Phe Lys Glu Leu Gly Leu
145                 150                 155                 160

Lys Val Pro Glu Thr Trp Asp Glu Phe Val Lys Leu Val Glu Glu Ile
                165                 170                 175

Lys Ala Lys Lys Glu Thr Pro Phe Ala Leu Ala Gly Thr Glu Gly Trp
            180                 185                 190

Thr Leu Asn Gly Tyr His Gln Leu Ser Leu Ile Ser Val Thr Gly Ser
        195                 200                 205

Ala Asn Ala Ala Asn Lys Tyr Leu Arg Phe Ser Gln Pro Asn Ser Ile
```

```
            210                 215                 220
Lys Thr Ser Asp Lys Ile Leu Lys Glu Asp Met Val Arg Leu Asn Leu
225                 230                 235                 240

Leu Ala Asp Asp Gly Asn Gln Gln Lys Asn Trp Lys Gly Ala Ser Tyr
                245                 250                 255

Asn Asp Ala Leu Val Ala Phe Ala Asn Glu Lys Ala Leu Met Thr Pro
                    260                 265                 270

Asn Gly Ser Trp Ala Leu Pro Ala Ile Lys Gln Gln Asp Pro Lys Phe
            275                 280                 285

Glu Ile Gly Thr Phe Ala Phe Pro Gly Lys Lys Thr Gly Asn Gly Ile
        290                 295                 300

Thr Val Gly Ala Gly Asp Leu Ala Leu Ser Ile Ser Ala Lys Thr Lys
305                 310                 315                 320

His Leu Lys Glu Ala Glu Lys Phe Val Lys Tyr Met Thr Thr Ala Arg
                325                 330                 335

Ala Met Gln Lys Tyr Tyr Asp Val Asp Gly Ser Pro Val Ala Val Lys
                    340                 345                 350

Gly Val Arg Glu Asp Lys Asn Ser Pro Leu Gln Pro Leu Thr Lys Leu
            355                 360                 365

Ala Phe Thr Asp Lys His Tyr Val Trp Leu Gly Gln His Trp Asn Ser
        370                 375                 380

Glu Asp Asp Phe Phe Thr Ala Thr Thr Asn Tyr Leu Met Thr Lys Asn
385                 390                 395                 400

Ala Lys Gly Leu Ala Asp Gly Leu Asn Ala Phe Phe Asn Pro Met Lys
                405                 410                 415

Ala Asp Val Asp
            420

<210> SEQ ID NO 17
<211> LENGTH: 873
<212> TYPE: DNA
<213> ORGANISM: Streptococcus mutans
<220> FEATURE:
<221> NAME/KEY: CDS
<222> LOCATION: (1)..(873)

<400> SEQUENCE: 17 atg act atc aga aaa gtt tta aat aaa tac tgg ggt tgg aca ttt tta     48
Met Thr Ile Arg Lys Val Leu Asn Lys Tyr Trp Gly Trp Thr Phe Leu
1               5                   10                  15 atc gta ccg ctc att tta caa gtt gta ttc ttt tat ttt cct atg ttt     96
Ile Val Pro Leu Ile Leu Gln Val Val Phe Phe Tyr Phe Pro Met Phe
            20                  25                  30 cag ggt gct ttt tat agc ttt act aat tgg aca ggt ctg acc tat aat    144
Gln Gly Ala Phe Tyr Ser Phe Thr Asn Trp Thr Gly Leu Thr Tyr Asn
        35                  40                  45 ttt gat ttt gtt ggt att aat aat tat aag att ttg atg act gat ggg    192
Phe Asp Phe Val Gly Ile Asn Asn Tyr Lys Ile Leu Met Thr Asp Gly
    50                  55                  60 aaa ttt atg aag gct att ggt ttt act ttg gtt ttg act ctg gcc ttg    240
Lys Phe Met Lys Ala Ile Gly Phe Thr Leu Val Leu Thr Leu Ala Leu
65                  70                  75                  80 att gtc ggt gaa att gtc ctt ggt att atc att gca cgt gcg ctt aat    288
Ile Val Gly Glu Ile Val Leu Gly Ile Ile Ile Ala Arg Ala Leu Asn
                85                  90                  95 gct aag atc aaa gga aaa act ttt ttc aga gcc tgg ttc ttc ttt cca    336
Ala Lys Ile Lys Gly Lys Thr Phe Phe Arg Ala Trp Phe Phe Phe Pro
            100                 105                 110
```

```
gct gtt tta tct ggt ttg aca gtt tct ttg att ttt aaa cag gtt ttc      384
Ala Val Leu Ser Gly Leu Thr Val Ser Leu Ile Phe Lys Gln Val Phe
        115                 120                 125 aat tat ggt ttg cca gca gtt ggc agt gct ttg gga att aaa ttt tta      432
Asn Tyr Gly Leu Pro Ala Val Gly Ser Ala Leu Gly Ile Lys Phe Leu
    130                 135                 140 gaa aca agt atg ttg gga aca gcg aac ggg gcg gtt att gct tca atc      480
Glu Thr Ser Met Leu Gly Thr Ala Asn Gly Ala Val Ile Ala Ser Ile
145                 150                 155                 160 ttt gtt ctt ttg tgg caa ggt gtt gct atg cct att att ctt ttc ctt      528
Phe Val Leu Leu Trp Gln Gly Val Ala Met Pro Ile Ile Leu Phe Leu
                165                 170                 175 tca gga tta cag agt att cca tca gag att gtc gaa gca gca gct att      576
Ser Gly Leu Gln Ser Ile Pro Ser Glu Ile Val Glu Ala Ala Ala Ile
            180                 185                 190 gat ggt gct gac agt aaa cag aca ttt tgg tca gtc gag ttg ccc tac      624
Asp Gly Ala Asp Ser Lys Gln Thr Phe Trp Ser Val Glu Leu Pro Tyr
        195                 200                 205 tta ctg cca agt att tcc atg gtt ttc atc atg gct tta aaa gct ggt      672
Leu Leu Pro Ser Ile Ser Met Val Phe Ile Met Ala Leu Lys Ala Gly
    210                 215                 220 ctt acg gcc ttt gat caa atc ttt gcc tta aca ggt ggc ggt cca aat      720
Leu Thr Ala Phe Asp Gln Ile Phe Ala Leu Thr Gly Gly Gly Pro Asn
225                 230                 235                 240 aat tca aca aca tca tta ggc ctt ttg gtt tat aac tat gcc ttt aag      768
Asn Ser Thr Thr Ser Leu Gly Leu Leu Val Tyr Asn Tyr Ala Phe Lys
                245                 250                 255 agt aat cag tat ggt tat gct aat gct att gct ttg att tta ttc att      816
Ser Asn Gln Tyr Gly Tyr Ala Asn Ala Ile Ala Leu Ile Leu Phe Ile
            260                 265                 270 atc att gga att gtt tct gtg ctg caa att aaa ctc tct aag aag ttt      864
Ile Ile Gly Ile Val Ser Val Leu Gln Ile Lys Leu Ser Lys Lys Phe
        275                 280                 285 gaa gtt tag                                                          873
Glu Val
    290

<210> SEQ ID NO 18
<211> LENGTH: 290
<212> TYPE: PRT
<213> ORGANISM: Streptococcus mutans

<400> SEQUENCE: 18

Met Thr Ile Arg Lys Val Leu Asn Lys Tyr Trp Gly Trp Thr Phe Leu
1               5                   10                  15

Ile Val Pro Leu Ile Leu Gln Val Phe Phe Tyr Phe Pro Met Phe
            20                  25                  30

Gln Gly Ala Phe Tyr Ser Phe Thr Asn Trp Thr Gly Leu Thr Tyr Asn
        35                  40                  45

Phe Asp Phe Val Gly Ile Asn Asn Tyr Lys Ile Leu Met Thr Asp Gly
    50                  55                  60

Lys Phe Met Lys Ala Ile Gly Phe Thr Leu Val Leu Thr Leu Ala Leu
65                  70                  75                  80

Ile Val Gly Glu Ile Val Leu Gly Ile Ile Ala Arg Ala Leu Asn
                85                  90                  95

Ala Lys Ile Lys Gly Lys Thr Phe Phe Arg Ala Trp Phe Phe Pro
            100                 105                 110

Ala Val Leu Ser Gly Leu Thr Val Ser Leu Ile Phe Lys Gln Val Phe
```

```
                115                 120                 125
Asn Tyr Gly Leu Pro Ala Val Gly Ser Ala Leu Gly Ile Lys Phe Leu
            130                 135                 140

Glu Thr Ser Met Leu Gly Thr Ala Asn Gly Ala Val Ile Ala Ser Ile
145                 150                 155                 160

Phe Val Leu Leu Trp Gln Gly Val Ala Met Pro Ile Ile Leu Phe Leu
                165                 170                 175

Ser Gly Leu Gln Ser Ile Pro Ser Glu Ile Val Glu Ala Ala Ala Ile
            180                 185                 190

Asp Gly Ala Asp Ser Lys Gln Thr Phe Trp Ser Val Glu Leu Pro Tyr
        195                 200                 205

Leu Leu Pro Ser Ile Ser Met Val Phe Ile Met Ala Leu Lys Ala Gly
210                 215                 220

Leu Thr Ala Phe Asp Gln Ile Phe Ala Leu Thr Gly Gly Gly Pro Asn
225                 230                 235                 240

Asn Ser Thr Thr Ser Leu Gly Leu Leu Val Tyr Asn Tyr Ala Phe Lys
                245                 250                 255

Ser Asn Gln Tyr Gly Tyr Ala Asn Ala Ile Ala Leu Ile Leu Phe Ile
            260                 265                 270

Ile Ile Gly Ile Val Ser Val Leu Gln Ile Lys Leu Ser Lys Lys Phe
        275                 280                 285

Glu Val
    290

<210> SEQ ID NO 19
<211> LENGTH: 834
<212> TYPE: DNA
<213> ORGANISM: Streptococcus mutans
<220> FEATURE:
<221> NAME/KEY: CDS
<222> LOCATION: (1)..(834)

<400> SEQUENCE: 19 atg aaa aaa gaa gaa aaa ata aat tat ttt tgg aaa tat gta ctt ttg      48
Met Lys Lys Glu Glu Lys Ile Asn Tyr Phe Trp Lys Tyr Val Leu Leu
1               5                   10                  15 act gtt ggt ggc atc ctg att ttg atc cca ctg atg gtt act gtc ttt      96
Thr Val Gly Gly Ile Leu Ile Leu Ile Pro Leu Met Val Thr Val Phe
            20                  25                  30 agc tct ttt aag aaa act aag gat att atg aat cat ttt ttt gcc ttt     144
Ser Ser Phe Lys Lys Thr Lys Asp Ile Met Asn His Phe Phe Ala Phe
        35                  40                  45 cca aat cct atc acc ttg gat aat tac aaa cgt ttg tta gct gat ggt     192
Pro Asn Pro Ile Thr Leu Asp Asn Tyr Lys Arg Leu Leu Ala Asp Gly
    50                  55                  60 gtt gga ggc tat ttt tgg aat tca acg gtg att act gtt tta tcc gtt     240
Val Gly Gly Tyr Phe Trp Asn Ser Thr Val Ile Thr Val Leu Ser Val
65                  70                  75                  80 ttg gtg gtc atg ctc ttt atc cct gca gcg gct tat tcc att gcg cgt     288
Leu Val Val Met Leu Phe Ile Pro Ala Ala Ala Tyr Ser Ile Ala Arg
                85                  90                  95 aac atg tct aga aga aaa gct ttc aat atc atg tat agc ctg ttg att     336
Asn Met Ser Arg Arg Lys Ala Phe Asn Ile Met Tyr Ser Leu Leu Ile
            100                 105                 110 ctg gga att ttc gtt cct ttc cag gtt atc atg att cct att acg gtt     384
Leu Gly Ile Phe Val Pro Phe Gln Val Ile Met Ile Pro Ile Thr Val
        115                 120                 125 atg atg agt aaa tta ggc ctg gct aat atg tgg gga tta att att ctg     432
```

```
Met Met Ser Lys Leu Gly Leu Ala Asn Met Trp Gly Leu Ile Ile Leu
        130                 135                 140 tat tta act tat gct att cca cag aca ctc ttc ctt tac gtg ggt tat      480
Tyr Leu Thr Tyr Ala Ile Pro Gln Thr Leu Phe Leu Tyr Val Gly Tyr
145                 150                 155                 160 atc aaa cta agt gta cct gat agt tta gat gaa gca gct gaa att gat      528
Ile Lys Leu Ser Val Pro Asp Ser Leu Asp Glu Ala Ala Glu Ile Asp
                165                 170                 175 ggt gcg gat aaa ttg aca act tat cgt aaa atc att ttc cct atg tta      576
Gly Ala Asp Lys Leu Thr Thr Tyr Arg Lys Ile Ile Phe Pro Met Leu
        180                 185                 190 aaa cca atg cac gca aca act ctg att att aat gca ctt tgg ttc tgg      624
Lys Pro Met His Ala Thr Thr Leu Ile Ile Asn Ala Leu Trp Phe Trp
    195                 200                 205 aac gac ttt atg ttg cca ttg ctg att ctt aat aag gat tca agt atg      672
Asn Asp Phe Met Leu Pro Leu Leu Ile Leu Asn Lys Asp Ser Ser Met
210                 215                 220 tgg acg ctt cct ctt ttc caa tac aat tat agc gga caa tat ttc aat      720
Trp Thr Leu Pro Leu Phe Gln Tyr Asn Tyr Ser Gly Gln Tyr Phe Asn
225                 230                 235                 240 gat tac ggt cct agt ttt gct tct tac att gtt ggt att att acc att      768
Asp Tyr Gly Pro Ser Phe Ala Ser Tyr Ile Val Gly Ile Ile Thr Ile
                245                 250                 255 aca att gtt tat ctt att ttc caa aaa cac att att gct ggt atg agc      816
Thr Ile Val Tyr Leu Ile Phe Gln Lys His Ile Ile Ala Gly Met Ser
            260                 265                 270 aat gga gct gtg aag tga                                              834
Asn Gly Ala Val Lys
        275

<210> SEQ ID NO 20
<211> LENGTH: 277
<212> TYPE: PRT
<213> ORGANISM: Streptococcus mutans

<400> SEQUENCE: 20

Met Lys Lys Glu Glu Lys Ile Asn Tyr Phe Trp Lys Tyr Val Leu Leu
1               5                   10                  15

Thr Val Gly Gly Ile Leu Ile Leu Ile Pro Leu Met Val Thr Val Phe
            20                  25                  30

Ser Ser Phe Lys Lys Thr Lys Asp Ile Met Asn His Phe Phe Ala Phe
        35                  40                  45

Pro Asn Pro Ile Thr Leu Asp Asn Tyr Lys Arg Leu Leu Ala Asp Gly
    50                  55                  60

Val Gly Gly Tyr Phe Trp Asn Ser Thr Val Ile Thr Val Leu Ser Val
65                  70                  75                  80

Leu Val Val Met Leu Phe Ile Pro Ala Ala Tyr Ser Ile Ala Arg
                85                  90                  95

Asn Met Ser Arg Arg Lys Ala Phe Asn Ile Met Tyr Ser Leu Leu Ile
            100                 105                 110

Leu Gly Ile Phe Val Pro Phe Gln Val Ile Met Ile Pro Ile Thr Val
        115                 120                 125

Met Met Ser Lys Leu Gly Leu Ala Asn Met Trp Gly Leu Ile Ile Leu
    130                 135                 140

Tyr Leu Thr Tyr Ala Ile Pro Gln Thr Leu Phe Leu Tyr Val Gly Tyr
145                 150                 155                 160

Ile Lys Leu Ser Val Pro Asp Ser Leu Asp Glu Ala Ala Glu Ile Asp
                165                 170                 175
```

-continued

```
Gly Ala Asp Lys Leu Thr Thr Tyr Arg Lys Ile Ile Phe Pro Met Leu
            180                 185                 190

Lys Pro Met His Ala Thr Thr Leu Ile Ile Asn Ala Leu Trp Phe Trp
        195                 200                 205

Asn Asp Phe Met Leu Pro Leu Leu Ile Leu Asn Lys Asp Ser Ser Met
    210                 215                 220

Trp Thr Leu Pro Leu Phe Gln Tyr Asn Tyr Ser Gly Gln Tyr Phe Asn
225                 230                 235                 240

Asp Tyr Gly Pro Ser Phe Ala Ser Tyr Ile Val Gly Ile Ile Thr Ile
                245                 250                 255

Thr Ile Val Tyr Leu Ile Phe Gln Lys His Ile Ile Ala Gly Met Ser
            260                 265                 270

Asn Gly Ala Val Lys
        275

<210> SEQ ID NO 21
<211> LENGTH: 1854
<212> TYPE: DNA
<213> ORGANISM: Saccharomyces cerevisiae
<220> FEATURE:
<221> NAME/KEY: CDS
<222> LOCATION: (1)..(1854)

<400> SEQUENCE: 21 atg aaa aat atc att tca ttg gta agc aag aag aag gct gcc tca aaa        48
Met Lys Asn Ile Ile Ser Leu Val Ser Lys Lys Lys Ala Ala Ser Lys
1               5                   10                  15 aat gag gat aaa aac att tct gag tct tca aga gat att gta aac caa        96
Asn Glu Asp Lys Asn Ile Ser Glu Ser Ser Arg Asp Ile Val Asn Gln
            20                  25                  30 cag gag gtt ttc aat act gaa gat ttt gaa gaa ggg aaa aag gat agt       144
Gln Glu Val Phe Asn Thr Glu Asp Phe Glu Glu Gly Lys Lys Asp Ser
        35                  40                  45 gcc ttt gag cta gac cac tta gag ttc acc acc aat tca gcc cag tta       192
Ala Phe Glu Leu Asp His Leu Glu Phe Thr Thr Asn Ser Ala Gln Leu
    50                  55                  60 gga gat tct gac gaa gat aac gag aat gtg att aat gag atg aac gct       240
Gly Asp Ser Asp Glu Asp Asn Glu Asn Val Ile Asn Glu Met Asn Ala
65                  70                  75                  80 act gat gat gca aat gaa gct aac agc gag gaa aaa agc atg act ttg       288
Thr Asp Asp Ala Asn Glu Ala Asn Ser Glu Glu Lys Ser Met Thr Leu
                85                  90                  95 aag cag gcg ttg cta aaa tat cca aaa gca gcc ctg tgg tcc ata tta       336
Lys Gln Ala Leu Leu Lys Tyr Pro Lys Ala Ala Leu Trp Ser Ile Leu
            100                 105                 110 gtg tct act acc ctg gtt atg gaa ggt tat gat acc gca cta ctg agc       384
Val Ser Thr Thr Leu Val Met Glu Gly Tyr Asp Thr Ala Leu Leu Ser
        115                 120                 125 gca ctg tat gcc ctg cca gtt ttt cag aga aaa ttc ggt act ttg aac       432
Ala Leu Tyr Ala Leu Pro Val Phe Gln Arg Lys Phe Gly Thr Leu Asn
    130                 135                 140 ggg gag ggt tct tac gaa att act tcc caa tgg cag att ggt tta aac       480
Gly Glu Gly Ser Tyr Glu Ile Thr Ser Gln Trp Gln Ile Gly Leu Asn
145                 150                 155                 160 atg tgt gtc ctt tgt ggt gag atg att ggt ttg caa atc acg act tat       528
Met Cys Val Leu Cys Gly Glu Met Ile Gly Leu Gln Ile Thr Thr Tyr
                165                 170                 175 atg gtt gaa ttt atg ggg aat cgt tat acg atg att aca gca ctt ggt       576
Met Val Glu Phe Met Gly Asn Arg Tyr Thr Met Ile Thr Ala Leu Gly
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     |     | 180 |     |     |     |     | 185 |     |     |     |     | 190 |     |     |     |
| ttg | tta | act | gct | tat | atc | ttt | atc | ctc | tac | tac | tgt | aaa | agt | tta | gct | 624 |
| Leu | Leu | Thr | Ala | Tyr | Ile | Phe | Ile | Leu | Tyr | Tyr | Cys | Lys | Ser | Leu | Ala |     |
|     |     | 195 |     |     |     |     | 200 |     |     |     |     | 205 |     |     |     |     |
| atg | att | gct | gtg | gga | caa | att | ctc | tca | gct | ata | cca | tgg | ggt | tgt | ttc | 672 |
| Met | Ile | Ala | Val | Gly | Gln | Ile | Leu | Ser | Ala | Ile | Pro | Trp | Gly | Cys | Phe |     |
| 210 |     |     |     |     | 215 |     |     |     |     | 220 |     |     |     |     |     |     |
| caa | agt | ttg | gct | gtt | act | tat | gct | tcg | gaa | gtt | tgc | cct | tta | gca | tta | 720 |
| Gln | Ser | Leu | Ala | Val | Thr | Tyr | Ala | Ser | Glu | Val | Cys | Pro | Leu | Ala | Leu |     |
| 225 |     |     |     |     | 230 |     |     |     |     | 235 |     |     |     |     | 240 |     |
| aga | tat | tac | atg | acc | agt | tac | tcc | aac | att | tgt | tgg | tta | ttt | ggt | caa | 768 |
| Arg | Tyr | Tyr | Met | Thr | Ser | Tyr | Ser | Asn | Ile | Cys | Trp | Leu | Phe | Gly | Gln |     |
|     |     |     |     | 245 |     |     |     |     | 250 |     |     |     |     | 255 |     |     |
| atc | ttc | gcc | tct | ggt | att | atg | aaa | aac | tca | caa | gag | aat | tta | ggg | aac | 816 |
| Ile | Phe | Ala | Ser | Gly | Ile | Met | Lys | Asn | Ser | Gln | Glu | Asn | Leu | Gly | Asn |     |
|     |     |     | 260 |     |     |     |     | 265 |     |     |     |     | 270 |     |     |     |
| tcc | gac | ttg | ggc | tat | aaa | ttg | cca | ttt | gct | tta | caa | tgg | att | tgg | cct | 864 |
| Ser | Asp | Leu | Gly | Tyr | Lys | Leu | Pro | Phe | Ala | Leu | Gln | Trp | Ile | Trp | Pro |     |
|     |     | 275 |     |     |     |     | 280 |     |     |     |     | 285 |     |     |     |     |
| gct | cct | tta | atg | atc | ggt | atc | ttt | ttc | gct | cct | gag | tcg | ccc | tgg | tgg | 912 |
| Ala | Pro | Leu | Met | Ile | Gly | Ile | Phe | Phe | Ala | Pro | Glu | Ser | Pro | Trp | Trp |     |
|     | 290 |     |     |     |     | 295 |     |     |     |     | 300 |     |     |     |     |     |
| ttg | gtg | aga | aag | gat | agg | gtc | gct | gag | gca | aga | aaa | tct | tta | agc | aga | 960 |
| Leu | Val | Arg | Lys | Asp | Arg | Val | Ala | Glu | Ala | Arg | Lys | Ser | Leu | Ser | Arg |     |
| 305 |     |     |     |     | 310 |     |     |     |     | 315 |     |     |     |     | 320 |     |
| att | ttg | agt | ggt | aaa | ggc | gcc | gag | aag | gac | att | caa | gtt | gat | ctt | act | 1008 |
| Ile | Leu | Ser | Gly | Lys | Gly | Ala | Glu | Lys | Asp | Ile | Gln | Val | Asp | Leu | Thr |     |
|     |     |     |     | 325 |     |     |     |     | 330 |     |     |     |     | 335 |     |     |
| tta | aag | cag | att | gaa | ttg | act | att | gaa | aaa | gaa | aga | ctt | tta | gca | tct | 1056 |
| Leu | Lys | Gln | Ile | Glu | Leu | Thr | Ile | Glu | Lys | Glu | Arg | Leu | Leu | Ala | Ser |     |
|     |     |     | 340 |     |     |     |     | 345 |     |     |     |     | 350 |     |     |     |
| aaa | tca | gga | tca | ttc | ttt | aat | tgt | ttc | aag | gga | gtt | aat | gga | aga | aga | 1104 |
| Lys | Ser | Gly | Ser | Phe | Phe | Asn | Cys | Phe | Lys | Gly | Val | Asn | Gly | Arg | Arg |     |
|     |     | 355 |     |     |     |     | 360 |     |     |     |     | 365 |     |     |     |     |
| acg | aga | ctt | gca | tgt | tta | act | tgg | gta | gct | caa | aat | agt | agc | ggt | gcc | 1152 |
| Thr | Arg | Leu | Ala | Cys | Leu | Thr | Trp | Val | Ala | Gln | Asn | Ser | Ser | Gly | Ala |     |
|     | 370 |     |     |     |     | 375 |     |     |     |     | 380 |     |     |     |     |     |
| gtt | tta | ctt | ggt | tac | tcg | aca | tat | ttt | ttt | gaa | aag | aag | cag | gta | atg | 1200 |
| Val | Leu | Leu | Gly | Tyr | Ser | Thr | Tyr | Phe | Phe | Glu | Lys | Lys | Gln | Val | Met |     |
| 385 |     |     |     |     | 390 |     |     |     |     | 395 |     |     |     |     | 400 |     |
| gcc | acc | gac | aag | gcg | ttt | act | ttt | tct | cta | att | cag | tac | tgt | ctt | ggg | 1248 |
| Ala | Thr | Asp | Lys | Ala | Phe | Thr | Phe | Ser | Leu | Ile | Gln | Tyr | Cys | Leu | Gly |     |
|     |     |     |     | 405 |     |     |     |     | 410 |     |     |     |     | 415 |     |     |
| tta | gcg | ggt | aca | ctt | tgc | tcc | tgg | gta | ata | tct | ggc | cgt | gtt | ggt | aga | 1296 |
| Leu | Ala | Gly | Thr | Leu | Cys | Ser | Trp | Val | Ile | Ser | Gly | Arg | Val | Gly | Arg |     |
|     |     |     | 420 |     |     |     |     | 425 |     |     |     |     | 430 |     |     |     |
| tgg | aca | ata | ctg | acc | tat | ggt | ctt | gca | ttt | caa | atg | gtc | tgc | tta | ttt | 1344 |
| Trp | Thr | Ile | Leu | Thr | Tyr | Gly | Leu | Ala | Phe | Gln | Met | Val | Cys | Leu | Phe |     |
|     |     | 435 |     |     |     |     | 440 |     |     |     |     | 445 |     |     |     |     |
| att | att | ggt | gga | atg | ggt | ttt | ggt | tct | gga | agc | agc | gct | agt | aat | ggt | 1392 |
| Ile | Ile | Gly | Gly | Met | Gly | Phe | Gly | Ser | Gly | Ser | Ser | Ala | Ser | Asn | Gly |     |
|     | 450 |     |     |     |     | 455 |     |     |     |     | 460 |     |     |     |     |     |
| gcc | ggt | ggt | tta | ttg | ctg | gct | tta | tca | ttc | ttt | tac | aat | gct | ggt | atc | 1440 |
| Ala | Gly | Gly | Leu | Leu | Leu | Ala | Leu | Ser | Phe | Phe | Tyr | Asn | Ala | Gly | Ile |     |
| 465 |     |     |     |     | 470 |     |     |     |     | 475 |     |     |     |     | 480 |     |
| ggt | gca | gtt | gtt | tac | tgt | atc | gtt | gct | gaa | att | cca | tca | gcg | gag | ttg | 1488 |
| Gly | Ala | Val | Val | Tyr | Cys | Ile | Val | Ala | Glu | Ile | Pro | Ser | Ala | Glu | Leu |     |
|     |     |     |     | 485 |     |     |     |     | 490 |     |     |     |     | 495 |     |     |
| aga | act | aag | act | ata | gtg | ctg | gcc | cgt | att | tgc | tac | aat | ctc | atg | gcc | 1536 |

```
                Arg Thr Lys Thr Ile Val Leu Ala Arg Ile Cys Tyr Asn Leu Met Ala
                                500                 505                 510 gtt att aac gct ata tta acg ccc tat atg cta aac gtg agc gat tgg          1584
Val Ile Asn Ala Ile Leu Thr Pro Tyr Met Leu Asn Val Ser Asp Trp
515                 520                 525 aac tgg ggt gcc aaa act ggt cta tac tgg ggt ggt ttc aca gca gtc          1632
Asn Trp Gly Ala Lys Thr Gly Leu Tyr Trp Gly Gly Phe Thr Ala Val
    530                 535                 540 act tta gct tgg gtc atc atc gat ctg cct gag aca act ggt aga acc          1680
Thr Leu Ala Trp Val Ile Ile Asp Leu Pro Glu Thr Thr Gly Arg Thr
545                 550                 555                 560 ttc agt gaa att aat gaa ctt ttc aac caa ggg gtt cct gcc aga aaa          1728
Phe Ser Glu Ile Asn Glu Leu Phe Asn Gln Gly Val Pro Ala Arg Lys
                565                 570                 575 ttt gca tct act gtg gtt gat cca ttc gga aag gga aaa act caa cat          1776
Phe Ala Ser Thr Val Val Asp Pro Phe Gly Lys Gly Lys Thr Gln His
            580                 585                 590 gat tcg cta gct gat gag agt atc agt cag tcc tca agc ata aaa cag          1824
Asp Ser Leu Ala Asp Glu Ser Ile Ser Gln Ser Ser Ser Ile Lys Gln
        595                 600                 605 cga gaa tta aat gca gct gat aaa tgt taa                                  1854
Arg Glu Leu Asn Ala Ala Asp Lys Cys
    610                 615

<210> SEQ ID NO 22
<211> LENGTH: 617
<212> TYPE: PRT
<213> ORGANISM: Saccharomyces cerevisiae

<400> SEQUENCE: 22

Met Lys Asn Ile Ile Ser Leu Val Ser Lys Lys Ala Ala Ser Lys
1               5                   10                  15

Asn Glu Asp Lys Asn Ile Ser Glu Ser Ser Arg Asp Ile Val Asn Gln
                20                  25                  30

Gln Glu Val Phe Asn Thr Glu Asp Phe Glu Gly Lys Lys Asp Ser
            35                  40                  45

Ala Phe Glu Leu Asp His Leu Glu Phe Thr Thr Asn Ser Ala Gln Leu
    50                  55                  60

Gly Asp Ser Asp Glu Asp Asn Glu Asn Val Ile Asn Glu Met Asn Ala
65                  70                  75                  80

Thr Asp Asp Ala Asn Glu Ala Asn Ser Glu Glu Lys Ser Met Thr Leu
                85                  90                  95

Lys Gln Ala Leu Leu Lys Tyr Pro Lys Ala Ala Leu Trp Ser Ile Leu
            100                 105                 110

Val Ser Thr Thr Leu Val Met Glu Gly Tyr Asp Thr Ala Leu Leu Ser
        115                 120                 125

Ala Leu Tyr Ala Leu Pro Val Phe Gln Arg Lys Phe Gly Thr Leu Asn
    130                 135                 140

Gly Glu Gly Ser Tyr Glu Ile Thr Ser Gln Trp Gln Ile Gly Leu Asn
145                 150                 155                 160

Met Cys Val Leu Cys Gly Glu Met Ile Gly Leu Gln Ile Thr Thr Tyr
                165                 170                 175

Met Val Glu Phe Met Gly Asn Arg Tyr Thr Met Ile Thr Ala Leu Gly
            180                 185                 190

Leu Leu Thr Ala Tyr Ile Phe Ile Leu Tyr Tyr Cys Lys Ser Leu Ala
        195                 200                 205

Met Ile Ala Val Gly Gln Ile Leu Ser Ala Ile Pro Trp Gly Cys Phe
```

```
            210                 215                 220
Gln Ser Leu Ala Val Thr Tyr Ala Ser Glu Val Cys Pro Leu Ala Leu
225                 230                 235                 240

Arg Tyr Tyr Met Thr Ser Tyr Ser Asn Ile Cys Trp Leu Phe Gly Gln
                245                 250                 255

Ile Phe Ala Ser Gly Ile Met Lys Asn Ser Gln Glu Asn Leu Gly Asn
                260                 265                 270

Ser Asp Leu Gly Tyr Lys Leu Pro Phe Ala Leu Gln Trp Ile Trp Pro
            275                 280                 285

Ala Pro Leu Met Ile Gly Ile Phe Ala Pro Glu Ser Pro Trp Trp
            290                 295                 300

Leu Val Arg Lys Asp Arg Val Ala Glu Ala Arg Lys Ser Leu Ser Arg
305                 310                 315                 320

Ile Leu Ser Gly Lys Gly Ala Glu Lys Asp Ile Gln Val Asp Leu Thr
                325                 330                 335

Leu Lys Gln Ile Glu Leu Thr Ile Glu Lys Glu Arg Leu Leu Ala Ser
                340                 345                 350

Lys Ser Gly Ser Phe Phe Asn Cys Phe Lys Gly Val Asn Gly Arg Arg
            355                 360                 365

Thr Arg Leu Ala Cys Leu Thr Trp Val Ala Gln Asn Ser Ser Gly Ala
370                 375                 380

Val Leu Leu Gly Tyr Ser Thr Tyr Phe Glu Lys Lys Gln Val Met
385                 390                 395                 400

Ala Thr Asp Lys Ala Phe Thr Phe Ser Leu Ile Gln Tyr Cys Leu Gly
                405                 410                 415

Leu Ala Gly Thr Leu Cys Ser Trp Val Ile Ser Gly Arg Val Gly Arg
            420                 425                 430

Trp Thr Ile Leu Thr Tyr Gly Leu Ala Phe Gln Met Val Cys Leu Phe
                435                 440                 445

Ile Ile Gly Gly Met Gly Phe Gly Ser Gly Ser Ser Ala Ser Asn Gly
            450                 455                 460

Ala Gly Gly Leu Leu Leu Ala Leu Ser Phe Phe Tyr Asn Ala Gly Ile
465                 470                 475                 480

Gly Ala Val Val Tyr Cys Ile Val Ala Glu Ile Pro Ser Ala Glu Leu
                485                 490                 495

Arg Thr Lys Thr Ile Val Leu Ala Arg Ile Cys Tyr Asn Leu Met Ala
                500                 505                 510

Val Ile Asn Ala Ile Leu Thr Pro Tyr Met Leu Asn Val Ser Asp Trp
            515                 520                 525

Asn Trp Gly Ala Lys Thr Gly Leu Tyr Trp Gly Gly Phe Thr Ala Val
530                 535                 540

Thr Leu Ala Trp Val Ile Ile Asp Leu Pro Glu Thr Thr Gly Arg Thr
545                 550                 555                 560

Phe Ser Glu Ile Asn Glu Leu Phe Asn Gln Gly Val Pro Ala Arg Lys
                565                 570                 575

Phe Ala Ser Thr Val Val Asp Pro Phe Gly Lys Gly Lys Thr Gln His
            580                 585                 590

Asp Ser Leu Ala Asp Glu Ser Ile Ser Gln Ser Ser Ile Lys Gln
            595                 600                 605

Arg Glu Leu Asn Ala Ala Asp Lys Cys
            610                 615

<210> SEQ ID NO 23
```

```
<211> LENGTH: 20
<212> TYPE: DNA
<213> ORGANISM: Artificial Sequence
<220> FEATURE:
<223> OTHER INFORMATION: primer

<400> SEQUENCE: 23
agaaatttcc cgctctatgg                                               20

<210> SEQ ID NO 24
<211> LENGTH: 22
<212> TYPE: DNA
<213> ORGANISM: Artificial Sequence
<220> FEATURE:
<223> OTHER INFORMATION: primer

<400> SEQUENCE: 24
tgtagtgctg attgatcagt tc                                            22

<210> SEQ ID NO 25
<211> LENGTH: 35
<212> TYPE: DNA
<213> ORGANISM: Artificial Sequence
<220> FEATURE:
<223> OTHER INFORMATION: primer

<400> SEQUENCE: 25
gccaagcttg catgcctgca ggtcgactct agagg                              35

<210> SEQ ID NO 26
<211> LENGTH: 32
<212> TYPE: DNA
<213> ORGANISM: Artificial Sequence
<220> FEATURE:
<223> OTHER INFORMATION: primer

<400> SEQUENCE: 26
cccaagcttg ctaactcaca ttaattgcgt tg                                 32

<210> SEQ ID NO 27
<211> LENGTH: 43
<212> TYPE: DNA
<213> ORGANISM: Artificial Sequence
<220> FEATURE:
<223> OTHER INFORMATION: primer

<400> SEQUENCE: 27
caatttcaca caaggagact gccatgatgc aaaaaattca gcg                     43

<210> SEQ ID NO 28
<211> LENGTH: 31
<212> TYPE: DNA
<213> ORGANISM: Artificial Sequence
<220> FEATURE:
<223> OTHER INFORMATION: primer

<400> SEQUENCE: 28
cccaagcttc ccctttttac tcgattgtct c                                  31

<210> SEQ ID NO 29
<211> LENGTH: 80
<212> TYPE: DNA
<213> ORGANISM: Artificial Sequence
<220> FEATURE:
<223> OTHER INFORMATION: primer

<400> SEQUENCE: 29
```

```
cccaagcttc ctgttgacaa ttaatcatcg gctcgaataa tgtgtggaat cgtgagcgga    60
taacaatttc acacaaggag                                                80
```

<210> SEQ ID NO 30
<211> LENGTH: 31
<212> TYPE: DNA
<213> ORGANISM: Artificial Sequence
<220> FEATURE:
<223> OTHER INFORMATION: primer

<400> SEQUENCE: 30

```
cccaagcttc cccttttttac tcgattgtct c                                  31
```

<210> SEQ ID NO 31
<211> LENGTH: 80
<212> TYPE: DNA
<213> ORGANISM: Artificial Sequence
<220> FEATURE:
<223> OTHER INFORMATION: primer

<400> SEQUENCE: 31

```
cgaataatgt gtggaatcgt gagcggataa caatttcaca caaggagact gccatgatgc    60
aaaaaattca gcgctttgga                                                80
```

<210> SEQ ID NO 32
<211> LENGTH: 44
<212> TYPE: DNA
<213> ORGANISM: Artificial Sequence
<220> FEATURE:
<223> OTHER INFORMATION: tac promoter

<400> SEQUENCE: 32

```
ccctgttgac aattaatcat cggctcgtat aatgtgtgga atcg                     44
```

<210> SEQ ID NO 33
<211> LENGTH: 44
<212> TYPE: DNA
<213> ORGANISM: Artificial Sequence
<220> FEATURE:
<223> OTHER INFORMATION: PTacA promoter

<400> SEQUENCE: 33

```
ccctgttgac aattaatcat cggctcgaat aatgtgtgga atcg                     44
```

<210> SEQ ID NO 34
<211> LENGTH: 80
<212> TYPE: DNA
<213> ORGANISM: Artificial Sequence
<220> FEATURE:
<223> OTHER INFORMATION: primer

<400> SEQUENCE: 34

```
gaatcgtgag cggataacaa tttcacacaa ggagactgcc atgatgcaaa aaattcagcg    60
ctttggaagc gcgatgtttg                                                80
```

<210> SEQ ID NO 35
<211> LENGTH: 22
<212> TYPE: DNA
<213> ORGANISM: Artificial Sequence
<220> FEATURE:
<223> OTHER INFORMATION: primer

<400> SEQUENCE: 35
tgacggcaaa cgaaaaccct cc                                                    22

<210> SEQ ID NO 36
<211> LENGTH: 47
<212> TYPE: DNA
<213> ORGANISM: Artificial Sequence
<220> FEATURE:
<223> OTHER INFORMATION: primer

<400> SEQUENCE: 36
gctctagagc ccctgttgga attaatcatc ggctcgtata atgtgtg                         47

<210> SEQ ID NO 37
<211> LENGTH: 40
<212> TYPE: DNA
<213> ORGANISM: Artificial Sequence
<220> FEATURE:
<223> OTHER INFORMATION: primer

<400> SEQUENCE: 37
gctctagagc tgacggcaaa cgaaaaccct cccgaaaagg                                 40

<210> SEQ ID NO 38
<211> LENGTH: 77
<212> TYPE: DNA
<213> ORGANISM: Artificial Sequence
<220> FEATURE:
<223> OTHER INFORMATION: primer

<400> SEQUENCE: 38
ccctgttgga attaatcatc ggctcgtata atgtgtggaa tcgtgagcgg ataacaattt           60
cacacaagga gactgcc                                                          77

<210> SEQ ID NO 39
<211> LENGTH: 1350
<212> TYPE: DNA
<213> ORGANISM: Bacillus subtilis
<220> FEATURE:
<221> NAME/KEY: CDS
<222> LOCATION: (1)..(1350)

<400> SEQUENCE: 39

```
atg aag aaa aaa tca ttc tca atc gta ata gcg ggc gga ggg agc act           48
Met Lys Lys Lys Ser Phe Ser Ile Val Ile Ala Gly Gly Gly Ser Thr
1               5                   10                  15 ttc act cca ggg atc gta ctc atg ctc ttg gac cat ttg gag gag ttt           96
Phe Thr Pro Gly Ile Val Leu Met Leu Leu Asp His Leu Glu Glu Phe
                20                  25                  30 ccg atc aga aag ctg aag ctg tat gat aat gat aag gag aga cag gat          144
Pro Ile Arg Lys Leu Lys Leu Tyr Asp Asn Asp Lys Glu Arg Gln Asp
            35                  40                  45 cga att gca ggc gcc tgt gac gtt ttt atc aga gaa aaa gcg ccg gat          192
Arg Ile Ala Gly Ala Cys Asp Val Phe Ile Arg Glu Lys Ala Pro Asp
        50                  55                  60 att gaa ttt gca gcg acg act gac ccg gaa gaa gct ttt aca gat gtc          240
Ile Glu Phe Ala Ala Thr Thr Asp Pro Glu Glu Ala Phe Thr Asp Val
65                  70                  75                  80 gat ttt gtt atg gcg cac atc aga gta ggg aaa tac gcg atg cgc gcg          288
Asp Phe Val Met Ala His Ile Arg Val Gly Lys Tyr Ala Met Arg Ala
                85                  90                  95 ctt gat gag caa att ccg tta aag tac gga gtt gtc ggc cag gag acg          336
Leu Asp Glu Gln Ile Pro Leu Lys Tyr Gly Val Val Gly Gln Glu Thr
                100                 105                 110
```

-continued

| | | |
|---|---|---|
| tgc ggg ccg ggc ggg atc gca tac ggt atg cgt tcg atc ggc ggt gtg<br>Cys Gly Pro Gly Gly Ile Ala Tyr Gly Met Arg Ser Ile Gly Gly Val<br>115                    120                    125 | 384 |
| ctt gaa ata tta gat tac atg gaa aaa tac tcg cct gat gcg tgg atg<br>Leu Glu Ile Leu Asp Tyr Met Glu Lys Tyr Ser Pro Asp Ala Trp Met<br>     130                    135                    140 | 432 |
| ctc aat tat tcc aat ccg gcg gca att gtg gct gaa gct acg aga cgc<br>Leu Asn Tyr Ser Asn Pro Ala Ala Ile Val Ala Glu Ala Thr Arg Arg<br>145                    150                    155                    160 | 480 |
| ctt aga ccg aat tct aaa att ctc aat atc tgt gat atg ccg gtt ggg<br>Leu Arg Pro Asn Ser Lys Ile Leu Asn Ile Cys Asp Met Pro Val Gly<br>                  165                    170                    175 | 528 |
| atc gaa gac cgg atg gcg caa att ctt ggc tta tcc tca aga aaa gaa<br>Ile Glu Asp Arg Met Ala Gln Ile Leu Gly Leu Ser Ser Arg Lys Glu<br>                180                    185                    190 | 576 |
| atg aag gtc cgc tat tac gga ttg aat cat ttc ggc tgg tgg aca tcg<br>Met Lys Val Arg Tyr Tyr Gly Leu Asn His Phe Gly Trp Trp Thr Ser<br>              195                    200                    205 | 624 |
| att cag gat caa gag ggc aac gat tta atg ccg aag ctg aag gaa cat<br>Ile Gln Asp Gln Glu Gly Asn Asp Leu Met Pro Lys Leu Lys Glu His<br>     210                    215                    220 | 672 |
| gta tcc caa tac ggt tat att ccg aaa aca gag gct gaa gct gtg gag<br>Val Ser Gln Tyr Gly Tyr Ile Pro Lys Thr Glu Ala Glu Ala Val Glu<br>225                    230                    235                    240 | 720 |
| gca agc tgg aat gac acg ttc gcc aaa gcg cgt gac gtg cag gct gca<br>Ala Ser Trp Asn Asp Thr Phe Ala Lys Ala Arg Asp Val Gln Ala Ala<br>                  245                    250                    255 | 768 |
| gat cct gac aca ctg ccg aat acg tat ttg caa tat tat ttg ttc cca<br>Asp Pro Asp Thr Leu Pro Asn Thr Tyr Leu Gln Tyr Tyr Leu Phe Pro<br>                260                    265                    270 | 816 |
| gat gat atg gtg aaa aaa tca aat ccg aat cat acg cgg gcg aat gaa<br>Asp Asp Met Val Lys Lys Ser Asn Pro Asn His Thr Arg Ala Asn Glu<br>             275                    280                    285 | 864 |
| gtc atg gaa ggg cgc gaa gct ttt att ttc agc caa tgt gac atg atc<br>Val Met Glu Gly Arg Glu Ala Phe Ile Phe Ser Gln Cys Asp Met Ile<br>     290                    295                    300 | 912 |
| aca cgt gaa cag tcc tcg gaa aac agc gaa att aaa atc gat gac cac<br>Thr Arg Glu Gln Ser Ser Glu Asn Ser Glu Ile Lys Ile Asp Asp His<br>305                    310                    315                    320 | 960 |
| gca tcg tat atc gtt gat ctt gcc cgg gcg att gcc tac aac aca ggt<br>Ala Ser Tyr Ile Val Asp Leu Ala Arg Ala Ile Ala Tyr Asn Thr Gly<br>                  325                    330                    335 | 1008 |
| gaa aga atg ctg ttg att gtt gaa aac aac ggt gca att gcg aac ttt<br>Glu Arg Met Leu Leu Ile Val Glu Asn Asn Gly Ala Ile Ala Asn Phe<br>             340                    345                    350 | 1056 |
| gac ccg act gcg atg gtt gag gtg cca tgc atc gtc ggc tca aat gga<br>Asp Pro Thr Ala Met Val Glu Val Pro Cys Ile Val Gly Ser Asn Gly<br>     355                    360                    365 | 1104 |
| cct gaa ccg att acc gtt ggc acc att ccg caa ttc cag aaa ggg ctc<br>Pro Glu Pro Ile Thr Val Gly Thr Ile Pro Gln Phe Gln Lys Gly Leu<br>370                    375                    380 | 1152 |
| atg gag cag cag gta tcc gtt gag aag ctg act gtt gaa gcg tgg gca<br>Met Glu Gln Gln Val Ser Val Glu Lys Leu Thr Val Glu Ala Trp Ala<br>385                    390                    395                    400 | 1200 |
| gag aaa tcg ttc caa aag ctg tgg cag gcg ctg atc ctg tca aaa aca<br>Glu Lys Ser Phe Gln Lys Leu Trp Gln Ala Leu Ile Leu Ser Lys Thr<br>                  405                    410                    415 | 1248 |
| gtg ccg aac gcg cgt gtg gca aga ctc att ctt gag gat tta gtg gag<br>Val Pro Asn Ala Arg Val Ala Arg Leu Ile Leu Glu Asp Leu Val Glu<br>             420                    425                    430 | 1296 |

```
gcc aac aaa gac ttc tgg cct gag ctt gat caa agc cca acc cgc ata    1344
Ala Asn Lys Asp Phe Trp Pro Glu Leu Asp Gln Ser Pro Thr Arg Ile
        435             440             445 tca taa                                                            1350
Ser
```

<210> SEQ ID NO 40
<211> LENGTH: 449
<212> TYPE: PRT
<213> ORGANISM: Bacillus subtilis

<400> SEQUENCE: 40

```
Met Lys Lys Lys Ser Phe Ser Ile Val Ile Ala Gly Gly Gly Ser Thr
1               5                   10                  15

Phe Thr Pro Gly Ile Val Leu Met Leu Leu Asp His Leu Glu Glu Phe
            20                  25                  30

Pro Ile Arg Lys Leu Lys Leu Tyr Asp Asn Asp Lys Glu Arg Gln Asp
        35                  40                  45

Arg Ile Ala Gly Ala Cys Asp Val Phe Ile Arg Glu Lys Ala Pro Asp
    50                  55                  60

Ile Glu Phe Ala Ala Thr Thr Asp Pro Glu Glu Ala Phe Thr Asp Val
65                  70                  75                  80

Asp Phe Val Met Ala His Ile Arg Val Gly Lys Tyr Ala Met Arg Ala
                85                  90                  95

Leu Asp Glu Gln Ile Pro Leu Lys Tyr Gly Val Val Gly Gln Glu Thr
            100                 105                 110

Cys Gly Pro Gly Gly Ile Ala Tyr Gly Met Arg Ser Ile Gly Gly Val
        115                 120                 125

Leu Glu Ile Leu Asp Tyr Met Glu Lys Tyr Ser Pro Asp Ala Trp Met
    130                 135                 140

Leu Asn Tyr Ser Asn Pro Ala Ala Ile Val Ala Glu Ala Thr Arg Arg
145                 150                 155                 160

Leu Arg Pro Asn Ser Lys Ile Leu Asn Ile Cys Asp Met Pro Val Gly
                165                 170                 175

Ile Glu Asp Arg Met Ala Gln Ile Leu Gly Leu Ser Ser Arg Lys Glu
            180                 185                 190

Met Lys Val Arg Tyr Tyr Gly Leu Asn His Phe Gly Trp Trp Thr Ser
        195                 200                 205

Ile Gln Asp Gln Glu Gly Asn Asp Leu Met Pro Lys Leu Lys Glu His
    210                 215                 220

Val Ser Gln Tyr Gly Tyr Ile Pro Lys Thr Glu Ala Glu Ala Val Glu
225                 230                 235                 240

Ala Ser Trp Asn Asp Thr Phe Ala Lys Ala Arg Asp Val Gln Ala Ala
                245                 250                 255

Asp Pro Asp Thr Leu Pro Asn Thr Tyr Leu Gln Tyr Tyr Leu Phe Pro
            260                 265                 270

Asp Asp Met Val Lys Lys Ser Asn Pro Asn His Thr Arg Ala Asn Glu
        275                 280                 285

Val Met Glu Gly Arg Glu Ala Phe Ile Phe Ser Gln Cys Asp Met Ile
    290                 295                 300

Thr Arg Glu Gln Ser Ser Glu Asn Ser Glu Ile Lys Ile Asp Asp His
305                 310                 315                 320

Ala Ser Tyr Ile Val Asp Leu Ala Arg Ala Ile Ala Tyr Asn Thr Gly
                325                 330                 335
```

```
Glu Arg Met Leu Leu Ile Val Glu Asn Asn Gly Ala Ile Ala Asn Phe
            340                 345                 350

Asp Pro Thr Ala Met Val Glu Val Pro Cys Ile Val Gly Ser Asn Gly
        355                 360                 365

Pro Glu Pro Ile Thr Val Gly Thr Ile Pro Gln Phe Gln Lys Gly Leu
    370                 375                 380

Met Glu Gln Gln Val Ser Val Glu Lys Leu Thr Val Glu Ala Trp Ala
385                 390                 395                 400

Glu Lys Ser Phe Gln Lys Leu Trp Gln Ala Leu Ile Leu Ser Lys Thr
                405                 410                 415

Val Pro Asn Ala Arg Val Ala Arg Leu Ile Leu Glu Asp Leu Val Glu
            420                 425                 430

Ala Asn Lys Asp Phe Trp Pro Glu Leu Asp Gln Ser Pro Thr Arg Ile
        435                 440                 445

Ser

<210> SEQ ID NO 41
<211> LENGTH: 1584
<212> TYPE: DNA
<213> ORGANISM: Bacillus subtilis
<220> FEATURE:
<221> NAME/KEY: CDS
<222> LOCATION: (1)..(1584)

<400> SEQUENCE: 41
```

| | | | | | | | | | | | | | | | | |
|---|---|---|---|---|---|---|---|---|---|---|---|---|---|---|---|---|
| atg | atg | caa | aaa | att | cag | cgc | ttt | gga | agc | gcg | atg | ttt | gtg | cct | gtt | 48 |
| Met | Met | Gln | Lys | Ile | Gln | Arg | Phe | Gly | Ser | Ala | Met | Phe | Val | Pro | Val | |
| 1 | | | | 5 | | | | | 10 | | | | | 15 | | |
| tta | tta | ttc | gcg | ttc | gcc | ggc | att | atc | gtc | ggt | atc | agc | acg | ctc | ttt | 96 |
| Leu | Leu | Phe | Ala | Phe | Ala | Gly | Ile | Ile | Val | Gly | Ile | Ser | Thr | Leu | Phe | |
| | | | 20 | | | | | 25 | | | | | 30 | | | |
| aaa | aat | aaa | acc | ctc | atg | gga | ccg | ctc | gcc | gat | cct | gac | ggt | ttt | tgg | 144 |
| Lys | Asn | Lys | Thr | Leu | Met | Gly | Pro | Leu | Ala | Asp | Pro | Asp | Gly | Phe | Trp | |
| | | 35 | | | | | 40 | | | | | 45 | | | | |
| tat | cag | tgc | tgg | tat | atc | att | gag | cag | ggc | ggc | tgg | act | gtt | ttt | aac | 192 |
| Tyr | Gln | Cys | Trp | Tyr | Ile | Ile | Glu | Gln | Gly | Gly | Trp | Thr | Val | Phe | Asn | |
| | 50 | | | | | 55 | | | | | 60 | | | | | |
| caa | atg | ccg | ctc | tta | ttc | gcc | att | ggc | atc | ccg | gtt | gct | ttg | gcg | aag | 240 |
| Gln | Met | Pro | Leu | Leu | Phe | Ala | Ile | Gly | Ile | Pro | Val | Ala | Leu | Ala | Lys | |
| 65 | | | | | 70 | | | | | 75 | | | | | 80 | |
| aaa | gct | cag | gca | cgc | gcc | tgt | ttg | gaa | gcg | ctt | act | gtc | tac | ctg | aca | 288 |
| Lys | Ala | Gln | Ala | Arg | Ala | Cys | Leu | Glu | Ala | Leu | Thr | Val | Tyr | Leu | Thr | |
| | | | | 85 | | | | | 90 | | | | | 95 | | |
| ttc | aac | tat | ttt | gtc | agc | gcg | ata | ttg | acg | gta | tgg | gga | gga | gca | ttt | 336 |
| Phe | Asn | Tyr | Phe | Val | Ser | Ala | Ile | Leu | Thr | Val | Trp | Gly | Gly | Ala | Phe | |
| | | | 100 | | | | | 105 | | | | | 110 | | | |
| ggc | gtc | gac | atg | aat | caa | gag | gtc | gga | gga | acg | agc | ggg | tta | acg | atg | 384 |
| Gly | Val | Asp | Met | Asn | Gln | Glu | Val | Gly | Gly | Thr | Ser | Gly | Leu | Thr | Met | |
| | | 115 | | | | | 120 | | | | | 125 | | | | |
| att | gcg | ggc | ata | aaa | acg | ctc | gat | acc | aac | atc | atc | gga | gcc | atc | ttt | 432 |
| Ile | Ala | Gly | Ile | Lys | Thr | Leu | Asp | Thr | Asn | Ile | Ile | Gly | Ala | Ile | Phe | |
| | 130 | | | | | 135 | | | | | 140 | | | | | |
| att | tct | tcg | att | gtc | gtc | ttt | ttg | cat | aat | cgc | tat | ttt | gat | aaa | aaa | 480 |
| Ile | Ser | Ser | Ile | Val | Val | Phe | Leu | His | Asn | Arg | Tyr | Phe | Asp | Lys | Lys | |
| 145 | | | | | 150 | | | | | 155 | | | | | 160 | |
| ctg | ccc | gat | ttt | ctc | ggc | atc | ttt | caa | ggc | tca | aca | tat | atc | gtg | atg | 528 |
| Leu | Pro | Asp | Phe | Leu | Gly | Ile | Phe | Gln | Gly | Ser | Thr | Tyr | Ile | Val | Met | |
| | | | | 165 | | | | | 170 | | | | | 175 | | |
| att | tcc | ttc | ttt | att | atg | atc | cca | att | gcg | ttg | gct | gtg | tct | tat | att | 576 |

```
                Ile Ser Phe Phe Ile Met Ile Pro Ile Ala Leu Ala Val Ser Tyr Ile
                                180                 185                 190 tgg ccg atg gtt caa tcg gga atc ggc tcg ctt caa agc ttc ctg gtt          624
Trp Pro Met Val Gln Ser Gly Ile Gly Ser Leu Gln Ser Phe Leu Val
            195                 200                 205 gct tct ggg gcg gtg ggc gtt tgg ata tac acg ttt ttg gaa cgg att          672
Ala Ser Gly Ala Val Gly Val Trp Ile Tyr Thr Phe Leu Glu Arg Ile
210                 215                 220 tta att ccg acc ggc ctt cat cac ttt att tac acg ccg ttt att tat          720
Leu Ile Pro Thr Gly Leu His His Phe Ile Tyr Thr Pro Phe Ile Tyr
225                 230                 235                 240 ggc ccg gct gta gcg gaa ggc ggg atc gtc acg tat tgg gca cag cat          768
Gly Pro Ala Val Ala Glu Gly Gly Ile Val Thr Tyr Trp Ala Gln His
                245                 250                 255 ctc ggc gaa tat tcg caa agc gcc aaa ccg ctg aag gag ctc ttt ccg          816
Leu Gly Glu Tyr Ser Gln Ser Ala Lys Pro Leu Lys Glu Leu Phe Pro
            260                 265                 270 caa ggc gga ttc gcg ctt cac ggc aac tcg aaa atc ttc ggt att ccg          864
Gln Gly Gly Phe Ala Leu His Gly Asn Ser Lys Ile Phe Gly Ile Pro
        275                 280                 285 ggt atc gcc ctg gct ttt tat gtg aca gcc aaa aag gaa aag aaa aaa          912
Gly Ile Ala Leu Ala Phe Tyr Val Thr Ala Lys Lys Glu Lys Lys Lys
    290                 295                 300 ctc gtc gca ggg ctg ctg att cct gtc aca ctg aca gcg att gtc gcc          960
Leu Val Ala Gly Leu Leu Ile Pro Val Thr Leu Thr Ala Ile Val Ala
305                 310                 315                 320 ggt att aca gag ccg att gag ttt acg ttc tta ttc att tca cct ttc         1008
Gly Ile Thr Glu Pro Ile Glu Phe Thr Phe Leu Phe Ile Ser Pro Phe
                325                 330                 335 tta ttt gcg gtt cac gcc gtg ctt gcc gcc aca atg tcg aca gtt atg         1056
Leu Phe Ala Val His Ala Val Leu Ala Ala Thr Met Ser Thr Val Met
            340                 345                 350 tat atg gcc ggc gtc gtc gga aat atg gga ggc gga ctg att gag gcg         1104
Tyr Met Ala Gly Val Val Gly Asn Met Gly Gly Gly Leu Ile Glu Ala
        355                 360                 365 gta acc ttg aac tgg att ccg ctc ttt ggc agc cac ggt atg aca tat         1152
Val Thr Leu Asn Trp Ile Pro Leu Phe Gly Ser His Gly Met Thr Tyr
    370                 375                 380 gtg tat caa att ttg atc ggg ctc tcg ttt aca gca att tat ttt ttc         1200
Val Tyr Gln Ile Leu Ile Gly Leu Ser Phe Thr Ala Ile Tyr Phe Phe
385                 390                 395                 400 gtc ttc aga ttt tta atc ctc aaa ttc aat atc gct aca cca gga cgg         1248
Val Phe Arg Phe Leu Ile Leu Lys Phe Asn Ile Ala Thr Pro Gly Arg
                405                 410                 415 gaa aag gat gaa cag cag gaa aca aag cta tat tcg aaa aag gaa tac         1296
Glu Lys Asp Glu Gln Gln Glu Thr Lys Leu Tyr Ser Lys Lys Glu Tyr
            420                 425                 430 aga gaa cga aaa aac aag gat gaa acg gcc tcc gct gct gaa acg gct         1344
Arg Glu Arg Lys Asn Lys Asp Glu Thr Ala Ser Ala Ala Glu Thr Ala
        435                 440                 445 gat gac acc gct ttt ctg tat att gaa gcg ctg ggc gga aaa gac aac         1392
Asp Asp Thr Ala Phe Leu Tyr Ile Glu Ala Leu Gly Gly Lys Asp Asn
    450                 455                 460 atc act gaa gtc aca aac tgc gcc acc cgc ctc aga gtc agt gtc aag         1440
Ile Thr Glu Val Thr Asn Cys Ala Thr Arg Leu Arg Val Ser Val Lys
465                 470                 475                 480 gat gaa aca aag gtt gaa ccc gac agc gta ttc cgc gcg ctt ggc gca         1488
Asp Glu Thr Lys Val Glu Pro Asp Ser Val Phe Arg Ala Leu Gly Ala
                485                 490                 495
```

```
cac ggc gtt gtc agg aac ggg aag gcg ttt cag gta att atc gga tta    1536
His Gly Val Val Arg Asn Gly Lys Ala Phe Gln Val Ile Ile Gly Leu
            500                 505                 510 agc gtg ccg cag atg cgg gag cgt gtg gaa aaa ata ttg aat caa taa    1584
Ser Val Pro Gln Met Arg Glu Arg Val Glu Lys Ile Leu Asn Gln
        515                 520                 525
```

<210> SEQ ID NO 42
<211> LENGTH: 527
<212> TYPE: PRT
<213> ORGANISM: Bacillus subtilis

<400> SEQUENCE: 42

```
Met Met Gln Lys Ile Gln Arg Phe Gly Ser Ala Met Phe Val Pro Val
1               5                   10                  15

Leu Leu Phe Ala Phe Ala Gly Ile Ile Val Gly Ile Ser Thr Leu Phe
            20                  25                  30

Lys Asn Lys Thr Leu Met Gly Pro Leu Ala Asp Pro Asp Gly Phe Trp
        35                  40                  45

Tyr Gln Cys Trp Tyr Ile Ile Glu Gln Gly Gly Trp Thr Val Phe Asn
    50                  55                  60

Gln Met Pro Leu Leu Phe Ala Ile Gly Ile Pro Val Ala Leu Ala Lys
65                  70                  75                  80

Lys Ala Gln Ala Arg Ala Cys Leu Glu Ala Leu Thr Val Tyr Leu Thr
                85                  90                  95

Phe Asn Tyr Phe Val Ser Ala Ile Leu Thr Val Trp Gly Gly Ala Phe
            100                 105                 110

Gly Val Asp Met Asn Gln Glu Val Gly Gly Thr Ser Gly Leu Thr Met
        115                 120                 125

Ile Ala Gly Ile Lys Thr Leu Asp Thr Asn Ile Ile Gly Ala Ile Phe
    130                 135                 140

Ile Ser Ser Ile Val Val Phe Leu His Asn Arg Tyr Phe Asp Lys Lys
145                 150                 155                 160

Leu Pro Asp Phe Leu Gly Ile Phe Gln Gly Ser Thr Tyr Ile Val Met
                165                 170                 175

Ile Ser Phe Phe Ile Met Ile Pro Ile Ala Leu Ala Val Ser Tyr Ile
            180                 185                 190

Trp Pro Met Val Gln Ser Gly Ile Gly Ser Leu Gln Ser Phe Leu Val
        195                 200                 205

Ala Ser Gly Ala Val Gly Val Trp Ile Tyr Thr Phe Leu Glu Arg Ile
    210                 215                 220

Leu Ile Pro Thr Gly Leu His His Phe Ile Tyr Thr Pro Phe Ile Tyr
225                 230                 235                 240

Gly Pro Ala Val Ala Glu Gly Gly Ile Val Thr Tyr Trp Ala Gln His
                245                 250                 255

Leu Gly Glu Tyr Ser Gln Ser Ala Lys Pro Leu Lys Glu Leu Phe Pro
            260                 265                 270

Gln Gly Gly Phe Ala Leu His Gly Asn Ser Lys Ile Phe Gly Ile Pro
        275                 280                 285

Gly Ile Ala Leu Ala Phe Tyr Val Thr Ala Lys Lys Glu Lys Lys Lys
    290                 295                 300

Leu Val Ala Gly Leu Leu Ile Pro Val Thr Leu Thr Ala Ile Val Ala
305                 310                 315                 320

Gly Ile Thr Glu Pro Ile Glu Phe Thr Phe Leu Phe Ile Ser Pro Phe
                325                 330                 335
```

```
Leu Phe Ala Val His Ala Val Leu Ala Ala Thr Met Ser Thr Val Met
            340                 345                 350

Tyr Met Ala Gly Val Val Gly Asn Met Gly Gly Gly Leu Ile Glu Ala
        355                 360                 365

Val Thr Leu Asn Trp Ile Pro Leu Phe Gly Ser His Gly Met Thr Tyr
    370                 375                 380

Val Tyr Gln Ile Leu Ile Gly Leu Ser Phe Thr Ala Ile Tyr Phe Phe
385                 390                 395                 400

Val Phe Arg Phe Leu Ile Leu Lys Phe Asn Ile Ala Thr Pro Gly Arg
            405                 410                 415

Glu Lys Asp Glu Gln Gln Glu Thr Lys Leu Tyr Ser Lys Lys Glu Tyr
            420                 425                 430

Arg Glu Arg Lys Asn Lys Asp Glu Thr Ala Ser Ala Ala Glu Thr Ala
            435                 440                 445

Asp Asp Thr Ala Phe Leu Tyr Ile Glu Ala Leu Gly Gly Lys Asp Asn
            450                 455                 460

Ile Thr Glu Val Thr Asn Cys Ala Thr Arg Leu Arg Val Ser Val Lys
465                 470                 475                 480

Asp Glu Thr Lys Val Glu Pro Asp Ser Val Phe Arg Ala Leu Gly Ala
            485                 490                 495

His Gly Val Val Arg Asn Gly Lys Ala Phe Gln Val Ile Ile Gly Leu
            500                 505                 510

Ser Val Pro Gln Met Arg Glu Arg Val Glu Lys Ile Leu Asn Gln
            515                 520                 525

<210> SEQ ID NO 43
<211> LENGTH: 43
<212> TYPE: DNA
<213> ORGANISM: Artificial Sequence
<220> FEATURE:
<223> OTHER INFORMATION: PtacB promoter

<400> SEQUENCE: 43
ccctgttgga attaatcatc ggctcgtata atgtgtggaa tcg                    43
```